United States Patent
Zhao et al.

(10) Patent No.: US 11,946,162 B2
(45) Date of Patent: *Apr. 2, 2024

(54) DIRECTED EVOLUTION OF SYNTHETIC GENE CLUSTER

(71) Applicant: Massachusetts Institute of Technology, Cambridge, MA (US)

(72) Inventors: Dehua Zhao, Brookline, MA (US); Christopher A. Voigt, Belmont, MA (US); Michael Joseph Smanski, Falcon Heights, MN (US)

(73) Assignee: Massachusetts Institute of Technology, Cambridge, MA (US)

( * ) Notice: Subject to any disclaimer, the term of this patent is extended or adjusted under 35 U.S.C. 154(b) by 165 days.

This patent is subject to a terminal disclaimer.

(21) Appl. No.: 17/204,219

(22) Filed: Mar. 17, 2021

(65) Prior Publication Data
US 2021/0284995 A1 Sep. 16, 2021

Related U.S. Application Data

(63) Continuation of application No. 14/440,183, filed as application No. PCT/US2013/068055 on Nov. 1, 2013, now Pat. No. 10,968,446.
(Continued)

(51) Int. Cl.
*C40B 50/06* (2006.01)
*C12N 15/10* (2006.01)
(Continued)

(52) U.S. Cl.
CPC .......... *C40B 50/06* (2013.01); *C12N 15/1034* (2013.01); *C12N 15/1058* (2013.01); *C12N 15/1093* (2013.01); *C12N 15/66* (2013.01); *C40B 40/06* (2013.01); *G16B 20/20* (2019.02); *G16B 20/30* (2019.02); *G16B 35/00* (2019.02); *G16B 35/10* (2019.02); *G16B 35/20* (2019.02); *G16B 50/00* (2019.02); *G16B 50/30* (2019.02);
(Continued)

(58) Field of Classification Search
None
See application file for complete search history.

(56) References Cited

U.S. PATENT DOCUMENTS 1,520,545 A    12/1924 Murphy
4,782,022 A    11/1988 Puhler et al.
(Continued)

FOREIGN PATENT DOCUMENTS

AU    636565 B2    5/1993
CA    2051071 A1   3/1993
(Continued)

OTHER PUBLICATIONS

Watanabe et al. (2009) Methods in Enzymology vol. 458 pp. 379 to 399.*
(Continued)

*Primary Examiner* — Christian C Boesen
(74) *Attorney, Agent, or Firm* — Wolf, Greenfield & Sacks, P.C.

(57) ABSTRACT

The invention relates to methods and products for generating diverse libraries of genetic material. The products include libraries and constructed nucleic acids as well as kits and databases and systems thereof.

18 Claims, 41 Drawing Sheets

Specification includes a Sequence Listing.

Related U.S. Application Data

(60) Provisional application No. 61/721,188, filed on Nov. 1, 2012.

(51) Int. Cl.

| | | |
|---|---|---|
| *C12N 15/66* | (2006.01) | |
| *C40B 40/06* | (2006.01) | |
| *G16B 20/20* | (2019.01) | |
| *G16B 20/30* | (2019.01) | |
| *G16B 35/00* | (2019.01) | |
| *G16B 35/10* | (2019.01) | |
| *G16B 35/20* | (2019.01) | |
| *G16B 50/00* | (2019.01) | |
| *G16B 50/30* | (2019.01) | |
| *G16C 20/60* | (2019.01) | |
| *C40B 40/08* | (2006.01) | |
| *G16B 20/00* | (2019.01) | |
| *G16B 40/00* | (2019.01) | |

(52) U.S. Cl.
CPC .............. *G16C 20/60* (2019.02); *C40B 40/08* (2013.01); *G16B 20/00* (2019.02); *G16B 40/00* (2019.02)

(56) References Cited

U.S. PATENT DOCUMENTS

| | | |
|---|---|---|
| 4,832,728 A | 5/1989 | Allan et al. |
| 5,071,743 A | 12/1991 | Slilaty et al. |
| 5,116,506 A | 5/1992 | Williamson et al. |
| 5,188,960 A | 2/1993 | Payne et al. |
| 5,229,291 A | 7/1993 | Nielsen et al. |
| 5,354,670 A | 10/1994 | Nickoloff et al. |
| 5,427,785 A | 6/1995 | Ronson et al. |
| 5,610,044 A | 3/1997 | Lam et al. |
| 5,780,270 A | 7/1998 | Lesley |
| 5,789,166 A | 8/1998 | Bauer et al. |
| 5,877,012 A | 3/1999 | Estruch et al. |
| 5,880,275 A | 3/1999 | Fischhoff et al. |
| 5,916,029 A | 6/1999 | Smith et al. |
| 6,033,861 A | 3/2000 | Schaffer et al. |
| 6,033,874 A | 3/2000 | Baum et al. |
| 6,083,499 A | 7/2000 | Narva et al. |
| 6,107,279 A | 8/2000 | Estruch et al. |
| 6,127,180 A | 10/2000 | Narva et al. |
| 6,137,033 A | 10/2000 | Estruch et al. |
| 6,218,188 B1 | 4/2001 | Cardineau et al. |
| 6,248,535 B1 | 6/2001 | Danenberg et al. |
| 6,326,351 B1 | 12/2001 | Donovan et al. |
| 6,340,593 B1 | 1/2002 | Cardineau et al. |
| 6,391,548 B1 | 5/2002 | Bauer et al. |
| 6,399,330 B1 | 6/2002 | Donovan et al. |
| 6,548,289 B1 | 4/2003 | Beynon et al. |
| 6,548,291 B1 | 4/2003 | Narva et al. |
| 6,596,509 B1 | 7/2003 | Bauer et al. |
| 6,624,145 B1 | 9/2003 | Narva et al. |
| 6,673,610 B2 | 1/2004 | Miyawaki et al. |
| 6,713,063 B1 | 3/2004 | Malvar et al. |
| 6,713,285 B2 | 3/2004 | Bauer et al. |
| 6,773,900 B2 | 8/2004 | Short et al. |
| 6,841,358 B1 | 1/2005 | Locht et al. |
| 6,949,626 B2 | 9/2005 | Donovan et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,084,331 B2 | 8/2006 | Isawa et al. |
| 7,105,332 B2 | 9/2006 | Abad et al. |
| 7,132,265 B2 | 11/2006 | Bauer et al. |
| 7,244,820 B2 | 7/2007 | Miles et al. |
| 7,329,736 B2 | 2/2008 | Abad et al. |
| 7,378,499 B2 | 5/2008 | Abad et al. |
| 7,385,107 B2 | 6/2008 | Donovan et al. |
| 7,449,552 B2 | 11/2008 | Abad et al. |
| 7,462,760 B2 | 12/2008 | Abad et al. |
| 7,470,427 B2 | 12/2008 | Cocking |
| 7,476,781 B2 | 1/2009 | Abad et al. |
| 7,485,451 B2 | 2/2009 | Vandergheynst et al. |
| 7,491,698 B2 | 2/2009 | Hey et al. |
| 7,491,869 B2 | 2/2009 | Abad et al. |
| 7,504,229 B2 | 3/2009 | Donovan et al. |
| 7,615,686 B2 | 11/2009 | Miles et al. |
| 7,803,943 B2 | 9/2010 | Mao et al. |
| 7,858,849 B2 | 12/2010 | Cerf et al. |
| 7,888,552 B2 | 2/2011 | Ye et al. |
| 7,923,602 B2 | 4/2011 | Carozzi et al. |
| 8,076,142 B2 | 12/2011 | Huang et al. |
| 8,084,416 B2 | 12/2011 | Sampson et al. |
| 8,084,418 B2 | 12/2011 | Hey et al. |
| 8,137,665 B2 | 3/2012 | Cocking |
| 8,236,757 B2 | 8/2012 | Carozzi et al. |
| 8,237,020 B2 | 8/2012 | Miles et al. |
| 8,268,584 B1 | 9/2012 | Hardwood et al. |
| 8,304,604 B2 | 11/2012 | Lira et al. |
| 8,304,605 B2 | 11/2012 | Lira et al. |
| 8,319,019 B2 | 11/2012 | Abad et al. |
| 8,334,366 B1 | 12/2012 | Hughes et al. |
| 8,334,431 B2 | 12/2012 | Sampson et al. |
| 8,377,671 B2 | 2/2013 | Cournac et al. |
| 8,481,026 B1 | 7/2013 | Woodruff et al. |
| 8,513,494 B2 | 8/2013 | Wu et al. |
| 8,530,411 B2 | 9/2013 | Cerf et al. |
| 8,575,433 B2 | 11/2013 | Cerf et al. |
| 8,686,233 B2 | 4/2014 | Cerf et al. |
| 8,759,619 B2 | 6/2014 | Sampson et al. |
| 8,795,965 B2 | 8/2014 | Zjang |
| 8,802,933 B2 | 8/2014 | Abad et al. |
| 8,802,934 B2 | 8/2014 | Abad et al. |
| 9,150,851 B2 | 10/2015 | Wigley et al. |
| 9,321,697 B2 | 4/2016 | Das et al. |
| 9,487,451 B2 | 11/2016 | Doty et al. |
| 9,512,431 B2 | 12/2016 | Mirsky et al. |
| 9,657,298 B2 | 5/2017 | Soto et al. |
| 9,796,957 B2 | 10/2017 | Barney et al. |
| 9,957,509 B2 | 5/2018 | Mirsky et al. |
| 9,975,817 B2 | 5/2018 | Temme et al. |
| 9,994,557 B2 | 6/2018 | Davidson et al. |
| 10,384,983 B2 | 8/2019 | Temme et al. |
| 10,525,318 B2 | 1/2020 | Dougherty |
| 10,556,839 B2 | 2/2020 | Temme et al. |
| 10,662,432 B2 | 5/2020 | Mirsky et al. |
| 10,919,814 B2 | 2/2021 | Temme et al. |
| 10,934,226 B2 | 3/2021 | Temme et al. |
| 10,968,446 B2 | 4/2021 | Zhao et al. |
| 2004/0197916 A1 | 10/2004 | Carozzi et al. |
| 2004/0197917 A1 | 10/2004 | Carozzi et al. |
| 2004/0210964 A1 | 10/2004 | Carozzi et al. |
| 2004/0210965 A1 | 10/2004 | Carozzi et al. |
| 2004/0216186 A1 | 10/2004 | Carozzi et al. |
| 2004/0235663 A1 | 11/2004 | Cocking |
| 2004/0241847 A1 | 12/2004 | Okuyama et al. |
| 2004/0250311 A1 | 12/2004 | Carozzi et al. |
| 2005/0081262 A1 | 4/2005 | Cook et al. |
| 2005/0266541 A1 | 12/2005 | Dillon |
| 2006/0033867 A1 | 2/2006 | Krisko et al. |
| 2006/0096918 A1 | 5/2006 | Semmens |
| 2006/0112447 A1 | 5/2006 | Bogdanova et al. |
| 2006/0127988 A1 | 6/2006 | Wood et al. |
| 2006/0191034 A1 | 8/2006 | Baum |
| 2006/0243011 A1 | 11/2006 | Someus |
| 2008/0295207 A1 | 11/2008 | Baum et al. |
| 2008/0311632 A1 | 12/2008 | Figge et al. |
| 2009/0105076 A1 | 4/2009 | Stewart et al. |
| 2009/0137390 A1 | 5/2009 | Triplett |
| 2009/0144852 A1 | 6/2009 | Tomso et al. |
| 2009/0152195 A1 | 6/2009 | Rodgers et al. |
| 2009/0162477 A1 | 6/2009 | Nadel |
| 2009/0258404 A1 | 10/2009 | Mikkelsen et al. |
| 2010/0005543 A1 | 1/2010 | Sampson et al. |
| 2010/0017914 A1 | 1/2010 | Hart et al. |
| 2010/0028870 A1 | 2/2010 | Welch et al. |
| 2010/0184038 A1 | 7/2010 | Boddy et al. |
| 2010/0197592 A1 | 8/2010 | Heinrichs |
| 2010/0267147 A1 | 10/2010 | Qiao |

(56) References Cited

U.S. PATENT DOCUMENTS

| | | |
|---|---|---|
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0104690 A1 | 5/2011 | Yu et al. |
| 2011/0263488 A1 | 10/2011 | Carozzi et al. |
| 2012/0015806 A1 | 1/2012 | Paikray et al. |
| 2012/0107889 A1 | 5/2012 | Doty et al. |
| 2012/0192605 A1 | 8/2012 | McSpadden Gardener et al. |
| 2012/0266332 A1 | 10/2012 | Kuykendall |
| 2012/0278954 A1 | 11/2012 | Bowen et al. |
| 2012/0284813 A1 | 11/2012 | Oliver et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0126428 A1 | 5/2013 | Jones et al. |
| 2013/0167268 A1 | 6/2013 | Narva et al. |
| 2013/0167269 A1 | 6/2013 | Narva et al. |
| 2014/0011261 A1 | 1/2014 | Wang et al. |
| 2014/0182018 A1 | 6/2014 | Lang et al. |
| 2014/0223598 A1 | 8/2014 | Sampson et al. |
| 2014/0223599 A1 | 8/2014 | Sampson et al. |
| 2014/0230504 A1 | 8/2014 | Finlayson et al. |
| 2014/0273226 A1 | 9/2014 | Wu |
| 2014/0329326 A1 | 11/2014 | Mirsky |
| 2014/0336050 A1 | 11/2014 | Soto et al. |
| 2015/0080261 A1 | 3/2015 | Wigley et al. |
| 2015/0101373 A1 | 4/2015 | Munusamy et al. |
| 2015/0128670 A1 | 5/2015 | Das |
| 2015/0237807 A1 | 8/2015 | Valiquette |
| 2015/0315570 A1 | 11/2015 | Zhao et al. |
| 2016/0174570 A1 | 6/2016 | Vujanovic et al. |
| 2016/0292355 A1 | 10/2016 | Lou et al. |
| 2017/0086402 A1 | 3/2017 | Meadows-Smith |
| 2017/0119690 A1 | 5/2017 | Hansen et al. |
| 2017/0152519 A1 | 6/2017 | Mirsky et al. |
| 2017/0367349 A1 | 12/2017 | Gruver et al. |
| 2018/0002243 A1 | 1/2018 | Temme et al. |
| 2018/0073028 A1 | 3/2018 | Mirsky |
| 2018/0273437 A1 | 9/2018 | Temme et al. |
| 2018/0290942 A1 | 10/2018 | Voigt et al. |
| 2018/0297905 A1 | 10/2018 | Temme et al. |
| 2018/0297906 A1 | 10/2018 | Temme et al. |
| 2019/0039964 A1 | 2/2019 | Temme et al. |
| 2019/0144352 A1 | 5/2019 | Temme et al. |
| 2020/0087221 A1 | 3/2020 | Temme et al. |
| 2020/0115715 A1 | 4/2020 | Mirsky et al. |
| 2020/0299637 A1 | 9/2020 | Voigt et al. |
| 2020/0308594 A1 | 10/2020 | Tamsir et al. |
| 2020/0331820 A1 | 10/2020 | Tamsir et al. |
| 2021/0009483 A1 | 1/2021 | Temme et al. |
| 2021/0163374 A1 | 6/2021 | Bioch et al. |
| 2021/0214282 A1 | 7/2021 | Temme et al. |
| 2021/0315212 A1 | 10/2021 | Rezaei et al. |
| 2022/0017911 A1 | 1/2022 | Temme et al. |
| 2022/0079163 A1 | 3/2022 | Reisinger et al. |

FOREIGN PATENT DOCUMENTS

| | | |
|---|---|---|
| CN | 1289852 A | 4/2001 |
| CN | 1500801 A | 6/2004 |
| CN | 103451130 A | 12/2004 |
| CN | 1746304 A | 3/2006 |
| CN | 101880676 A | 11/2010 |
| CN | 102041241 A | 5/2011 |
| CN | 102417882 A | 4/2012 |
| CN | 102690808 A | 9/2012 |
| CN | 1552846 A | 12/2013 |
| CN | 104136599 A | 11/2014 |
| EP | 292984 A2 | 11/1988 |
| EP | 339830 B1 | 11/1989 |
| EP | 1535913 B1 | 6/2005 |
| EP | 2186890 A1 | 5/2010 |
| EP | 3322679 A1 | 5/2018 |
| FR | 2910230 A1 | 6/2008 |
| JP | S63-501924 A | 8/1988 |
| JP | H01-225483 A | 9/1989 |
| JP | H02-131581 A | 5/1990 |
| JP | 2009-232721 A | 10/2009 |
| JP | 2014096996 A | 5/2014 |
| JP | 2015-037385 A | 2/2015 |
| JP | 2015-113274 A | 6/2015 |
| JP | 2015-518023 A | 6/2015 |
| JP | 2015-519352 A | 7/2015 |
| WO | WO 1987/004182 A1 | 7/1987 |
| WO | WO 1993/005154 A1 | 3/1993 |
| WO | WO 1998/010088 A1 | 3/1998 |
| WO | WO 1999/009834 A2 | 3/1999 |
| WO | WO 2000/057183 A1 | 9/2000 |
| WO | WO 2001/007567 A1 | 2/2001 |
| WO | WO 2004/074462 A2 | 9/2004 |
| WO | WO 2005/021585 A2 | 3/2005 |
| WO | WO 2005/038032 A1 | 4/2005 |
| WO | WO 2006/005100 A1 | 1/2006 |
| WO | WO 2006/083891 A2 | 8/2006 |
| WO | WO 2006/098225 A1 | 9/2006 |
| WO | WO 2006/119457 A2 | 11/2006 |
| WO | WO 2007/027776 A1 | 3/2007 |
| WO | WO 2009/060012 A2 | 5/2009 |
| WO | WO 2009/091557 A1 | 7/2009 |
| WO | WO 2010/080184 A1 | 7/2010 |
| WO | WO 2011/099019 A1 | 8/2011 |
| WO | WO 2011/099024 A1 | 8/2011 |
| WO | WO 2011/103247 A2 | 8/2011 |
| WO | WO 2011/103248 A2 | 8/2011 |
| WO | WO 2011/154960 A1 | 12/2011 |
| WO | WO 2012/139004 A1 | 10/2012 |
| WO | WO 2012/154651 A1 | 11/2012 |
| WO | WO 2012/174271 A2 | 12/2012 |
| WO | WO 2013/076687 A2 | 5/2013 |
| WO | WO 2013/132518 A1 | 9/2013 |
| WO | WO 2014/042517 A2 | 3/2014 |
| WO | WO 2014/071182 A1 | 5/2014 |
| WO | WO 2014/201044 A2 | 12/2014 |
| WO | WO 2016/016629 A1 | 2/2016 |
| WO | WO 2016/016630 A1 | 2/2016 |
| WO | WO 2016/100727 A1 | 6/2016 |
| WO | WO 2016/146955 A1 | 9/2016 |
| WO | WO 2016/178580 A2 | 11/2016 |
| WO | WO 2016/181228 A2 | 11/2016 |
| WO | WO 2017/042833 A1 | 3/2017 |
| WO | WO 2017/062412 A1 | 4/2017 |
| WO | WO 2017/085235 A1 | 5/2017 |
| WO | WO 2017/112827 A1 | 6/2017 |
| WO | WO 2017/203440 A1 | 11/2017 |
| WO | WO 2018/081543 A1 | 5/2018 |
| WO | WO 2018/132774 A1 | 7/2018 |
| WO | WO 2018/133774 A1 | 7/2018 |
| WO | WO 2019/032926 A1 | 2/2019 |
| WO | WO 2019/084342 A1 | 5/2019 |
| WO | WO 2020/006064 A2 | 1/2020 |
| WO | WO 2020/006246 A1 | 1/2020 |
| WO | WO 2020/014498 A1 | 1/2020 |
| WO | WO 2020/023630 A1 | 1/2020 |
| WO | WO 2020/061363 A1 | 3/2020 |
| WO | WO 2020/092940 A1 | 5/2020 |
| WO | WO 2020/118111 A1 | 6/2020 |
| WO | WO 2020/146372 A1 | 7/2020 |
| WO | WO 2020/163251 A1 | 8/2020 |
| WO | WO 2020/190363 A1 | 9/2020 |
| WO | WO 2020/191201 A1 | 9/2020 |
| WO | WO 2020/219893 A1 | 10/2020 |
| WO | WO 2020/219932 A1 | 10/2020 |

(56) References Cited

FOREIGN PATENT DOCUMENTS

| WO | WO 2021/113352 A1 | 6/2021 |
|---|---|---|
| WO | WO 2021/146209 A1 | 7/2021 |

OTHER PUBLICATIONS

International Search Report and Written Opinion for PCT/US2013/068055 dated Feb. 18, 2014.
International Preliminary Report on Patentability for PCT/US2013/068055 dated May 14, 2015.
Alper et al., Tuning genetic control through promoter engineering. Proc Natl Acad Sci U S A. Sep. 6, 2005;102(36):12678-83. Epub Aug. 25, 2005. Erratum in: Proc Natl Acad Sci U S A. Feb. 21, 2006;103(8):3006.
Altschul et al. Basic local alignment search tool. J Mol Biol 215(3):403-410 (1990).
Barney et al., Gene deletions resulting in increased nitrogen release by azotobacter vinelandii: application of a novel nitrogen biosensor. Appl. Environ. Microbiol. 2015; 81(13):4316-4328. Published online Apr. 17, 2015.
Bikard et al., The synthetic integron: an in vivo genetic shuffling device. Nucleic Acids Res. Aug. 2010;38(15):e153. doi:10.1093/nar/gkq511. Epub Jun. 9, 2010.
Bilitchenko et al., Eugene—a domain specific language for specifying and constraining synthetic biological parts, devices, and systems. PLoS One. Apr. 29, 2011;6(4):e18882. doi: 10.1371/journal.pone.0018882. 12 pages.
Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012.
Engler, et al. A one pot, one step, precision cloning method with high throughput capability. PLoS One. 2008;3(11):e3647. doi: 10.1371/journal.pone.0003647. Epub Nov. 5, 2008. 7 pages.
Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009. 9 pages.
Fischbach et al., Prokaryotic gene clusters: A rich toolbox for synthetic biology. Biotechnol J. 2010;15(12):1277-96.
Frasch et al., Design-based re-engineering of biosynthetic gene clusters: plug-and-play in practice. Curr Opin Biotechnol. Dec. 2013;24(6):1144-50. doi: 10.1016/j.copbio.2013.03.006. Epub Mar. 27, 2013.
Kurzweil, Plant Bacteria breakthrough enables crops worldwide to take nitrogen from the air. Plant Bacteria Breakthrough Enables Crops Worldwide Take Nitrogen From Air. Aug. 1, 2013. 4 pages.
Lim et al., Fundamental relationship between operon organization and gene expression. PNAS USA. Jun. 28, 2011;108(26):10626-31. doi: 10.1073/pnas.1105692108. Epub Jun. 13, 2011.
Martinez-Noel et al., NifB and NifEN protein levels are regulated by ClpX2 under nitrogen fixation conditions in Azotobacter vinelandii. Mol Microbiol. Mar. 2011;79(5):1182-93. doi: 10.1111/j.1365-2958.2011.07540.x. Epub Jan. 25, 2011.
Medema et al., Computational tools for the synthetic design of biochemical pathways. Nat Rev Microbiol. Jan. 23, 2012;10(3):191-202. doi: 10.1038/nrmicro2717.
Rogers et al., Synthetic biology approaches to engineering the nitrogen symbiosis in cereals. J Exper Botany. 2014;65(8):1939-46.
Rosenblueth et al., Bacterial Endophytes and Their Interaction with Hosts. Mol Plant Microbe Interact. Aug. 2006;19(8):827-37.
Shamseldin, The role of different genes involved in symbiotic nitrogen fixation—review. Global J Biotechnol Biochem. 2013;8(4):84-94.
Sleight et al., Designing and engineering evolutionary robust genetic circuits. J Biol Engin. 2010;4(12):1-20.
Smanski et al., Synthetic biology to access and expand nature's chemical diversity. Nat Rev Microbiol. Mar. 2016;14(3):135-49. doi: 10.1038/nrmicro.2015.24.

Smanski, et al. Functional optimization of gene clusters by combinatorial design and assembly. Nat Biotechnol. Dec. 2014;32(12):1241-9. doi: 10.1038/nbt.3063. Epub Nov. 24, 2014, 12 pages.
Stemple, Tilling—a high-throughput harvest for functional genomics. Nat Rev Genet. Feb. 2004;5:145-50. doi: 10.1038/nrg1273.
Temme et al., Modular control of multiple pathways using engineered orthogonal T7 polymerases. Nucleic Acids Res. Sep. 1, 2012;40(17):8773-81. Epub Jun. 28, 2012.
Temme, Designing and Engineering Complex Behavior in Living Machines. University of California, San Francisco Dissertation. Doctor of Philosophy in Bioengineering. Oct. 1, 2011. 74 pages.
Temme, et al., Refactoring the nitrogen fixation gene cluster from Klebsiella oxytoca. PNAS, May 1, 2012;109(18):7085-90.
Voigt et al., Genetic parts to program bacteria. Curr Opin Biotechnol. 2006;17(5):548-57.
Voigt, Gaining Access: Rebuilding Genetics from the Ground Up. MIT. Department of Biological Engineering. Mar. 14, 2011. 20 pages.
Wang et al., Using Synthetic biology to distinguish and overcome regulatory and functional barriers related to nitrogen fixation. PLoS One. 2013;8(7):e68677. 11 pages.
Weber et al., A modular cloning system for standardized assembly of multigene constructs. PLoS One. Feb. 18, 2011;6(2):e16765, 11 pages. doi: 10.1371/journal.pone.0016765.
Welch et al., Design Parameters to Control Synthetic Gene Expression in *Escherichia coli*. PLoS One. Sep. 2009;4(9):e7002, 10 pages.
Werner et al., Fast track assembly of multigene constructs using Golden Gate cloning and the MoClo system. Bioeng Bugs. Jan. 1, 2012;3(1):38-43. doi: 10.1371/journal.pone.0016765. Epub Jan. 1, 2012.
Zhang et al., Influence of different factors on the nitrogenase activity of the engineered *Escherichia coli* 78-7. World J Microbiol Biotechnol. 2015;31:921-7. doi: 10.1007/s11274-015-1846-x.
US 8,476,226, 11/1999, Koenck (withdrawn)
[No Author Listed] cera-gmc.org [online], GM Crop Database. Center for Environmental Risk Assessment (CERA), 2010, retrieved from <http://ucbiotech.org/biotech_info/PDFs/Center_for_Environmental_Risk_Assessment_CERA_2011_GM_Crop_Database.pdf>, 1 page.
[No Author Listed] Emboss. Emboss Needle: Pairwise Sequence Alignment (Nucleotide). Available at URL<http://www.ebi.ac.uk/Tools/psa/emboss_needle/nucleotide.html>, Accessed on Oct. 10, 2016, 1 page.
<No Author Listed>, "T7 RNA Polymerase Expression System for Bacillus megaterium," T7 RNAP Expression System Handbook, Jan. 2010, © MoBiTec GmbH, 18 pages.
<No Author Listed>, 40 CFR 725.3 U.S. Government Publishing Office (Jul. 1, 2010) https://www.gpo.gov/fdsys/pkg/CFR-2010-title40-vol30/pdf/CFR-2010-title40-vol30-sec725-3.pdf (Year: 2010), 3 pages.
Altschul et al., "BLAST. Basic local alignment search tool," 2021, retrieved on Apr. 8, 2021, retrieved from URL <https://blast.ncbi.nlm.nih.gov/Blast.cgi>, 3 pages.
Altschul et al., "Gapped BLAST and PSI-BLAST: a new generation of protein database search programs," Nucleic Acids Res., 1997, 25:3389-3402.
Amalraj et al., Effect of Polymeric Additives, Adjuvants, Surfactants on Survival, Stability and Plant Growth Promoting Ability of Liquid Bioinoculants. J. Plant Physiol Pathol, 2013, 1:2, 6 pages.
Ambrosio et al., "Metabolic engineering of a diazotrophic bacterium improves ammonium release and biofertilization of plants and microalgae," Metab Eng., Mar. 2017, 40:59-68.
An et al., "Constitutive expression of the nifA gene activates associative nitrogen fixation of Enterobacter gergoviae 57-7, an opportunistic endophytic diazotroph," Journal of Applied Microbiology, 2007, 103(3):613-620.
Andersen et al., "Energetics of biological nitrogen fixation: determination of the ratio of formation of H2 to NH4+ catalysed by nitrogenase of Klebsiella pneumoniae in vivo," J Gen Microbial., Nov. 1977, 103(1):107-22.

(56) References Cited

OTHER PUBLICATIONS

Andersen et al., "Herpesvirus-mediated gene delivery into the rat brain: specificity and efficiency of the neuron-specific enolase promoter," Cell. Mol. Neurobiol., 1993, 13:503-515.

Anderson et al., "BglBricks: A flexible standard for biological part assembly," Journal of Biological Engineering, 2010, 4:1, 12 pages.

Andrews et al., "Use of Nitrogen Fixing Bacteria Inoculants as a Substitute for Nitrogen Fertiliser for Dryland Graminaceous Crops: Progress Made, Mechanisms of Action and Future Potential," Symbiosis, 2003, 34:21 pages.

Arriel-Elias et al., Shelf life enhancement of plant growth promoting rhizobacteria using a simple formulation screening method. African J Microbiology Research, Feb. 2018, 12(5):115-126.

Arsene et al., "Modulation of NifA activity by PII in Azospirillum brasilense: Evidence for a Regulatory role of the NifA N-Terminal Domain," Journal of Bacteriology, Aug. 1996, 178(16):4830-4838.

Austin et al. "Characterisation of the Klebsiella pneumoniae nitrogen-fixation regulatory proteins NIFA and NIFL in vitro," Eur J Biochem., 1990, 187(2):353-360.

Ausubel et al., "Glutamine Synthetase Mutations Which Affect Expression of Nitrogen Fixation Genes in Klebsiella pneumoniae," J Bacteriol, Nov. 1979, 140(2):597-606.

Bageshwar et al., "An Environmentally Friendly Engineered Azotobacter Strain That Replaces a Substantial Amount of Urea Fertilizer while Sustaining the Same Wheat Yield," Appl Environ Microbial., Aug. 2017, 83(15):e00590-17.

Bali et al., "Excretion of Ammonium by a nifL Mutant of Azotobacter vinelandii fixing Nitrogen," Applied and Environmental Microbiology, May 1992, 58(5):1711-1718.

Barney et al., "Transcriptional analysis of an Ammonium-excreting stain of azotobacter vinelandii deregulated for nitrogen fixation," Appl. Environ. Microbial. Jul. 2017, 83(20):1-22.

Barrango et al., "Exploiting CRISPR-Cas immune systems for genome editing in bacteria," Curr. Opin. Biotechnol., Nov. 2016, 37:61-68.

Bashor et al., Understanding Biological Regulation Through Synthetic Biology. Annu Rev Biophys. May 20, 2018;47:399-423. doi: 10.1146/annurev-biophys-070816-033903. Epub Mar. 16, 2018.

Baum et al., "Control of coleopteran insect pests through RNA interference," Nature Biotechnology, Nov. 2007, 25(11):1322-1326.

Bender et al., "Regulatory mutations in the Klebsiella aerogenes structural gene for glutamine synthetase," J Bacteriol., Oct. 1977, 132(1):100-105.

Beringer et al., "Genetic engineering and nitrogen fixation," Biotech. Gen. Eng. Rev., Feb. 1984, 1(1):65-88.

Berninger et al., Maintenance and assessment of cell viability in formulation of non-sporulating bacterial inoculants. Microb. Biotechnol., Mar. 2018, 11(2):277-301 (2018); doi: 10.1111/1751-7915.12880.

Berrada et al., Taxonomy of the rhizobia: current perspectives. British Microbiol Res J. 2014: 4(6): 616-39.

Biswas et al., Rhizobia inoculation improves nutrient uptake and growth of lowland rice. Soil Sci Soc Am J 2000; 64:1644-50.

Biswas et al., Rhizobial inoculation influences seedling vigor and yield of rice. Agronom J. 2000; 92: 880-6.

Bittner et al., "RpoS and RpoN are involved in the growth-dependent regulation of rfaH transcription and O antigen expression in *Salmonella enterica* serovar typhi," Microbial Pathogenesis, Jan. 2004, 36(1):19-24.

Blanco et al., "Sequence and molecular analysis of the nifL gene of Azotobacter vine landii." Mol Microbial. Aug. 1993, 9(4):869-79.

Bloch et al., Biological nitrogen fixation in maize: optimizing nitrogenase expression in a rootassociated diazotroph. J Experimental Botany, Jul. 2020, 71(15):4591-4603.

Bosmans et al., "Sea anemone venom as a source of insecticidal peptides acting on voltage-gated Na+ channels," Toxicon, Mar. 2007, 49(4):550-560.

Brewin et al., "The Basis of Ammonium release in nifL Mutants of Azotobacter vinelandii," Journal of Bacteriology, Dec. 1999, 181(23):7356-7362.

Buchanan-Wollaston et al., "Role of the nifA gene product in the regulation of nif expression in Klebsiella pneumoniae," Nature., Dec. 1981, 294(5843):776-8.

Buddrus-Schiemann et al., "Root colonization by *Pseudomonas* sp. DSMZ 13134 and impact on the indigenous rhizosphere bacterial community of barley." Microb Ecol. Aug. 2010, 60(2):381-393.

Cannon et al., Chromosomal integration of Klebsiella nitrogen fixation genes in *Escherichia coli*. J Gen Microbiol. Jan. 1974;80(1):227-39.

Cannon et al., Plasmids formed in nitrogen-fixing *Escherichia coli*-Klebsiella pneumoniae hybrids. J Gen Microbiol. Jan. 1974;80(1):241-51.

Chakroun et al., "Bacterial Vegetative Insecticidal Proteins (Vip) from Entomopathogenic Bacteria," Microbiol Mol Biol Rev., Mar. 2016, 80(2):329-50.

Chan et al., "Refactoring bacteriophage T7," Molecular Systems Biology, 2005, 1(1):E1-E10.

Chen et al., "Characterization of 582 natural and synthetic terminators and quantification of their design constraints," Nat. Methods, 2013, 10:659-664.

Chen et al., "Complete genome sequence of Kosakonia sacchari type strain SP1 T," Stand Genomic Sci., Jun. 15, 2014, 9(3):1311-1318.

Chen et al., "Expression of rat bone sialoprotein promoter in transgenic mice," J Bone Miner Res., May 1996, 11(5):654-64.

Chiang et al., "Mutagenic Oligonucleotide-directed PCR Amplification (Mod-PCR): An Efficient Method for Generating Random Base Substitution Mutations in a DNA sequence element," PCR methods and applications, 1993, 2:210-217.

Choi et al., "A Tn7-based broad-range bacterial cloning and expression system," Nat Methods, Jun. 2005, 2(6):443-8.

Choudhary et al., "Interactions of *Bacillus* spp. and Plants—With Special Reference to Induced Systemic Resistance (ISR)," Microbiological Research, 2009, 164(5):493-513.

Clancy et al., "The domains carrying the opposing activities in adenylyltransferase are separated by a central regulatory domain," FEBS Journal, 2007, 274(11):2865-2877.

Cohen, "In vitro Tomato Fruit Cultures Demonstrate a Role for Indole-3-acetic Acid in Regulating Fruit Ripening," J. Amer. Soc. Hort. Sci., 1996, 121(3):520-524.

Colby, Calculating Synergistic and Antagonistic Responses of Herbicide Combinations. Weeds, Jan. 1967, 15(1):20-22, 4 pages.

Colebatch et al., "Symbiotic nitrogen fixation research in the postgenomics era," New Phytologist., 2002, 153(1):37-42.

Colnaghi et al., "Lethality of glnD null mutations in Azotobacter vinelandii is suppressible by prevention of glutamine synthetase adenylylation," Microbiology, May 2001, 147(Pt 5):1267-76.

Colnaghi et al., "Strategies for increased ammonium production in free-living or plant associated nitrogen fixing bacteria," Plant and Soil, Nov. 1997, 194:145-154.

Compant et al., "A review on the plant microbiome: Ecology, functions, and emerging trends in microbial application," Journal of Advanced Research, Sep. 2019, 19:29-37.

Conniff, "Microbes Help Grow Better Crops," (Sep. 1, 2013) Scientific American. Retrieved from URL <https://www.scientificamerican.com/article/microbes-helpgrow-better-crops/>, (Year: 2013), 7 pages.

Contreras et al., "The product of the nitrogen fixation regulatory gene nfrX of Azotobacter vinelandii is functionally and structurally homologous to the uridylyltransferase encoded by glnD in enteric bacteria." J Bacterial. Dec. 1991, 173(24):7741-7749.

Costerton et al., Microbial Biofilms. Annu. Rev. Microbial., Oct. 1995, 49:711-745.

Crameri et al., "Molecular evolution of an arsenate detoxification pathway by DNA shuffling," Nat. Biotechnol., 1997, 15:436-438.

Crickmore et al., "Revision of the Nomenclature for the Bacillus thuringiensis Pesticidal Crystal Proteins," Microbiol Mol Biol Rev., Sep. 1998, 62(3):807-813.

Crook et al., "Re-engineering multicloning sites for function and convenience," Nucl. Acids Res., 2011, 39:e92, 10 pages.

Curatti et al., "Genes required for rapid expression of nitrogenase activity in Azotobacter vinelandii," PNAS, May 2005, 102(18):6291-6296.

(56) References Cited

OTHER PUBLICATIONS

Czar et al., "Gene synthesis demystified," Trends Biotechnol, 2009, 27(2):63-72.
Da Silva et al., Survival of endophytic bacteria in polymer-based inoculants and efficiency of their aplication to sugarcane/Plant Soil, May 2012, 356:231-243.
Dandekar et al., "Conservation of gene order: a fingerprint of proteins that physically interact," Trends Biochem. Sci., 1998, 23:324-328.
Das et al., "Microbial assay of N2 fixation rate, a simple alternate for acetylene reduction assay," MethodsX, 2018, 5:909-914.
Datsenko et al., "One-step inactivation of chromosomal genes in *Escherichia coli* K-12 using PCR products," PNAS, Jun. 2000, 97(12):6640-6645.
Davin-Regli et al., "Enterobacter aerogenes and Enterobacter cloacae; versatile bacterial pathogens confronting antibiotic treatment," Front Microbiol, 2015, 6:392, 10 pages.
De Bruijn et al., "The Cloning and characterization of the glnF (ntrA) Gene of Klebsiella pneumoniae: Role of glnF (ntrA) in the Regulation of Nitrogen Fixation (nif) and other Nitrogen assimilation genes," Mol. Genet., Aug. 1983, 192:342-353.
De Freitas, "Yield and N assimilation of winter wheat (*Triticum aestivum* L., var. Norstar) inoculated with rhizobacteria," Pedobiologia, Jan. 2000, 44(2):97-104.
De Raad et al., "A solid-phase platform for combinatorial and scarless multipart gene assembly," ACS Synth. Biol., 2013, 2:316-326.
Delmotte et al., An integrated proteomics and transcriptomics reference data set provides new insights into the Bradyrhizobium japonicum bacteroid metabolism in soybean root nodules. Proteomics. Apr. 2010;10(7):1391-400.
Desnoues et al., "Nitrogen fixation genetics and regulation in a Pseudomonas stutzeri strain associated with rice," Microbiology, May 2003, 149:2251-2262.
Dessaux et al., Engineering the Rhizosphere. Trends Plant Sci. Mar. 2016;21(3):266-278. doi: 10.1016/j.tplants.2016.01.002. Epub Jan. 23, 2016.
Dixon et al., "Genetic regulation of biological nitrogen fixation," Nature Reviews, Aug. 2004, 2:621-631.
Dixon et al., "Genetic transfer of nitrogen fixation from Klebsiella pneumoniae to *Escherichia coli*," Nature, 1972, 237(5350):102-103.
Dong et al., "Kinetics and Strain Specificity of Rhizosphere and Endophytic Colonization by Enteric Bacteria on Seedlings of Medicago sativa and Medicago truncatula," Appl Environ Microbial., Mar. 2003, 69(3):1783-1790.
Dos Santos et al., "Distribution of nitrogen fixation and nitrogenase-like sequences amongst microbial genomes," BMC Genomics, Dec. 2012, 13(1):162, 12 pages.
Du et al., "Customized optimization of metabolic pathways by combinatorial transcriptional engineering," Nucleic Acids Res., Oct. 2012, 40(18):e142, 10 pages.
Dunican et al., Genetic transfer of nitrogen fixation from Rhizobium trifolii to Klebsiella aerogenes. Biochem Biophys Res Commun. Mar. 15, 1974;57(1):62-72.
Dykxhoorn et al., "A set of compatible tac promoter expression vectors," Gene, 1996, 177(1-2):133-136.
Easter et al., "Role of the parCBA Operon of the Broad-Host-Range Plasmid RK2 in Stable Plasmid Maintenance," Journal Of Bacteriology, 1998, 180(22):6023-6030.
Edgar, Muscle: multiple sequence alignment with high accuracy and high throughput. Nucleic Acids Res. Mar. 19, 2004;32(5):1792-7.
Egener et al., "Identification of NifL-like protein in a diazotroph of the b-subgroup of the proteobacteria, *Azoarcus* sp. strain BH72," Microbiology, Oct. 2002, 148(10):3203-3212.
Endy et al., "Foundations for engineering biology," Nature, 2005, 438:449-453.
Enkh-Amgalan et al., "Molecular evolution of the nif gene cluster carrying nifl1 and nifl2 genes in the Gram-positive phototrophic bacterium Heliobacterium chlorum," International Journal of Systematic and Evolutionary Microbiology, 2006, 56:65-74.
Estrem et al., "Identification of an UP element consensus sequence for bacterial promoters," PNAS, 1998, 95(11):9761-9766.
Eyraud et al., "Expression and Biological Activity of the Cystine Knot Bioinsecticide PA1b (Pea Albumin 1 Subunit b)," PLOS One, Dec. 2013, 8(12):e81619, 9 pages.
Fani et al., "Molecular evolution of nitrogen fixation: the evolutionary history of the niID, nifK, nifE, and nifN gene," J Mol Evol., 2000, 51(1):1-11.
Feher et al. "In the fast lane: large-scale bacterial genome engineering," J Biotechnol., Jul. 2012, 160(1-2):72-9.
Ferri et al., Plasmid electroporation of Sinorhizobium strains: The role of the restriction gene hsdR in type strain Rm1021. Plasmid. May 2010;63(3):128-35. doi: 10.1016/j.plasmid.2010.01.001. Epub Jan. 22, 2010.
Ferrières et al., "The yjbEFGH locus in *Escherichia coli* K-12 is an operon encoding proteins involved in exopolysaccharide production," Microbiology, Apr. 2007, 153(Pt 4):1070-80.
Fischbach et al., "The evolution of gene collectives: how natural selection drives chemical innovation," Proc. Natl. Acad. Sci. USA, 2008, 105:4601-4608.
Fontana et al., "RNA folding and combinatory landscapes," Phys. Rev. E., 1993, 47:2083-2099.
Forner et al., "Treatment of hepatocellular carcinoma," Crit Rev Oncol Hematol., Nov. 2006, 60(2):89-98.
Gaby et al., "A comprehensive aligned nifH gene database: a multipurpose tool for studies of nitrogen-fixing bacteria," Database, 2014, 2014:bau001, 8 pages.
Gamer et al., "A T7 RNA polymerase-dependent gene expression system for Bacillus megaterium," Appl Micro Biol Biotechnol., Apr. 2009, 82(6):1195-203.
Gebeyehu et al., "Novel biotinylated nucleotide-analogs for labeling and colorimetric detection of DNA," Nucl. Acids Res., 1987, 15:4513, 22 pages.
Geddes et al., Use of plant colonizing bacteria as chassis for transfer of N2-fixation to cereals. Curr Opin Biotechnol. Apr. 2015;32:216-222. doi: 10.1016/j.copbio.2015.01.004. Epub Jan. 24, 2015.
GenBank Accession No. CP007215.3, "Kosakonia sacchari SP1 chromosome, complete genome," Sep. 19, 2017, 729 pages.
Georg et al., "cis-antisense RNA, another level of gene regulation in bacteria," Microbiol Mol Biol Rev, 2011, 75(2):286-300.
Gibson et al., "Chemical synthesis of the mouse mitochondrial genome," Nat. Methods, 2010, 7:901-903.
Gibson et al., "Enzymatic assembly of DNA molecules up to several hundred kilobases," Nat Methods, 2009, 6(5):343-345.
Gibson, "Physical Environment and Symbiotic Nitrogen Fixation," Australian Journal of Biological Sciences, 1963, 16(1):28-42.
Gorochowski et al., Genetic circuit characterization and debugging using RNA-seq. Mol Syst Biol. Nov. 9, 2017;13(11):952.
Gosink et al., "The product of the Klebsiella pneumoniae nifX gene is a negative regulator of the nitrogen fixation (nit) regulon," J Bacteriology, 1990, 172(3):1441-1447.
Gossen et al., "Tight control of gene expression in mammalian cells by tetracycline-responsive promoters," PNAS USA, 1992, 89(12):5547-5551.
Gossen et al., "Transcriptional activation by tetracyclines in mammalian cells," Science, 1995, 268(5218):1766-1769.
Gottelt et al., "Deletion of a regulatory gene within the cpk gene cluster reveals novel antibacterial activity in Streptomyces coelicolor A3(2)," Microbiology, 2010, 156:2343-2353.
Govantes et al., "Mechanism of coordinated synthesis of the antagonistic regulatory proteins NifL and NifA of Klebsiella pneumoniae," J Bacterial. Dec. 1996, 178(23):6817-6823.
Guell et al., "Bacterial transcriptomics: what is beyond the RNA horiz-ome?," Nature reviews Microbiology, 2011, 9(9):658-669.
Guell et al., "Transcriptome complexity in a genome-reduced bacterium," Science, 2009, 326:1268-1271.
Guo et al., "Discovery of Reactive Microbiota-Derived Metabolites that Inhibit Host Proteases," Cell, Jan. 2017, 168(3):517-526, e18.
Gutierrez-Zamora et al., Natural endophytic association between Rhizobium etli and maize (*Zea mays* L.). J Biotechnol. Oct. 4, 2001;91(2-3):117-26.

(56) References Cited

OTHER PUBLICATIONS

Haapalainen et al., "Soluble plant cell signals induce the expression of the type III secretion system of Pseudomonas syringae and upregulate the production of pilus protein HrpA," Mol. Plant Microbe Interact., 2009, 22:282-290.

Hale et al., "An efficient stress-free strategy to displace stable bacterial plasmids," BioTechniques, Mar. 2010, 48:223-228.

Hansal et al., "Cutting Edge: Induction of antigen-specific hyporesponsiveness by transplantation of hemopoietic cells containing an MHC class I transgene regulated by a lymphocyte-specific promoter," J Immunol., Aug. 1998, 161(3):1063-8.

Harvey et al., "Inducible control of gene expression: prospects for gene therapy," Curr Opin Chem Biol., Aug. 1998, 2(4):512-8.

Herlache et al., "Characterization of the Agrobacterium vitis pehA gene and comparison of the encoded polygalacturonase with the homologous enzymes from Erwinia carotovora and Ralstonia solanacearum," Appl Environ Microbial., Jan. 1997, 63(1):338-346.

Hernandez et al., "Biochemical analysis of the recombinant Fur (ferric uptake regulator) protein from Anabaena PCC 7119: factors affecting its oligomerization state," Biochem J., 2002, 366:315-322.

Hoeschle-Zeledon et al., Regulatory challenges for biological control. The CGIAR Systemwide Program on Integrated Pest Management, Jan. 2013, SP-IPM Secretariat, International Institute Tropical Agriculture (IITA), Ibadan, Nigeria, 53 pages.

Holden et al., "Colonization outwith the colon: plants as an alternative environmental reservoir for human pathogenic enterobacteria," FEMS Microbiol. Rev., 2009, 33:689-703.

Hoover et al., Homocitrate is a component of the iron-molybdenum cofactor of nitrogenase. Biochemistry. Apr. 4, 1989;28(7):2768-71.

Hu et al., "Assembly of nitrogenase MoFe protein," Biochemistry, 2008, 47(13):3973-3981.

Hunter, "'Genetically Modified Lite' placates public but not activists," EMBO Reports, Jan. 2014, 15(2):138-141.

Huynen et al., "Smoothness within ruggedness: the role of neutrality in adaptation," Proc. Natl. Acad. Sci. USA, 1996, 93:397-401.

Iber, "A quantitative study of the benefits of co-regulation using the spoIIA operon as an example," Mol. Sys. Biol., 2006, 2:1-6.

Idalia et al., "*Escherichia coli* as a model organism and its application in biotechnology," Recent Advances on Physiology, Pathogenesis, and Biotechnological Applications, Chapter 13, 2017, pp. 253-274.

Igiehon et al., Rhizosphere Microbiome Modulators: Contributions of Nitrogen Fixing Bacteria towards Sustainable Agriculture. Int J Environ Res Public Health. Mar. 23, 2018;15(4):574.

Ishihama, "Prokaryotic genome regulation: multifactor promoters, multitarget regulators and hierarchic networks," FEMS Microbial Rev, 2010, 34(5):628-645.

Ivanova et al., "Artificial Regulation of Genes, Of the coding proteins of the nitrogenase complex Rhizobial bacteria," Natural Sciences, 2014, 13(174):36-39 (Machine Translation).

Izquierdo et al., "Distribution of Extensive nifH Gene Diversity Across Physical Soil Microenvironments," Microbial Ecology, 2006, 51(4):441-452.

Jacob et al., "Solid-state NMR studies of Klebsiella pneumoniae grown under nitrogen-fixing conditions," J Biol Chem, 1987, 262(1):254-259.

Jacoby et al., "The Role of Soil Microorganisms in Plant Mineral Nutrition-Current Knowledge and Future Directions," Frontiers in Plant Scients, 2017, 8(19):1-19.

Jahn et al., Extraction of Extracellular Polymeric Substances (EPS) from Biofilms Using a Cation Exchange Resin. Wat. Sci. Tech., 1995, 32(8):157-164.

Janczarek et al., "Multiple copies of rosR and pssA genes enhance exopolysaccharide production, symbiotic competitiveness and clover nodulation in Rhizobium leguminosarum bv. *trifolii*," Antonie Van Leeuwenhoek, Nov. 2009, 96(4):471-86.

Jaschke et al., "A fully decompressed synthetic bacteriophage 0X174 genome assembled and archived in yeast," Virology, 2012, 434:278-284.

Jensen, "The *Escherichia coli* K-12 "wild types" W3110 and MG1655 have an rph frameshift mutation that leads to pyrimidine starvation due to low pyre expression levels," J. Bacteriol., 1993, 175:3401-3407.

Johnson et al., "Properties of overlapping genes are conserved across microbial genomes," Genome Res, 2004, 14(11):2268-2272.

Joseph et al., "Recent developments of the synthetic biology toolkit for Clostridum," Frontiers in microbology, 2018, 9(154):1-13.

Kabaluk et al., The use and regulation of microbial pesticides in representative jurisdictions Worldwide. IOBC Global, 2010, 99 pages.

Kalir et al., "Ordering genes in a flagella pathway by analysis of expression kinetics from living bacteria," Science, 2001, 292(5524):2080-2083.

Kaneko et al., "Complete genomic structure of the cultivated rice endophyte *Azospirillum* sp. B510," DNA Res., 2010, 17:37-50.

Kant et al., "Understanding plant response to nitrogen limitation for the improvement of crop nitrogen use efficiency," Journal of Experimental Botany, 2011, 62(4):1499-1509.

Karlin et al., "Applications and statistics for multiple high-scoring segments in molecular sequences," Proc Natl Acad Sci USA, Jun. 1993, 90(12):5873-7.

Karlin et al., "Methods for assessing the statistical significance of molecular sequence features by using general scoring schemes," Proc Natl Acad Sci USA, Mar. 1990, 87(6):2264-8.

Katsnelson, "Engineered bacteria could boost corn yields: Gene-edited microbe offer continuous nitrogen fixation," Chemical & Engineering News, Dec. 28, 2021, retrieved from URL https://cen.acs.org/food/agriculture/Engineered-bacteria-boost-corn-yields/99/web/2021/12>, 3 pages.

Kececiglu et al., "Of mice and men: Algorithms for evolutionary distances between genomes with translocation," SODA: Proceedings of the sixth annual ACM-SIAM symposium on Discrete algorithms, 1995, 10 pages.

Kechris et al., Quantitative exploration of the occurrence of lateral gene transfer by using nitrogen fixation genes as a case study. Proc Natl Acad Sci U S A. Jun. 20, 2006;103(25):9584-9. doi: 10.1073/pnas.0603534103. Epub Jun. 12, 2006.

Kelly et al., "Measuring the activity of BioBrick promoters using an in vivo reference standard," J Biol Eng, 2009, 3:4, 13 pages.

Kerby et al., "Photoproduction of ammonium by immobilized mutant strains of Anabaena variabilis," Applied Microbiology and Biotechnology, Apr. 1986, 24(1):42-46.

Kim et al., "A 20 nucleotide upstream element is essential for the nopaline synthase (nos) promoter activity," Plant Mol Biol., Jan. 1994, 24(1):105-17.

Kim et al., "Constitutive expression of nitrogenase system in Klebsiella oxytoca by gene targeting mutation to the chromosomal nifLA operon," Journal of Biotechnology, Jun. 1989, 10(3-4):293-301.

King et al., "Spider-Venom Peptides: Structure, Pharmacology, and Potential for Control of Insect Pests," Annu. Rev. Entomol., 2013, 58:475-96.

Kingsford et al., "Rapid, accurate, computational discovery of Rho-independent transcription terminators illuminates their relationship to DNA uptake," Genome Bio. 2007, 8(2):R22, 12 pages.

Kitano, "Systems biology: a brief overview," Science, 2002, 295(5560): 1662-1664.

Klose et al., "Glutamate at the site of phosphorylation of nitrogen-regulatory protein NTRC mimics aspartyl-phosphate and activates the protein," J Mol Biol., Jul. 1993, 232(1):67-78.

Knight, "Idempotent Vector Design for Standard Assembly of Biobricks," MIT Artificial Intelligence Laboratory, The TTL Data Book for Design Engineers, 2003, 11 pages.

Kornberg, "DNA Replication," W. H. Freeman & Co., San Francisco, 1980, pp. 75-77.

Kovacs et al., "Stochasticity in protein levels drives colinearity of gene order in metabolic operons of *Escherichia coli*," PLoS Biol, 2009, 7(5):e1000115, 9 pages.

Kranz et al., "Ammonia-constitutive nitrogen fixation mutants of Rhodobacter capsulatus," Gene, Nov. 1988, 71(1):65-74.

(56) References Cited

OTHER PUBLICATIONS

Kumar et al., "Metabolic regulation of *Escherichia coli* and its gdhA, glnL, gltB, D mutants under different carbon and nitrogen limitations in the continuous culture," Microbial Cell Factories, Jan. 2010, 9(8):1-17.
Kutter et al., "Colonization of barley (*Hordeum vulgare*) with *Salmonella enterica* and *Listeria* spp," FEMS Microbial. Ecol., 2006, 56, 262-271.
Lauritsen et al., "A versatile one-step CRISPR-Cas9 based approach to plasmid-curing." Microb Cell Fact, 2017, 16(135):1-10.
Lenski et al., "Effects of Segregation and Selection on Instability of Plasmid pACYC184 in *Escherichia coli* B," Journal of Bacteriology, Nov. 1987, 169(11):5314-5316.
Levican et al., "Comparative genomic analysis of carbon and nitrogen assimilation mechanisms in three indigenous bioleaching bacteria: predictions and validations," BMC Genomics, 2008, 9:581, 19 pages.
Levin-Karp et al., "Quantifying translational coupling in *E. coli* synthetic operons using RBS modulation and fluorescent reporters," ACS Synth. Biol., 2013, 2:327-336.
Li et al., Using synthetic biology to increase nitrogenase activity. Microb Cell Fact. Feb. 20, 2016;15:43.
Li et al., "Human Enhancers Are Fragile and Prone to Deactivating Mutations," Mol Biol Evol., Aug. 2015, 32(8):2161-80.
Li et al., The anti-Shine-Dalgarno sequence drives translational pausing and codon choice in bacteria. Nature. Mar. 28, 2012;484(7395):538-41.
Liang et al., "Minimal effect of gene clustering on expression in *Escherichia coli*," Genetics, Feb. 2013, 193(2):453-65.
Lifesci.sussex.ac.uk, [online], "Bacillus thuringiensis Toxin Nomenclature," 2016, retrieved on Mar. 25, 2021, retrieved from URL<www.lifesci.sussex.ac.uk/home/Neil_Crickmore/Bt/> 1 page.
Lin et al., "PC, a Novel Oral Insecticidal Toxin from Bacillus bombysepticus Involved in Host Lethality via APN and BtR-175," Scientific Reports, Jun. 2015, 5:11101, 14 pages.
Liu et al., "Phenazine-1-carboxylic acid biosynthesis in Pseudomonas Chlororaphis GP72 is positively regulated by the sigma factor RpoN," World Journal of Microbiology and Biotechnology, Jan. 2008, 24(9):1961-1966.
Liu et al., "Whole genome analysis of halotolerant and alkalotolerant plant growth-promoting rhizobacterium *Klebsiella* sp. D5A," Sci Rep., May 2016, 6:1-10.
Lombo et al., "The mithramycin gene cluster of Streptomyces argillaceus contains a positive regulatory gene and two repeated DNA sequences that are located at both ends of the cluster," J. Bacteriol., 1999, 181:642-647.
Lowman et al., Strategies for enhancement of switchgrass (*Panicum virgatum* L.) performance under limited nitrogen supply based on utilization of N-fixing bacterial endophytes. Plant and Soil, Aug. 2016, 405(1):47-63, 17 pages.
Lucks et al., "Toward scalable parts families for predictable design of biological circuits," Curr. Opin. Microbiol., 2008, 11:567-573.
Ma et al., "Effect of nicotine from tobacco root exudates on chemotaxis, growth, biocontrol efficiency, and colonization byPseudomonas aeruginosaNXHG29," Antonie van Leeuwenhoek, 2018, 111(7):1237-1257.
Mabrouk et al., "Chapter 6: Potential of Rhizobia in Improving Nitrogen Fixation and Yields of Legumes," Symbiosis, May 30, 2018, IntechOpen, pp. 1-16, retrieved on Jan. 12, 2021, retrieved from URL<https://www.intechopen.com/books/symbiosis/potential-of-rhizobia-in-improving- B351nitrogen-fixation-and-yields-of-legumes> 2 pages, Abstract.
MacNeil et al., "Fine-structure mapping and complementation analysis of nif (nitrogen fixation) genes in Klebsiella pneumoniae," J Bacteriol. Oct. 1978, 136(1):253-266.
MacNeil et al., "Mutations in nif genes that cause Klebsiella pneumoniae to be derepressed for nitrogenase synthesis in the presence of ammonium," J Bacteriol, Nov. 1980, 144(2):744-751.
Maduro, "Random DNA Generator," retrieved from URL <http://www.faculty.ucr.edu/~mmaduro/random.htm>, 2011, 1 page.

Magari et al., "Pharmacologic control of a humanized gene therapy system implanted into nude mice," J Clin Invest., Dec. 1997, 100(11):2865-2872.
Magasanik, "Genetic control of nitrogen assimilation in bacteria," Ann. Rev. Genet, 1982, 16:135-68.
Mahmood et al., Seed biopriming with plant growth promoting rhizobacteria: a review. FEMS Microbiol Ecol Aug. 2016; 92(8): fiw112.
Malik et al., Association of nitrogen-fixing, plant-growth-promoting rhizobacteria (PGPR) with kallar grass and rice. Plant and Soil. 1997; 194: 37-44.
Mandal et al., "Gene regulation by riboswitches," Nat Rev Mol Cell Biol, 2004, 5(6):451-463.
Mao et al., Silencing a cotton bollworm P450 monooxygenase gene by plant-mediated RNAi impairs larval tolerance of gossypol. Nature Biotechnology, Nov. 2007, 25(11): 1307-1313.
Martinelli et al., "Structure-function studies on jaburetox, a recombinant insecticidal peptide derived from jack bean (*Canavalia ensiformis*) urease," Biochimica et Biophysica Acta, Mar. 2014, 1840(3):935-44.
Marx et al., "Broad-host-range ere-lox system for antibiotic marker recycling in gram-negative bacteria," Biotechniques, Nov. 2002, 33(5):1062-7.
Masepohl et al., "Organization and regulation of genes encoding the molybdenum nitrogenase and the alternative nitrogenase in Rhodobacter capsulatus," Arch. Microbial., Sep. 1996, 165:80-90.
Mason et al., "Cryptic Growth in Klebsiella-Pneumoniae," Appl Microbiol Biot, 1987, 25(6):577-584.
Matsubayashi et al., "Peptide hormones in plants," Annu Rev Plant Biol., 2006, 57:649-74.
Medema et al., "Exploiting plug-and-play synthetic biology for drug discovery and production in microorganisms," Nat. Rev. Microbiol., 2011, 9:131-137.
Mirzahoseini et al., "Heterologous Proteins Production in *Escherichia coli*: An Investigation on the Effect of Codon Usage and Expression Host Optimization," Cell Journal (Yakhteh), Dec. 2011, 12(4):453, 7 pages.
Mitra, "Regulation of nifLA operon in Azotobacter vinelandii," Thesis submitted to the Jawaharlal Nehru University, New Delhi, for the degree of doctor of philosophy, 2000, 153 pages.
Miyazaki, "Creating random mutagenesis libraries by megaprimer PCR of whole plasmid (Mega Whop)," Methods Mol Biol, 2003, 231:23-28.
Moon et al., "Genetic programs constructedfrom layered logic gates in single cells," Nature, Nov. 2012, 491(7423):249-53.
Mueller et al., "Closing yield gaps through nutrient and water management," Nature, 2012, 490:254-257.
Mus et al., "Diazotrophic Growth Allows Azotobacter vinelandii To Overcome the Deleterious Effects of a glnE Deletion," Appl Environ Microbiol., Jun. 2017, 83(13):e00808-17.
Mus et al., "Symbiotic Nitrogen Fixation and the Challenges to Its Extension to Nonlegumes," Appl Environ Microbial., Jul. 2016, 82(13):3698-3710.
Muse et al., "The nac (Nitrogen Assimilation Control) Gene from *Escherichia coli*," J Bacteriology, Mar. 1998, 180(5):1166-1173.
Mutalik et al., "Quantitative estimation of activity and quality for collections of functional genetic elements," Nat. Methods, 2013, 10:347-353.
Nagy et al., Nanofibrous solid dosage form of living bacteria prepared by electrospinning. eXPRESS Polymer Letters, 2014, 8(5):352-361.
Naimov et al., "Solubilization, Activation, and Insecticidal Activity of Bacillus thuringiensis Serovar thompsoni HD542 Crystal Proteins," Applied and Environmental Microbiology, Dec. 2008, 74(23):7145-7151.
Nassar et al., "Promotion of plant growth by an auxin-producing isolate of the yeast *Williopsis saturnus* endophytic in maize (*Zea mays* L.) roots," Biology and Fertility of Soils, 2005, 42:97-108.
Nature.com, [online], "Transcription Unit," 2005, retrieved on Apr. 15, 2021, retrieved from URL<https://www.nature.com/scitable/definition/transcription-unit-260>, 2 pages.
Nelissen et al., "Translational research:from pot to plot," Plant Biotechnology Journal, Jan. 2014, 12:277-285.

(56) References Cited

OTHER PUBLICATIONS

Nestmann, "Mutagenesis by nitrosoguanidine, ethyl methanesulfonate, and mutator gene mutH in continuous cultures of *Escherichia coli*," Science Direct, Jun. 1975, 28(3):323-330.
Nichkawade, "Studies on upstream regulatory sequence of the nifLA promoter of Klebsiella pnuemoniae," Thesis submitted to the Jawaharlal Nehru University, New Delhi, for the degree of doctor of philosophy, 1996, 166 pages.
Nielsen et al., Conceptual model for production and composition of exopolymers in biofilms. Wat. Sci. Tech., 1997, 36(1): 11-19.
Nielsen et al., Extraction of EPS. Wingender et al. (eds.), Microbial Extracellular Polymeric Substances, 1999, 24 pages.
Nielsen, "Transgenic organisms—time for conceptual diversification? ," Nature Biotechnology, 2003, 21:227-228.
No et al., "Ecdysone-inducible gene expression in mammalian cells and transgenic mice," Proc. Natl. Acad. Sci. USA, Apr. 1996, 93(8):3346-3351.
No et al., Ecdysone-inducible gene expression in mammalian cells and transgenic mice. Proc Natl Acad Sci U S A. Apr. 16, 1996;93(8):3346-51.
Noskov et al., "Assembly of large, high G+C bacterial DNA fragments in yeast," ACS Synth. Biol., 2012, 1:267-273.
Oh et al., "Organization of nif gene cluster in *Frankia* sp. EuIK1 strain, a symbiont of Elaeagnus umbellata," Arch. Microbiol., 2012, 194:29-34.
Ohtsuka et al., "An alternative approach to deoxyoligonucleotides as hybridization probes by insertion of deoxyinosine at ambiguous codon positions," J. Biol. Chem., 1985, 260:2605-2608.
Okubo et al., "Effects of Elevated Carbon Dioxide, Elevated Temperature, and Rice Growth Stage on the Community Structure of Rice Root-Associated Bacteria," Microbes Environ., Jun. 2014, 29(2):184-190.
Orme-Johnson, "Molecular basis of biological nitrogen fixation," Annu Rev Biophys Biophys Chem, 1985, 14:419-459.
Ortiz-Marquez et al., "Association with an Ammonium-excreting bacterium allows diazotrophic culture of oil-rich Eukaryotic microalgae," Appl. Microbial., 2012, 78(7):2345-2352.
Pakula et al., "Genetic analysis of protein stability and function," Annu Rev Genet, 1989, 23:289-310.
Parker et al., "Pore-forming protein toxins: from structure to function," Progress in Biophysics & Molecular Biology, 2005, 88:91-142.
Pascuan et al., Exploring the Ancestral Mechanisms of Regulation of Horizontally Acquired Nitrogenases. J Mol Evol. Oct. 2015;81(3-4):84-9. doi: 10.1007/s00239-015-9698-4. Epub Sep. 15, 2015.
Patil et al., Liquid formulations of Acetobacter diazotrophicus L 1 and Herbaspirillum seropedicae J24 and their field trials on wheat. International J Environmental Science, 2012, 3(3):1116-1129, 4 pages (Abstract Only).
Perrine-Walker et al., Infection process and the interaction of rice roots with rhizobia. J Exp Bot. 2007;58(12):3343-50. doi: 10.1093/jxb/erm181. Epub Oct. 8, 2007.
Pfleger et al., "Combinatorial engineering of intergenic regions in operons tunes expression of multiple genes," Nature Biotechnology, 2006, 24(8):1027-1031.
Philippe et al., "Improvement of pCVD442, a suicide plasmid for gene allele exchange in bacteria," Plasmid, 2004, 51(3):246-255.
Piccioli et al. "Neuroantibodies: ectopic expression of a recombinant anti-substance P antibody in the central nervous system of transgenic mice," Neuron., Aug. 1995, 15(2):373-84.
Piccioli et al., "Neuroantibodies: molecular cloning of a monoclonal antibody against substance P for expression in the central nervous system," Proc Natl Acad Sci USA, Jul. 1991, 88(13):5611-5615.
Pickens et al., "Metabolic engineering for the production of natural products," Annu. Rev. Chem. Biomol. Eng., 2011, 2:211-236.
Plotnikova et al., "Pathogenesis of the human opportunistic pathogen Pseudomonas aeruginosa PA14 in *Arabidopsis*," Plant Physiol., 2000, 124:1766-1774.

Poliner et al., "Nontransgenic Marker-Free Gene Disruption by an Episomal CRISPR System in the Oleaginous Microalga, Nannochloropsis oceanica CCMP1779," ACS Synth. Biol., 2018, 7(4):962-968.
Price et al., "Operon formation is driven by coregulation and not by horizontal gene transfer," Genome Res., 2005, 15:809-819.
Price et al., "The life-cycle of operons," PLoS Genet., 2006, 2:e96, 15 pages.
Purcell et al., "Cholesterol oxidase: a potent insecticidal protein active against boll weevil larvae," Biochem Biophys Res Commun, Nov. 1993, 196(3):1406-13.
Purnick et al., "The second wave of synthetic biology: from modules to systems," Nat Rev Mol Cell Biol, 2009, 10(6):410-422.
Pyne et al., "Coupling the CRISPR/Cas9 System with Lambda Red Recombineering Enables Simplified Chromosomal Gene Replacement in *Escherichia coli*," Applied and Environmental Microbioloy, Aug. 2015, 81(15):5103-5144.
Qaim et al., "Yield Effects of Genetically Modified Crops in Developing Countries," Science, Feb. 2003, 299(5608):900-2.
Qiu et al., "Construction of genetically engineered strains of Enterobacter cloacae (nifl~(-)A~(c))," Acta Phytophysiologica Sinica, Jan. 1999, 25(3):269-273.
Rakhee et al., Extracellular polymeric substances of the marine fouling diatom amphora rostrata Wm.Sm. Biofouling, 2001, 17(2):117-127, 12 pages.
Ramirez et al., "Burkholderia and Paraburkholderia are Predominant Soybean Rhizobial Genera in Venezuelan Soils in Different Climatic and Topographical Regions," Microbes and Environments, Mar. 2019, 34(1):43-58.
Ramon et al., "Single-step linker-based combinatorial assembly of promoter and gene cassettes for pathway engineering," Biotechnol. Lett., 2011, 33:549-555.
Ran et al., "Genome erosion in a nitrogen-fixing vertically transmitted endosymbiotic multicellular cyanobacterium," PLoS One, Jul. 2010, 5(7):e11486, 11 pages.
Resendis-Antonio et al., "Systems biology of bacterial nitrogen fixation: High-throughput technology and its integrative description with constraint-based modeling," BMC Syst Biol., 2011, 5:120, 15 pages.
Riedel et al., "Nitrogen fixation by Klebsiella pneumoniae is inhibited by certain multicopy hybrid nif plasmids," J Bacterial, 1983, 153(1):45-56.
Roberts et al., "Regulation and characterization of protein products coded by the nif (nitrogen fixation) genes of Klebsiella pneumoniae," J Bacterial., Oct. 1978, 136(1): 267-279.
Robledo et al., "Rhizobium cellulase CelC2 is essential for primary symbiotic infection of legume host roots," Proc Natl Acad Sci USA, May 2008, 105(19):7064-9.
Robledo et al., "Role of Rhizobium endoglucanase CelC2 in cellulose biosynthesis and biofilm formation on plant roots and abiotic surfaces," Microb Cell Fact., Sep. 2012, 11:125, 12 pages.
Robson et al., 2015. Azotobacter Genomes: The Genome of Azotobacter chroococcum NCIMB 8003 (ATCC 4412). PLoS ONE. 10(6): e0127997.
Rojas-Tapias et al., Preservation of Azotobacter chroococcum vegetative cells in dry polymers. Univ. Sci., 2015, 20(2):201-207.
Rommens et al., "Intergeneric transfer and functional expression of the tomato disease resistance gene PTO," Plant Cell, Oct. 1995, 7(10):1537-1544.
Roncato-Maccari et al., "Endophytic Herbaspirillum seropedicae expresses nif genes in gramineous plants," FEMS Microbiology Ecology, 2003, 45:39-47.
Rong et al., "Promoter specificity determinants of T7 RNA polymerase," Proc. Natl. Acad. Sci. USA, 1998, 95(2):515-519.
Rossolini et al., "Use of Deoxyinosine-Containing Primers vs Degenerate Primers for Polymerase Chain Reaction Based on Ambiguous Sequence Information," Mol. Cell. Probes, 1994, 8:91-98.
Rubio et al., "Maturation of Nitrogenase: a Biochemical Puzzle," J. Bacteriology, 2005, 187(2):405-414.
Ryu et al., Control of nitrogen fixation in bacteria that associate with cereals. Nat. Microbiol., Feb. 2020, 5(2):314-330, 31 pages.

(56) References Cited

OTHER PUBLICATIONS

Saleh et al., "Involvement of gacS and rpoS in enhancement of the plant growth-promoting capabilities of Enterobacter cloacae CAL2 and UW4," Canadian Journal of Microbiology, Aug. 2001, 47(8):698-705.
Salis et al., "Automated design of synthetic ribosome binding sites to control protein expression," Nat Biotechnol, 2009, 27(10):946-950.
Sanahuja et al., "Bacillus thuringiensis: a century of research, development and commercial applications," Plant Biotechnology Journal, Apr. 2011, 9(3):283-300.
Sandoval et al., "Strategy for directing combinatorial genome engineering in *Escherichia coli*," Proc Natl Acad Sci USA, Jun. 2012, 109(26):10540-5.
Santi et al., "Biological nitrogen fixation in non-legume plants," Annals of Botany, Jan. 2013, 111:743-767.
Sanyal et al., "The etiology of hepatocellular carcinoma and consequences for treatment," Oncologist, 2010, 15(Suppl 4):14-22.
Schmidt-Dannert et al., "Molecular breeding of carotenoid biosynthetic pathways," Nat. Biotechnol., 2000, 18:750-753.
Schmitz et al., "Iron is required to relieve inhibitory effects on Nifl on transcriptional activation by NifA in Klebsiella pneumoniae," J Bacterial, Aug. 1996, 178(15):4679-4687.
Schouten et al., "Do cisgenic plants warrant less stringent oversight? ," Nature Biotechnology, Jul. 2006, 24(7):753.
Schuler et al., "Insect-resistant transgenic plants," Trends in Biotechnology, Apr. 1998, 16(4):168-175.
Schuler et al., Potential side effects of insect-resistant transgenic plants on arthropod natural Enemies. Trends Biotechnol., May 1999, 17(5):210-216.
Service, "Genetically engineered microbes make their own fertilizer, could feed the world's poorest," Science, Apr. 2017, 2 pages.
Setten et al., "Engineering Pseudomonas protegens Pf-5 for Nitrogen Fixation and its application to improve plant growth under nitrogen-deficient conditions," PLOS One, 2013, 8(5):1-14.
Shanks et al., *Saccharomyces cerevisiae*-based molecular tool kit for manipulation of genes from gram-negative bacteria. Appl Environ Microbiol. Jul. 2006;72(7):5027-36.
Shetty et al., "Engineering BioBrick vectors from BioBrick parts," J Biol Eng, 2008, 2:5, 12 pages.
Sibold et al., "A nif mutant of Klebsiella pneumoniae fixing nitrogen in the presence of ammonia," FEMS Microbiology Letters, Jan. 1981, 10(1):37-41.
Sibold et al., "Constitutive expression of nitrogen fixation (nif) genes of Klebsiella pneumoniae due to a DNA duplication," EMBO J., 1982, 1(12):1551-8.
Siddavattam et al., "Regulation of nif Gene expression in Enterobacter agglomerans: Nucleotide sequence of the nifLA operon and influence of temperature and ammonium on its transcription," Molecular and general genetics, Dec. 1995, 249(6):629-636.
Simon et al., "Perturbation of niff expression in Klebsiella pneumoniae has limited effect on nitrogen fixation," J Bacteriol, 1996, 178(10):2975-2977.
Singer et al., "Genes and Genomes," Moscow: Mir, 1998, 1:33, 4 pages (with machine translation).
Singh et al., "An L-methionine-D,L-sulfoximine-resistant mutant of the cyanobacterium Nostoc muscorum showing inhibitor-resistant y-glutamyl-transferase, defective glutamine synthetase and producing extracellular ammonia during N2 fixation," FESS Letters, Apr. 1983, 154(1):10-14.
Sivaraman et al., "Codon choice in genes depends on flanking sequence information-implications for theoretical reverse translation," Nucleic Acids Res, 2008, 36(3):e16, 8 pages.
Sleight et al., "Randomized BioBrick assembly: a novel DNA assembly method for randomizing and optimizing genetic circuits and metabolic pathways," ACS Synth. Biol., 2013, 2(9):506-518.
Smanski et al., "Engineered Streptomyces platensis strains that overproduce antibiotics platensimycin and platencin," Antimicrob. Agents Chemother., 2009, 53:1299-12304.
Sorek et al., "Prokaryotic transcriptomics: a new view on regulation, physiology, and pathogenicity," Nat. Rev. Genet., 2010, 11:9-16.
Souza et al., "The N-Terminus of the NIFA protein of herbaspirillum seropedicae is probably involved in sensing of ammonia," In Tikhonovich et al. (Eds.) Proceedings of the 10th International Congress on Nitrogen Fixation, St. Petersburg, Russia, May 28-Jun. 3, 1995 (p. 260) Dordrecht: Kluwer.
Spiller et al., "Isolation and characterization of nitrogenase-derepressed mutant strains of cyanobacterium *Anabaena variabilis*," J Bacteriol. Feb. 1986, 165(2):412-419.
Staron et al., "The Third Pillar of Bacterial Signal Transduction: Classification of the Extracytoplasmic Function (ECF) Sigma Factor Protein Family," Mol Microbiol, 2009, 14(3):557-81.
Steenhoudt et al., "Azospirillum, a free-living nitrogen-fixing bacterium closely associated with grasses: genetic, biochemical and ecological aspects," FEMS Microbial. Rev., 2000, 24:487-506.
Stein et al., "The osteocalcin gene: a model for multiple parameters of skeletal-specific transcriptional control," Mol Biol Rep., Aug. 1997, 24(3):185-96.
Stemmer, "DNA shuffling by random fragmentation and reassembly: In vitro recombination for molecular evolution," Proc. Natl. Acad. Sci. USA, Oct. 1994, 91:10747-10751.
Stephanopoulos, "Challenges in engineering microbes for biofuels production," Science, Feb. 2007, 315(5813):801-4.
Stewart et al., "In situ studies on nitrogen fixation with the acetylene reduction technique," Science, 1967, 158(3800):536.
Stucken et al., "The smallest known genomes of multicellular and toxic cyanobacteria: comparison, minimal gene sets for linked traits and the evolutionary implications," PLoS ONE, 2010, 5:e9235, 15 pages.
Subtil et al., "Secretion of Predicted Inc Proteins of Chlamydia pneumoniae by a Heterologous Type III Machinery," Molecular Microbiology, Feb. 2001, 39(3):792-800.
Suh et al., "Functional expression of the FeMo-cofactor-specific biosynthetic genes nifEN as a NifE-N fusion protein synthesizing unit in Azotobacter vinelandii," Biochem. Biophys. Res. Comm., 2002, 299:233-240.
Suzuki et al., "Immune-mediated motor polyneuropathy after hematopoietic stem cell transplantation," Bone Marrow Transplant., Aug. 2007, 40(3):289-91.
Swain et al., "Nitrogen fixation and its improvement through genetic engineering," J. Global Biosciences, 2013, 2(5): 98-112.
Tamsir et al., "Robust multicellular computing using genetically encoded NOR gates and chemical 'wires'," Nature, 2011, 469(7329):212-215.
Tan, "A synthetic biology challenge: making cells compute," Mol Biosyst, 2007, 3:343-353.
Temme et al., "Induction and relaxation dynamics of the regulatory network controlling the type III secretion system encoded within *Salmonella* pathogenicity island 1," J Mol Biol, 2008, 377(1):47-61.
Thiel et al., "Characterization of genes for a second Modependent nitrogenase in the cyanobacterium *Anabaena variabilis*," J. Bact., 1997, 179:5222-5225.
Thomas et al., "Ammonium Excretion by an I-Methionine-dl-Sulfoximine-Resistant Mutant of the Rice Field Cyanobacterium *Anabaena siamensis*," Appl Environ Microbiol., Nov. 1990, 56(11):3499-3504.
Thony et al., Dual control of the Bradyrhizobium japonicum symbiotic nitrogen fixation regulatory operon fixR nifA: analysis of cis- and trans-acting elements. J Bacteriol. Aug. 1989;171(8):4162-9.
Tijssen, "Laboratory Techniques In Biochemistry And Molecular Biology," Elsevier, 1993, 24:65 pages.
Tilman et al., "Global food demand and the sustainable intensification of agriculture," PNAS, 2011, 108:20260-20264.
Triplett, "Diazotrophic endophytes: progress and prospects for nitrogen fixation in monocots," Plant and Soil, 1996, 186:29-38.
Tritt et al., "An Integrated Pipeline for de Novo Assembly of Microbial Genomes," PLoS One, Sep. 2012, 7(9):e42304, 9 pages.
Troisfontaines et al., Type III secretion: more systems than you think. Physiology (Bethesda). Oct. 2005;20:326-39.

(56) References Cited

OTHER PUBLICATIONS

Tsukada et al., Comparative genome-wide transcriptional profiling of Azorhizobium caulinodans ORS571 grown under free-living and symbiotic conditions. Appl Environ Microbiol. Aug. 2009;75(15):5037-46. doi: 10.1128/AEM.00398-09. Epub Jun. 19, 2009.

Ueda et al., "Remarkable N2-Fixing Bacterial Diversity Detected in Rice Roots by Molecular Evolutionary Analysis of nifH Gene Sequences," Journal of Bacteriology, Mar. 1995, 177:1414-1417.

Uozumi et al., "Cloning and Expression of the nif A Gene of Klebsiella oxytoca in K. pneumoniae and Azospirillum lipoferum," Agricultural and Biological Chemistry, 1986, 50(6):1539-1544.

Van Dongen, "Performance criteria for graph clustering and Markov cluster experiments," CWI, 2000, 36 pages.

Van Heeswijk et al., "Nitrogen Assimilation in *Escherichia coli*: Putting Molecular Data into a Systems Perspective," Microbiology and Molecular Biology Reviews, Dec. 2013, 77(4):628-695.

Venkateshwaran et al., Exploring the feasibility of transferring nitrogen fixation to cereal crops. Chapter 42. Principles of Plant Microbe Interactions. 2015; 403-10.

Vernon et al., "Analysis of 16S rRNA gene sequences and circulating cell-free DNA from plasma of chronic fatigue syndrome and non-fatigued subjects," BMC Microbiology, 2002, 2:39, 6 pages.

Villa et al., "Azotobacter vinelandii siderophore can provide nitrogen to support the culture of the green algae neochloris oleoabundans and scenedesmus," FEMS Microbial. Lett., 2014, 351(1):70-77.

Villalobos et al., "Gene Designer: a synthetic biology tool for constructing artificial ONA segments," BMC Bioinformatics, 2006, 7:285, 8 pages.

Wang et al., "A minimal nitrogen fixation gene cluster from *Paenibacillus* sp. WLY78 enables expression of active nitrogenase in *Escheichia coli*," Plos Genetics, 2013, 9(10):1-11.

Wang et al., "Ligand-inducible and liver-specific target gene expression in transgenic mice," Nat Biotechnol., Mar. 1997, 15(3):239-43.

Wang et al., "Positive and negative regulation of gene expression in eukaryotic cells with an inducible transcriptional regulator," Gene Ther., May 1997, 4(5):432-441.

Wang et al., "Programming cells by multiplex genome engineering and accelerated evolution," Nature, Aug. 2009, 460(7257):894-8.

Wang et al., "Roles of poly-3-hydroxybutyrate (PHB) and glycogen in symbiosis of Sinorhizobium meliloti with *Medicago* sp.," Microbiology, Feb. 2007, 153(2):388-398.

Wang et al., Biofilm formation enables free-living nitrogen-fixing rhizobacteria to fix nitrogen under aerobic conditions. The ISME Journal, Jul. 2017, 11:1602-1613.

Watanabe et al., "Total biosynthesis of antitumor nonribosomal peptides in *Escherichia coli*," Nature Chemical Biology, 2006, 2:423-428.

Wei et al., "Endophytic nitrogen-fixing Klebsiella variicola strain DX120E promotes sugarcane growth," Biology and fertility of soils, 2014, 50:657-666.

Wells, "Additivity of mutational effects in proteins," Biochemistry, 1990, 29:8509-8517.

Wen et al., "Enabling Biological Nitrogen Fixation for Cereal Crops in Fertilized Fields," ACS Synth. Biol., Dec. 2021, 10(12):3264-3277.

Wenzel et al., "Recent developments towards the heterologous expression of complex bacterial natural product biosynthetic pathways," Curr Opin Biotechnol, 2005, 16(6):594-606.

Widmaier et al., "Engineering the *Salmonella* type III secretion system to export spider silk monomers," Mol. Syst. Biol., 2009, 5:309, 9 pages.

Wimpenny et al., Community structure and co-operation in biofilms. 59th Symposium of the Society for General Microbiology, Allison et al. (eds.), Sep. 2000, 23 pages.

Witkowski et al., "Conversion of a β-Ketoacyl synthase to a malonyl decarboxylase by replacement of the active-site cysteine with glutamine," Biochemistry, Sep. 1999, 38(36):11643-50.

Woolbright et al., "Novel insight into mechanisms of cholestatic liver injury," World J Gastroenterol., Sep. 2012, 18(36):4985-93.

Wootton et al., "Statistics of local complexity in amino acid sequences and sequence databases," Computers & Chemistry, Jun. 1993, 17(2):149-163.

Wu et al., "Effects of biofertilizer containing N-fixer, P and K solubilizers and AM fungi on maize growth: a greenhouse trial," Geodernna, Mar. 2005, 125(1-2):155-166.

Wu et al., "Multivariate modular metabolic engineering of *Escherichia coli* to produce resveratrol from L-tyrosine," J. Biotechnol., 2013, 167:404-411.

Wu et al., "Root exudates from two tobacco cultivars affect colonization of Ralstonia solanacearum and the disease index," European Journal of Plant Pathology, 2014, 141(4):667-677.

Xie et al., "Interaction between NifL and NifA in the nitrogen-fixing Pseudomonas stutzeri A1501," Microbiology (Reading), Dec. 2006, 152(Pt 12):3535-3542.

Xu et al., "ePathBrick: a synthetic biology platform for engineering metabolic pathways in *E. coli*.," ACS Synth. Biol., 2012, 1:256-266.

Yan et al., "Global transcriptional analysis of nitrogen fixation and ammonium repression in rootassociated Pseudomonas stutzeri A1501," BMC Genomics, Jan. 2010, 11(11):1-13.

Yan et al., Nitrogen fixation island and rhizosphere competence traits in the genome of root-associated Pseudomonas stutzeri A1501. PNAS. May 2008; 105(21): 7564-9.

Yao et al., "Complementation analysis of heterologous nifA genes to nifA mutants of Sinorhizobium pallida," Chinese Science Bulletin, Oct. 2006, 51(19):2258-2264, 2 pages (English abstract only).

Yarza et al., "Uniting the classification of cultured and uncultured bacteria and archaea using 16S rRNA gene sequences," Nature Rev. Micro., 2014, 12:635-345.

Ye et al., "Primer-BLAST: a tool to design target-specific primers for polymerase chain reaction," BMC Bioinformatics., Jun. 2012, 13(134):1-11.

Yokobayashi et al., "Directed evolution of a genetic circuit," Proc Natl Acad Sci USA, 2002, 99(26):16587-16591.

Yoshida et al., "Atmospheric dinitrogen fixation in the flooded rice rhizosphere as determined by the N-15 isotope technique," Soil Science and Plant Nutrition, Dec. 1980, 26(4):551-559.

Yu et al., Recombineering Pseudomonas protegens CHAO: An innovative approach that improves nitrogen fixation with impressive bactericidal potency.Microbiological Research, Jan. 2019,218:58-65.

Zaslaver et al., "Optimal gene partition into operons correlates with gene functional order," Phys Biol, 2006, 3(3):183-189.

Zazopoulos et al., "A genomics-guided approach for discovering and expressing cryptic metabolic pathways," Nat Biotechnol, 2003, 21(2):187-190.

Zehr et al., "New Nitrogen-Fixing Microorganisms Detected in Oligotrophic Oceans by Amplification of Nitrogenase (nifH) Genes," Appl Environ Microbiol., Sep. 1998, 64(9):3444-3450.

Zehr Lab NifH database, retrieved from URL <https://wwwzehr.pmc.ucsc.edu/nifH_Database_Public/>, Apr. 4, 2014, 1 page.

Zhang et al., "GlnD Is Essential for NifA Activation, NtrB/NtrC-Regulated Gene Expression, and Posttranslational Regulation of Nitrogenase Activity in the Photosynthetic, Nitrogen-Fixing Bacterium Rhodospirillum rubrum," J. Bacteriol., Feb. 2005, 187(4): 1254-1265.

Zhang et al., "Mutagenesis and functional characterization of the four domains of GlnD, a bifunctional nitrogen sensor protein," J Bacteriology, Jun. 2010, 192(11):2711-2721.

Zhang et al., "Mutagenesis and Functional Characterization of the glnB, glnA, and nifA Genes from the Photosynthetic Bacterium Rhodospirillum rubrum," Journal of Bacteriology, Feb. 2000, 182(4):983-992.

Zhao et al., "Evidence for nifU and nifS participation in the biosynthesis of the iron-molybdenum cofactor of nitrogenase," J. Biol. Chem., 2007, 282(51):37016-37025.

Zomer, "PPP: Perform Promoter Prediction," retrieved from URL <http://bioinformatics.biol.rug.nl/websoftware/ppp/ppp_start.php>, 2011, 2 pages.

* cited by examiner

Design

Constrain: [promoter] = P1,P2,P3,null
[rbs] = RBSx1,RBSx5
[terminator] = T1,null
[order] = U,S,V < W,Z,M Permute: promoter strength and number
RBS strength
terminator number
gene order and orientation

Build

Test

Activity

Analyze

Sequence

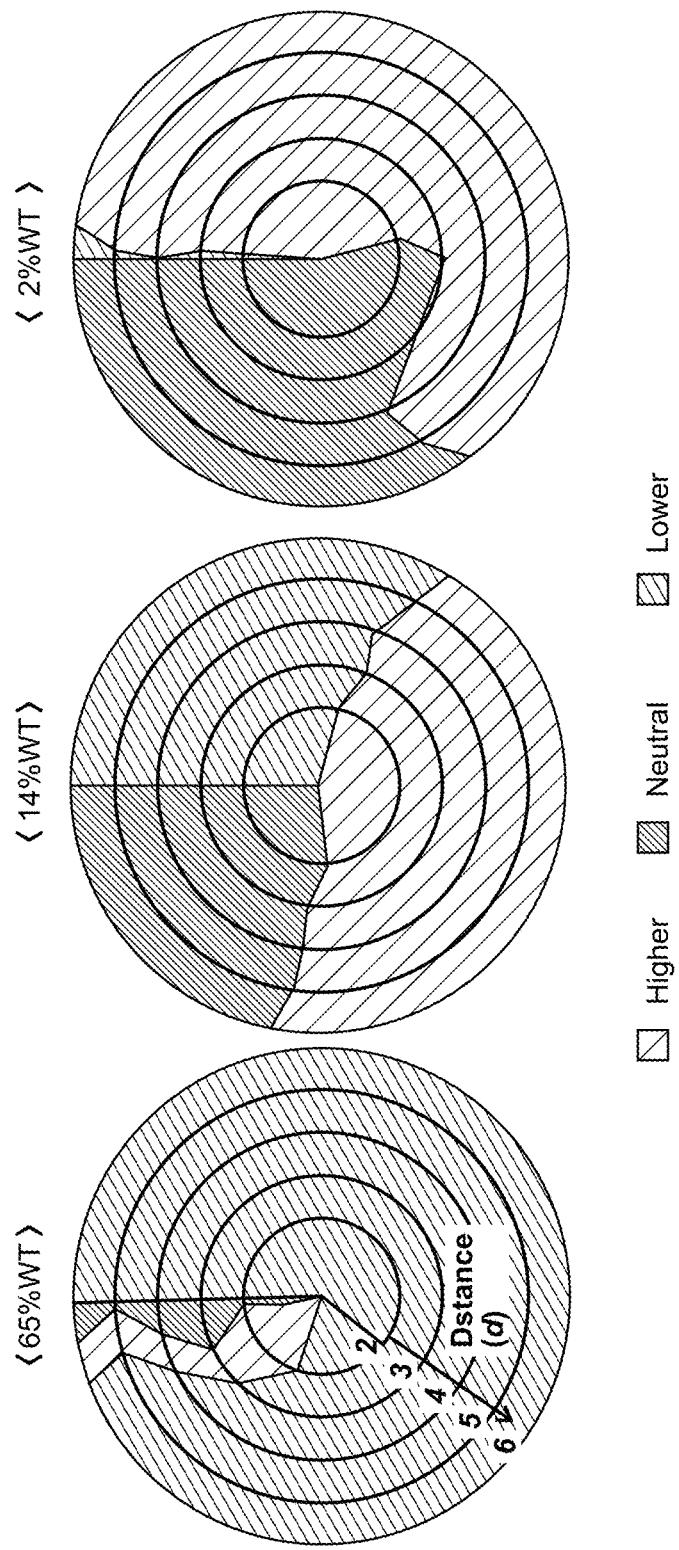

T7* RNAP expression (a.u.)

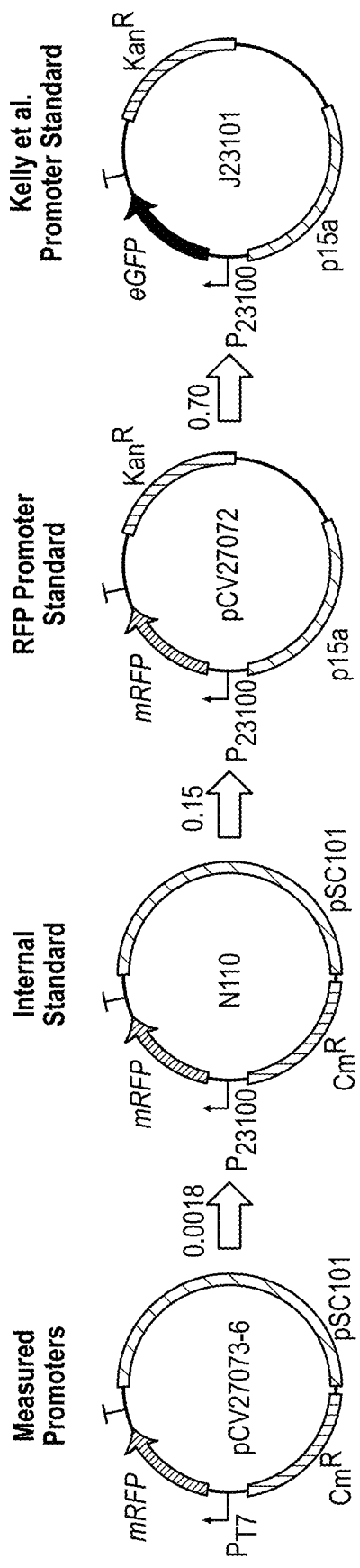
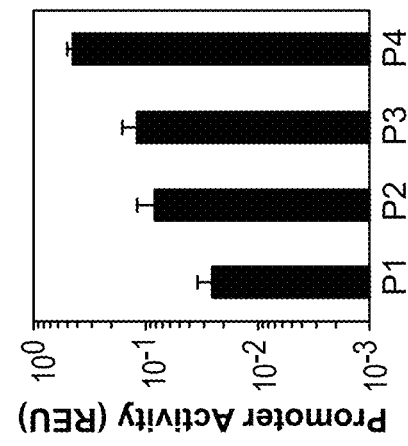
FIG. 7A
FIG. 7B

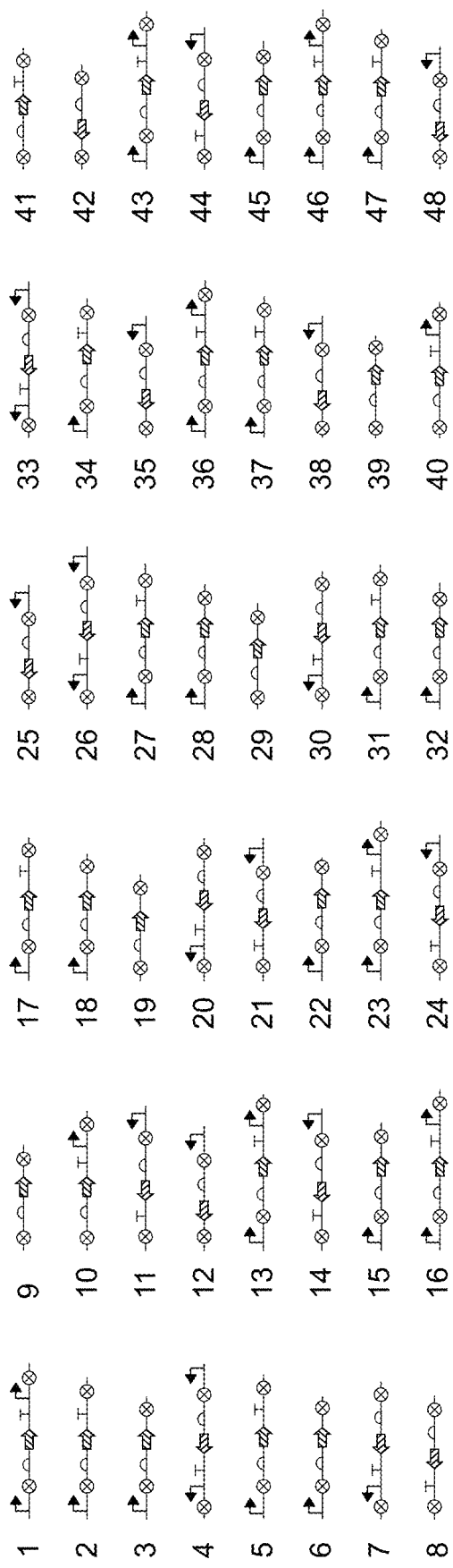

V-b: Design and/or the full *nif* clusters

FIG. 16A

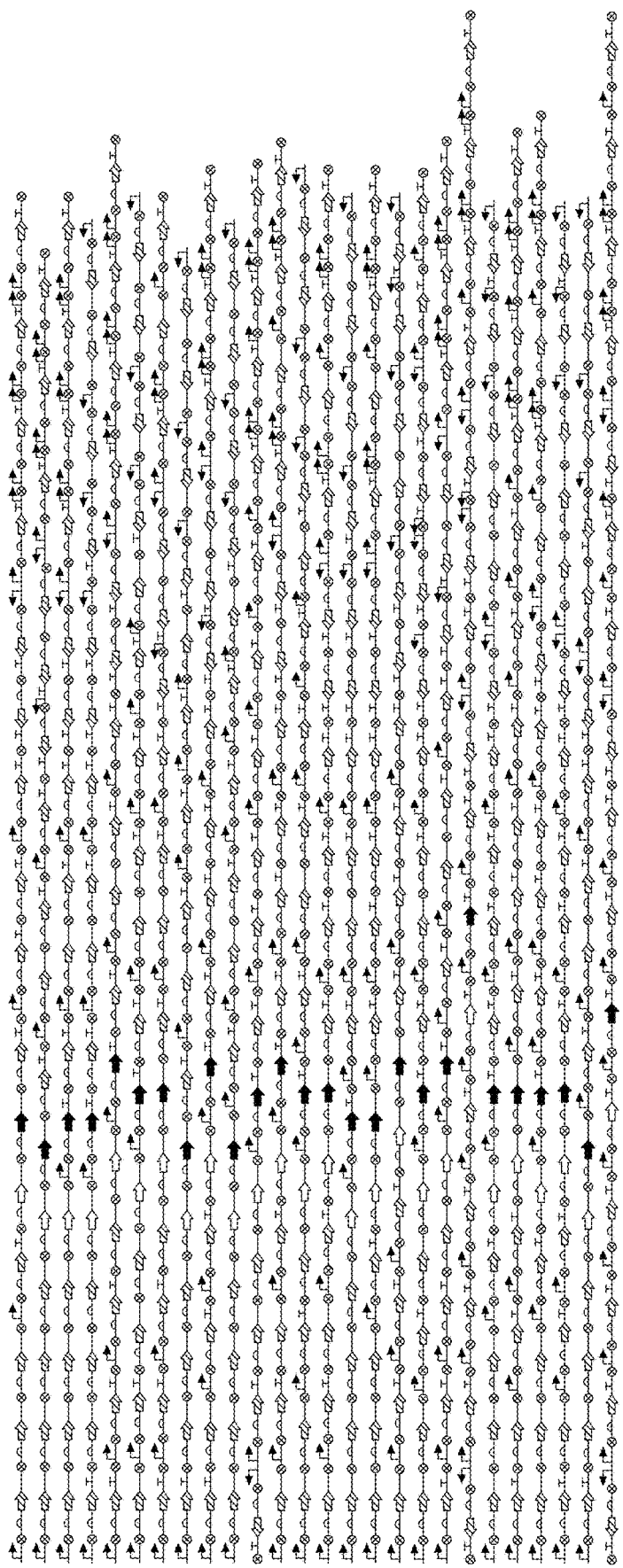
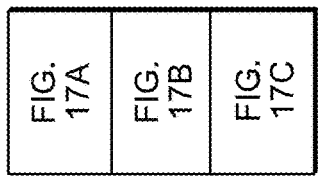
FIG. 17A
FIGS. 17A-17C

DIRECTED EVOLUTION OF SYNTHETIC GENE CLUSTER

RELATED APPLICATIONS

This application is a continuation of U.S. patent application Ser. No. 14/440,183, filed on May 1, 2015, which is a national stage filing under 35 U.S.C. § 371 of PCT International Application PCT/US2013/068055, filed on Nov. 1, 2013, which claims priority under 35 U.S.C. § 119(e) to U.S. Provisional Application Ser. No. 61/721,188, entitled "DIRECTED EVOLUTION OF SYNTHETIC GENE CLUSTER" filed on Nov. 1, 2012, each of which is herein incorporated by reference in its entirety.

FEDERALLY SPONSORED RESEARCH

This invention was made with Government support under Grant No. EEC0540879 awarded by the National Science Foundation and under Grant No. HR0011-12-C-0067 awarded by the Defense Advanced Research Projects Agency. The Government has certain rights in the invention.

BACKGROUND OF THE INVENTION

Many cellular functions are encoded in gene clusters, the manipulation of which is complicated by their size and genetic complexity. Several challenges inhibit the engineering of large systems composed of many genetic parts. First, the process of design is tedious, with computational design environments focused at combining parts at the primary DNA-sequence level[1-4]. Second, the time required to prototype a design is slow. While DNA synthesis is now routine for individual genes[5,6] and has been used to build entire 500 kilobase genomes[7], it remains too expensive to simultaneously synthesize many alternative designs. This slows the design build-test cycle because only small sets of designs can be constructed and evaluated per iteration. Further, native genetic systems are riddled with overlapping and cryptic elements that complicate part replacement and optimization[8-11].

SUMMARY OF THE INVENTION

The invention, in various aspects, relates to methods and products for refactoring complex genetic clusters. In some aspects of the invention, the library contains a plurality of distinct non-naturally occurring genetic clusters, wherein each genetic cluster is organized into transcriptional units which are composed of a plurality of modular units, each modular unit composed of one or more genetic components, wherein the modular units within the genetic cluster are arranged such that the plurality of distinct non-naturally occurring genetic clusters are distinct from a naturally occurring genetic cluster based on the number, the order, and/or the orientation of particular genetic components.

In some embodiments, naturally occurring non-coding DNA has been removed from at least one of the transcriptional units. In other embodiments, naturally occurring non-coding DNA has been removed from all of the transcriptional units. In some embodiments, each genetic cluster includes 10-100 transcriptional units. In some embodiments, non-essential genes have been removed from a plurality of the genetic clusters. In other embodiments, non-essential genes have been removed from all of the genetic clusters. In some embodiments, naturally occurring regulatory sequences have been removed from all of the genetic clusters. In some embodiments, the naturally occurring regulatory sequences are transcription factors.

In other embodiments, a plurality of the modular units that include coding DNA and wherein the coding DNA differs from naturally occurring coding DNA by encompassing randomized codons. In some embodiments, at least one of the genetic components is a synthetic regulatory element and wherein the synthetic regulatory elements are selected from the group consisting of promoters, ribosome binding sites, ribozymes, and transcription terminators.

The genetic clusters lack restriction recognition sites in yet other embodiments. In some embodiments, the gene clusters are monocistronic. In other embodiments, the gene clusters are polycistronic.

In some embodiments, the library contains a plurality of gene clusters that produce functional compounds, which in some instances perform a biological process.

In some embodiments, the plurality of gene clusters have a configuration that is different than a naturally occurring corresponding gene cluster. In some embodiments, the genetic clusters encode proteins comprising a biosynthetic pathway. In some embodiments, the biosynthetic pathway is the nitrogen fixation pathway.

In some embodiments, one or more of the synthetic regulatory elements are genetically linked to one or more protein coding sequences of the genetic cluster. In some embodiments, the plurality of distinct non-naturally occurring genetic clusters is 5-1,000. In some embodiments, the plurality of distinct non-naturally occurring genetic clusters is 10-500. In some embodiments, the plurality of distinct non-naturally occurring genetic clusters is 10-100.

Aspects of the invention relate to a non-naturally occurring genetic cluster that is organized into transcriptional units which are composed of a plurality of modular units, each modular unit composed of a plurality of genetic components having synthetic regulatory elements genetically linked to one or more protein coding sequences, wherein the genetic cluster is designed to express a plurality of proteins comprising a biosynthetic pathway and wherein the expression of the proteins is under the control of synthetic circuits, and wherein non-essential genes have been removed from a plurality of the genetic clusters.

In some embodiments, the gene cluster has a configuration that is different than a naturally occurring corresponding gene cluster. In some embodiments, the genetic cluster lacks restriction recognition sites.

Some aspects of the invention relate to a method of C3. producing a diverse genetic library including identifying a target genetic cluster of genes, producing a plurality of distinct non-naturally occurring genetic clusters from the target genetic cluster by preparing a plurality of modular units from one or more genetic components using a scarless stitching assembly, reassembling the modular units in a plurality of distinct patterns to produce the plurality of distinct non-naturally occurring genetic clusters, wherein the plurality of distinct non-naturally occurring genetic clusters form the diverse genetic library.

In some embodiments, native regulatory elements are removed from the genetic components. In some embodiments, the genetic components are composed of all synthetic regulatory elements.

In some embodiments, the one more genes from the target genetic cluster and the one or more standard regulatory element are combined based on a constrained language of synthetic biology/rules of gene expression (EUGENE).

In some embodiments, the genetic clusters encode proteins comprising a biosynthetic pathway and wherein a function of the biosynthetic pathway is evaluated. In some embodiments, the genes are reassembled in a different order than the genes of the naturally occurring gene cluster. In some embodiments, the genes are reassembled in a different orientation than the genes of the naturally occurring gene cluster. In some embodiments, the genetic components include one or more promoters that have a different strength than promoters of the naturally occurring gene cluster. In other embodiments, the plurality of distinct non-naturally occurring genetic clusters include a different number or promoters than the naturally occurring gene cluster. In some embodiments, the genetic components include one or more terminators that have a different strength than terminators of the naturally occurring gene cluster. In other embodiments, the plurality of distinct non-naturally occurring genetic clusters include a different number or terminators than the naturally occurring gene cluster.

In some embodiments, a computer program is used to generate the distinct non-naturally occurring genetic clusters. In some embodiments, the computer program uses a programming language for genetic systems. In some embodiments, the programming language is EUGENE.

In some embodiments, the target gene cluster is derived from a first organism and is expressed from a second organism.

Aspects of the invention relate to a method for scarless stitching involving identifying at least three consecutive units of a genetic construct, each unit in a partial plasmid and is flanked by a 4-10 nucleotide upstream and downstream flanking sequence that forms 5' cohesive ends when digested with a restriction enzyme, digesting the first and second units with a first restriction enzyme and digesting the third unit with a second restriction enzyme to produce cohesive ends, and ligating the cohesive ends to produce a plasmid.

In some embodiments, the first unit is a regulatory unit. In some embodiments, the regulatory unit is a promoter unit. In some embodiments, the second unit is a Ribosomal binding site (RBS)/coding DNA sequence (CDS) unit. In some embodiments, the third unit is a terminator unit.

In some embodiments, the flanking sequences are 6 nucleotides in length.

Some aspects of the invention related to a method of refactored gene cluster assembly that involves using scarless stitching assembly to connect a plurality of genetic components into nucleic acid modular units, PCR amplification of the nucleic acid modular units to produce modular units having a sequence that will produce cohesive ends upon enzymatic digestion, insertion of the modular units having cohesive ends into plasmids using the cohesive ends to assemble the modular units in a manner that dictates orientation and relative position of the modular units within the plasmid to produce multiple plasmids having different modular units embedded therein, and combining the multiple plasmids to produce plasmids that have a complete refactored gene cluster.

In some embodiments, the method also includes testing the refactored gene cluster for functional activity. In some embodiments, the refactored gene clusters having functional activity are analyzed to produce a list of gene cluster parts associated with an activity level. In some embodiments, the activity level is a high activity level. In other embodiments, the activity level is a low activity level. In some embodiments, rules for producing a functional gene cluster are generated based on the list of gene cluster parts associated with an activity level.

In some embodiments, the step of insertion of the modular units having cohesive ends into plasmids involves the use of Golden Gate Assembly.

Other aspects of the invention relate to a diverse seed library that contains a plurality of seeds, each seed being a modular unit composed of one or more genetic components, having a structure different than other seeds in the library, wherein the combination of genetic components within each modular unit is distinct from a naturally occurring modular unit based on the number, the order, or the orientation of particular genetic components.

In some embodiments, the seeds are arranged in a plurality of distinct non-naturally occurring genetic clusters, wherein each genetic cluster includes a plurality of seeds. In some embodiments, library includes a set of seeds wherein each modular unit within the set has the same gene, gene orientation, gene order, terminators, and transcription units, but a distinct number of promoters. In some embodiments, the library includes a set of seeds wherein each modular unit within the set has the same gene orientation, gene order, promoters, terminators, and transcription units, but a distinct gene. In some embodiments, the library includes a set of seeds wherein each modular unit within the set has the same gene, gene order, promoters, terminators, and transcription units, but a distinct gene orientation. In other embodiments, the library includes a set of seeds wherein each modular unit within the set has the same gene, gene orientation, promoters, terminators, and transcription units, but a distinct gene order. In other embodiments, the library includes a set of seeds wherein each modular unit within the set has the same gene, gene orientation, gene order, promoters, and transcription units, but a distinct number of terminators. In still other embodiments, the library includes a set of seeds wherein each modular unit within the set has the same gene, gene orientation, gene order, promoters, and terminators, but a distinct number of transcription units.

Some aspects of the invention pertain to a method of generating a database of diverse seeds associated with functionality that includes for each of the plurality of seeds within the diverse seed library, computationally generating a functionality value based on experimental data associated with each of the seeds in the context of a genetic cluster, and storing information on the functionality value in a plurality of entries in the database, each entry including a seed value corresponding to an identifier of the seed and information on the functionality comprising one or more of the following: a value corresponding to a high activity functionality or a low activity functionality, or a value corresponding to a qualitative aspect of the functionality.

In some embodiments, the functionality value is calculated as a function of the activity of a gene cluster and the number of a specific variable present within a seed within the gene cluster. In some embodiments, the specific variable is selected from the group consisting of the number of genes, gene order, promoters, terminators, and transcription units. In other embodiments, the functionality value is calculated as a function of the activity of a gene cluster and the statistical enrichment or de-enrichment of a variable present within a seed within the gene cluster. In some embodiments, the variable is gene orientation or gene order.

Aspects of the invention relate to a system including at least one processor and memory communicatively coupled to the at least one processor and storing computer-executable instructions that, when executed by the at least one processor, perform a method of identifying an optimal set of seeds for assembly to produce a functional refactored genetic cluster. The method involves receiving experimental data obtained by analyzing a library of claim A, the experimental data comprising a functionality value generated by analyzing functionality of modular units or subsets thereof of the library in the context of the genetic cluster; identifying a desired functional refactored genetic cluster by comparing the functionality values of the modular units or subsets thereof included within a set of putative refactored genetic clusters; and comparing the functionality values of the resultant putative refactored genetic clusters.

In some embodiments, the functionality value is a value from a database. In other embodiments, the functionality value of a genetic cluster is calculated as the mean of functionality values of each modular unit or subset of modular unit within the genetic cluster. In some embodiments, the functionality value of each putative refactored genetic cluster is compared to identify the refactored genetic clusters with the highest and lowest functionality.

Other aspects of the invention relate to a peptide barcode library that includes a modular unit composed of one or more genetic components including at least one gene encoding for a protein comprising a biosynthetic pathway, wherein a unique peptide barcode is genetically fused to each gene. In some embodiments, the genetic components within each modular unit are distinct from genetic components in a naturally occurring modular unit based on the number, the order, or the orientation of particular genetic components. In some embodiments, the peptide barcode library includes multiple modular units linked together to form a refactored genetic cluster.

Kits comprising one or more sealed vials comprising an amount of any of the nucleic acid reagents and related reagents of the present invention are also provided. The kit may optionally include instructions for generating and/or screening libraries of the present invention in hard copy or computer readable form.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The figures are illustrative only and are not required for enablement of the invention disclosed herein.

FIG. 3C depicts circle diagrams illustrating paths through fitness landscape for subsets of nifUSVWZM library. Average activity of the subset is listed above each graph. Plots show average fraction of paths for adaptive, neutral, or maladaptive evolution as a function of increasing genetic distance.

FIG. 5E depicts an enrichment/ de-enrichment plot comparing the frequency of 5' promoters or terminators for each gene in a high-fitness subset (FHF) to the overall frequency (Ftotal) Operon structure of the wild-type (top row of arrows) and original refactored (bottom row of arrows) gene clusters are indicated below plots for reference.

Figure 6:
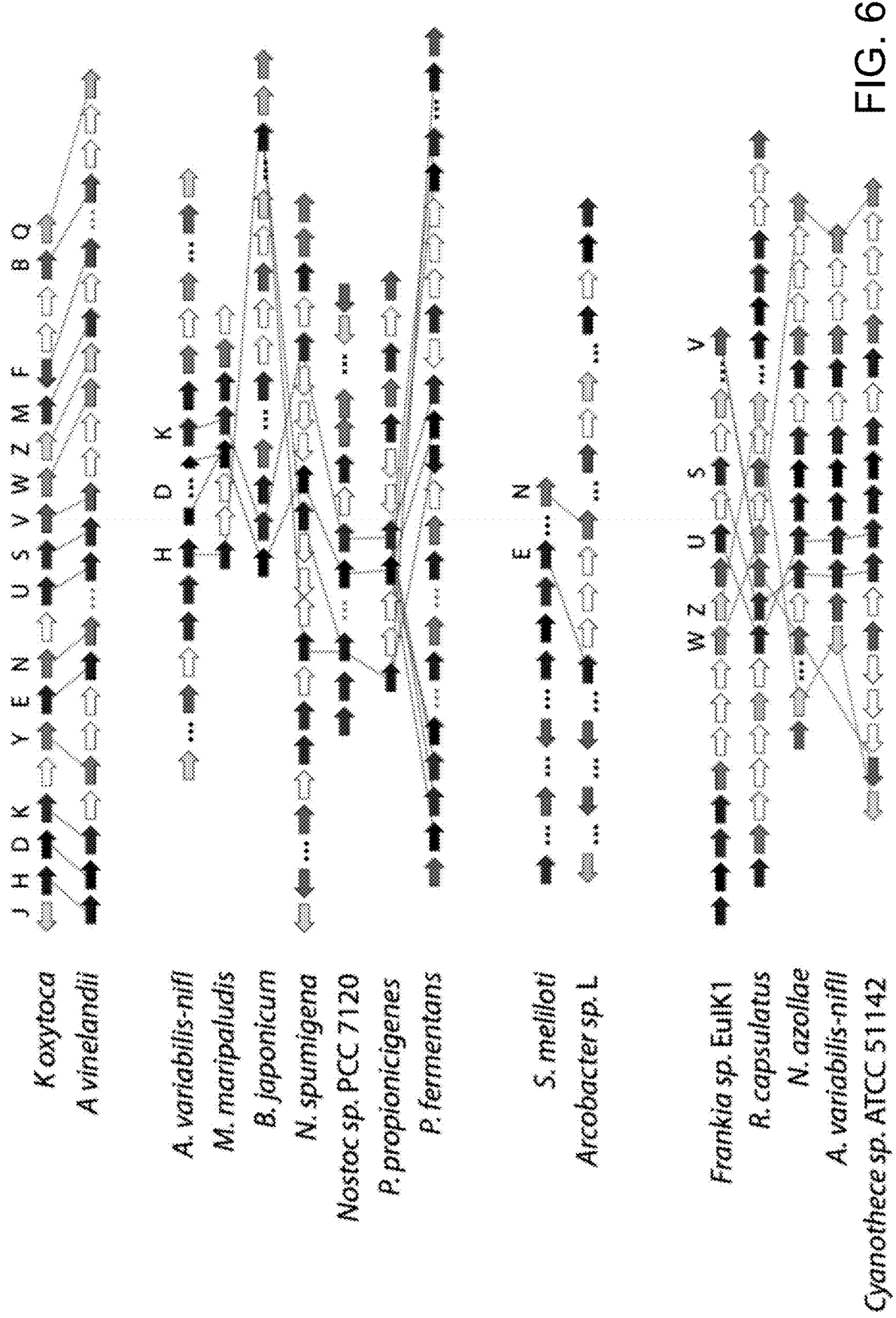

FIG. 6 presents natural examples of architectural diversity in nif gene clusters. Lines trace homologous genes in subsets that highlight diverse nifHDK, nifEN, and nifUSVWZM architectures. Accession numbers for displayed sequences are as follows: *Klebsiella oxytoca*, AMPJ01000097; *Azotobacter vinelandii*, NC_012560; *Anabaena variabilis*, CP000117; *Methanococcus maripaludis*, CP002913; *Bradyrhizobium japonicum*, NC_017249; *Nodularia spumigena*, AAVW01000003; *Nostoc* sp. PCC7120, BA000019; *Paludibacter propionicigenes*, CP002345; *Pelosinus fermentans*, AKVN01000037; *Sinorhizobium meliloti*, AE006469; *Arcobacter* sp. L, AP012048; *Frankia* sp. EuIK1, AF119361; *Rhodobacter capsulatus*, NC_014034; *Nostoc azollae*, NC_014248; *Cyanothece* sp. ATCC 51142, AY728386.

FIG. 7A schematically depicts characterization of the promoters. Conversion of arbitrary mRFP fluorescence units into REUs (a) was done by normalizing to an internal standard (N110) and scaling to account for plasmid backbone differences between our test construct and the Kelly et al. promoter standard3. Numbers above grey arrows reflect the conversion factors at each step. FIG. 7B depicts experimentally determined strengths for promoters used in this study are shown in REUs.

Figure 1A:
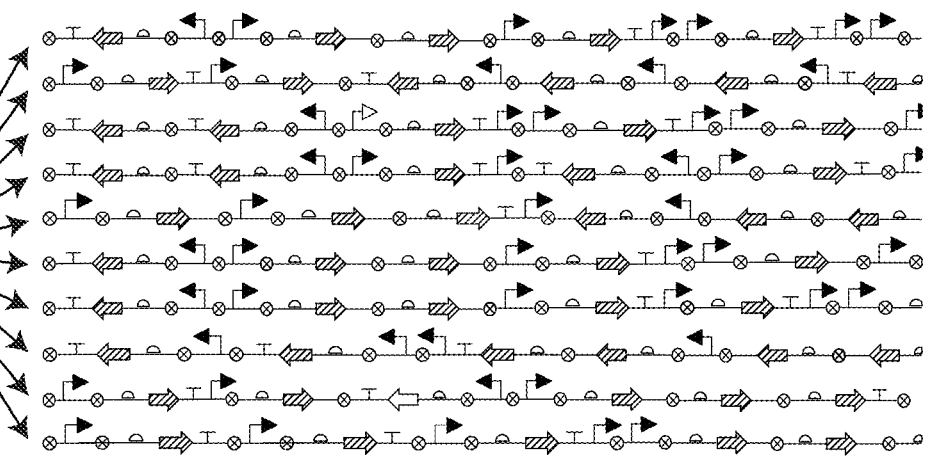
FIG. 1A illustrates the major steps for a multiplexed design-build-test cycle.
Figure 1A:
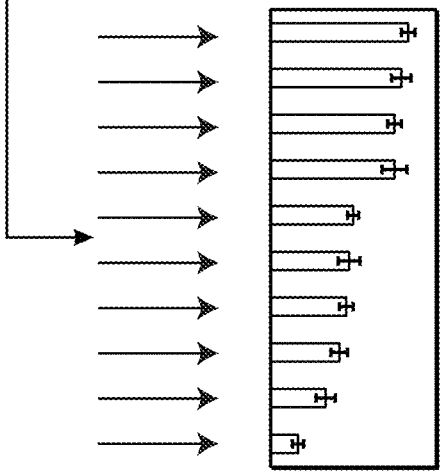
Figure 1A:
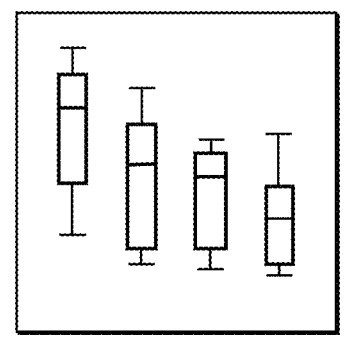
Figure 8C:
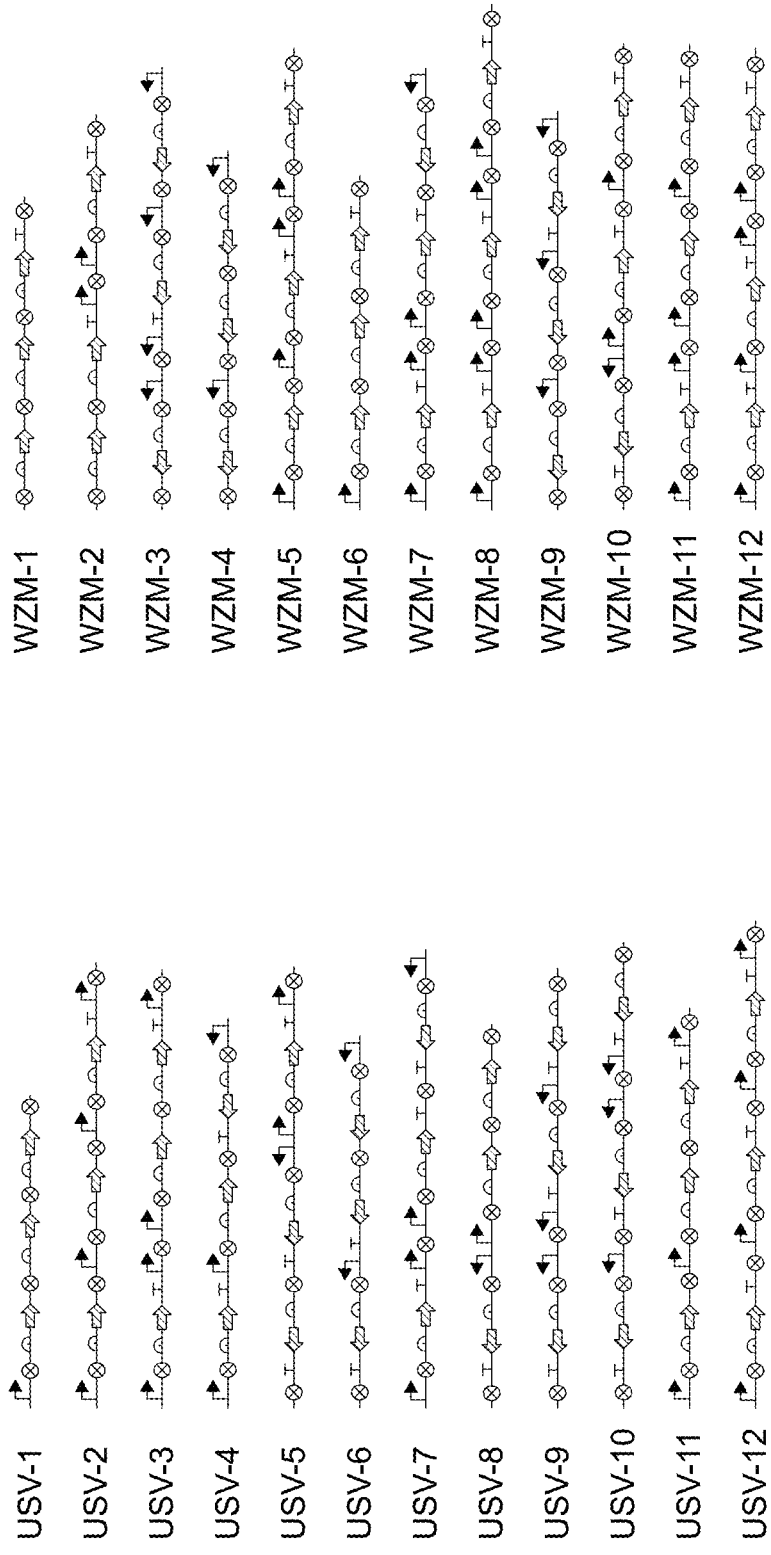

FIG. 8A presents the base parts used during construction of the nifUSVWZM library. FIG. 8B shows the cistron parts used in the construction of the library. FIG. 8C shows the half-custer parts of the library. Parts correspond to the assembly graph in FIGS. 1A-1C.

Figure 9:
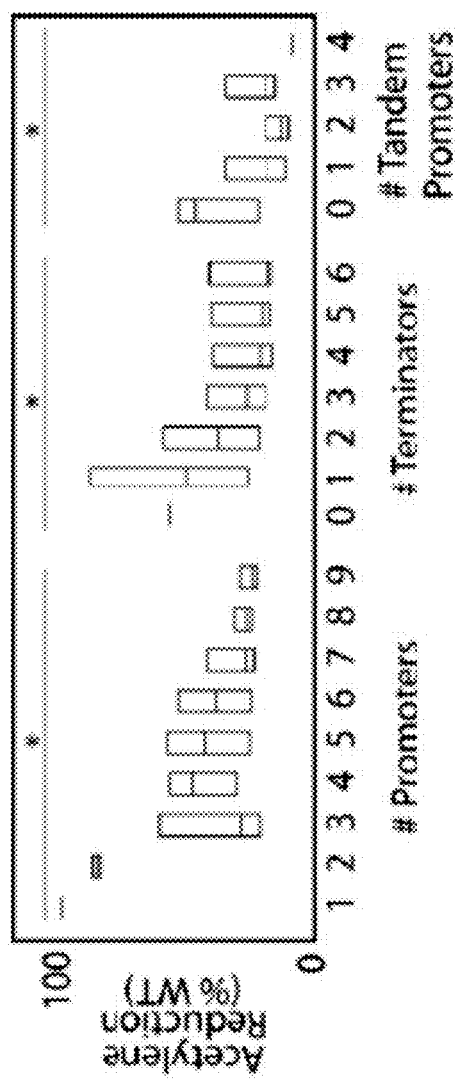

FIG. 9 shows additional significant correlations between acetylation reduction activity and sequence features including number of promoters (Spearmann correlation $\rho=-0.29$, probability score $p=0.008$), number of terminators ($\rho=-0.28$, $p=0.011$), and number of tandem promoters ($\rho=-0.34$, $p=0.002$). Box plots denote boundaries of second and third quartile (box) as well as the median value (center line) for each variable. Astericks denotes statistical significance.

Figure 10:
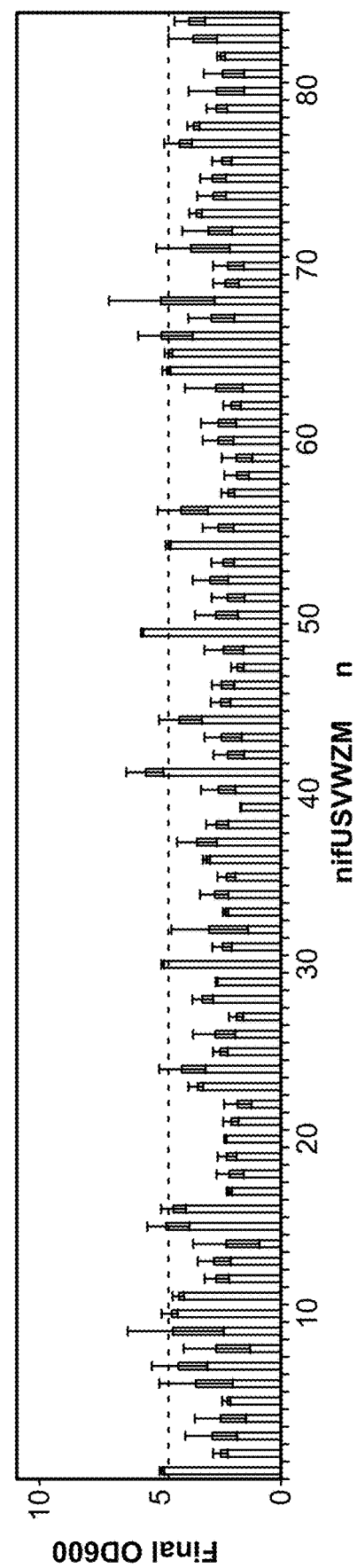

FIG. 10 presents the final OD600 of nifUSVWZM library following 1 mM IPTG induction. Final OD measurement is calculated based on measurement of a 1:10 diluted culture sample and adjusted for differences in OD measurement between plate reader and spectrophotometer. Dotted line represents final OD from wild-type *K. oxytoca* M5al grown in assay conditions with 1 mM IPTG.

Figure 1B:
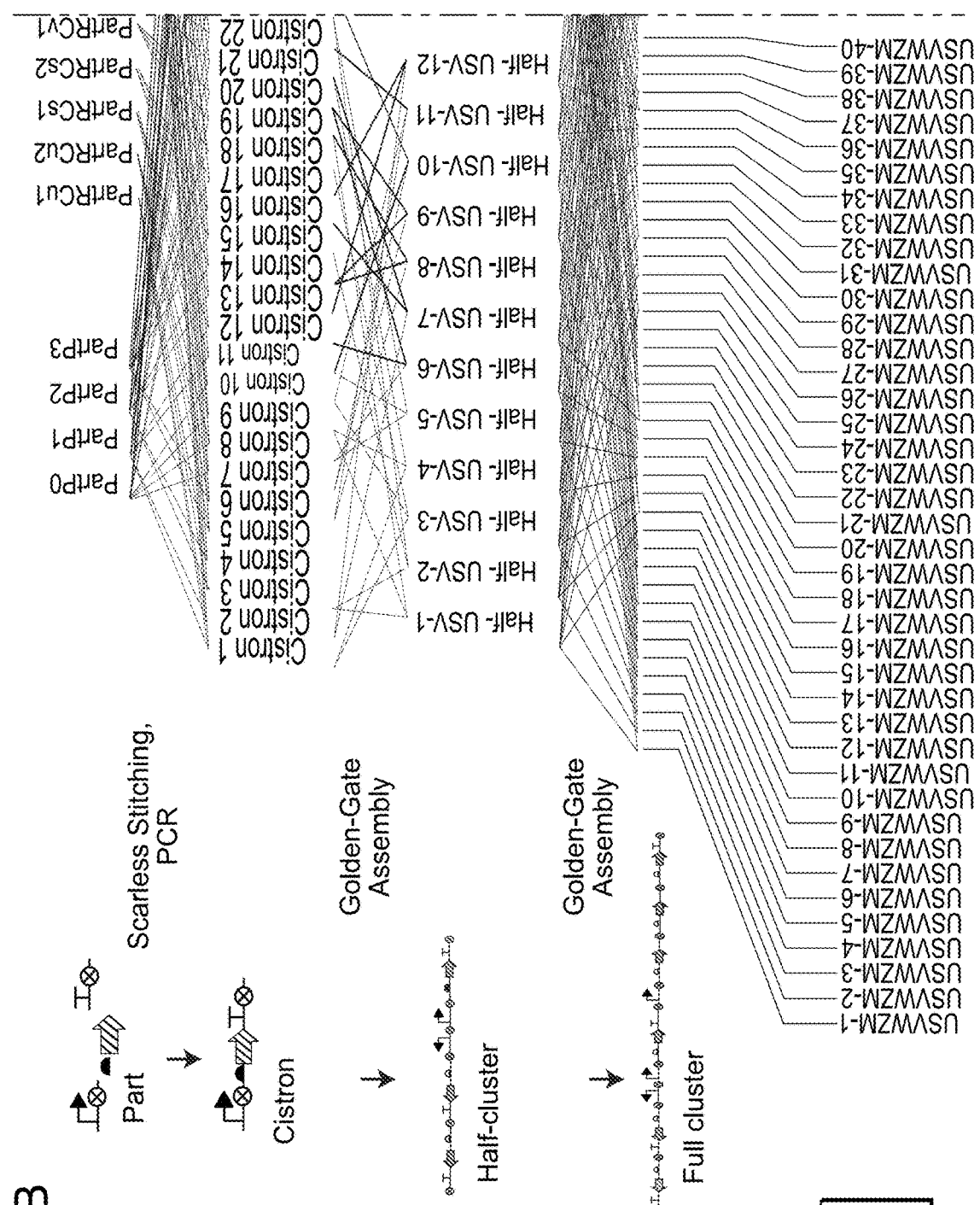
FIGS. 1B-1C show a summary of the DNA assembly pipeline with actual assembly graph for the nifUSVWZM library. Lines trace composition from base parts (top) to full constructs (bottom) with the relevant assembly method at each stage labeled and visually represented on left.
Figures 1B, 1C:
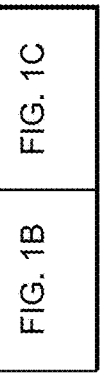
Figure 1C:
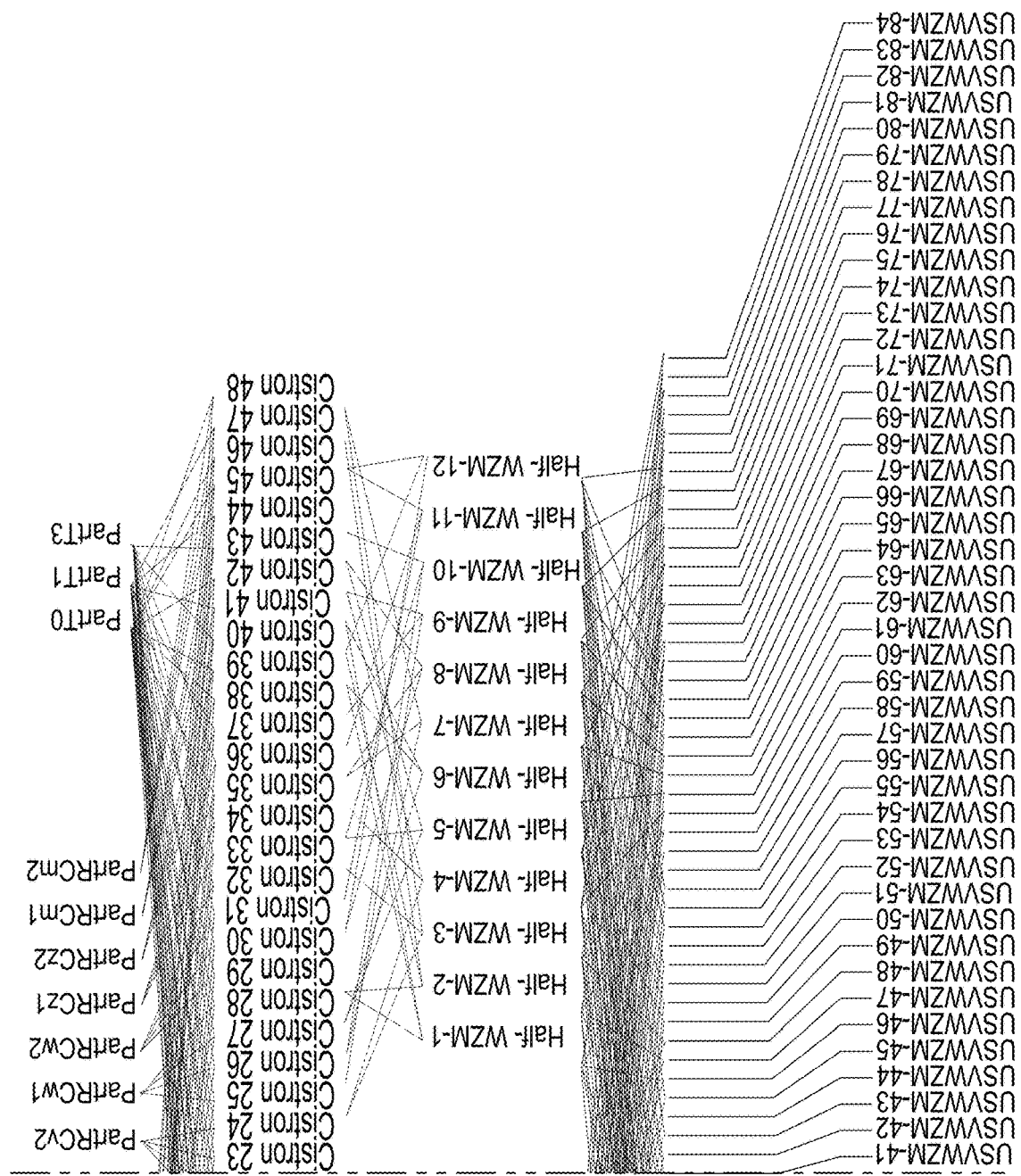
Figure 11A:
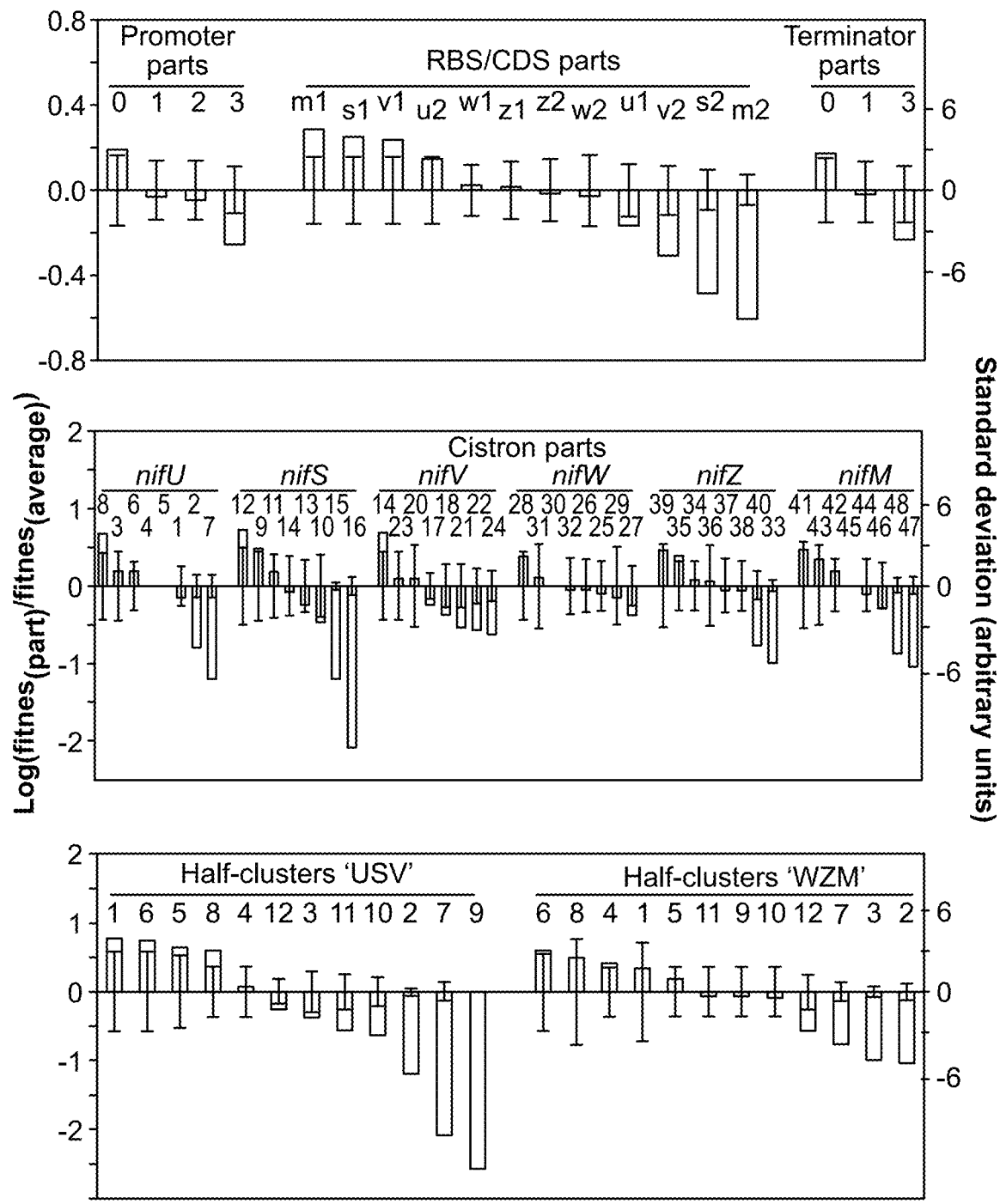
Figure 11B:
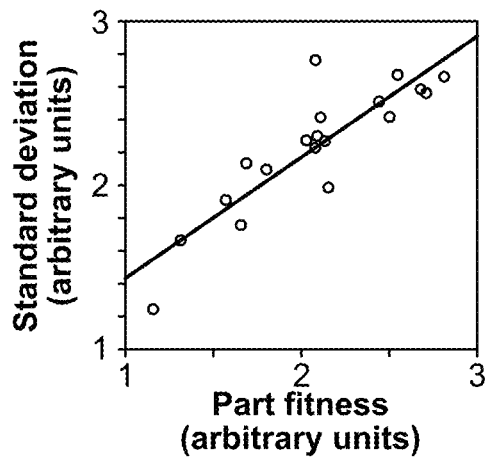
Figure 11B:
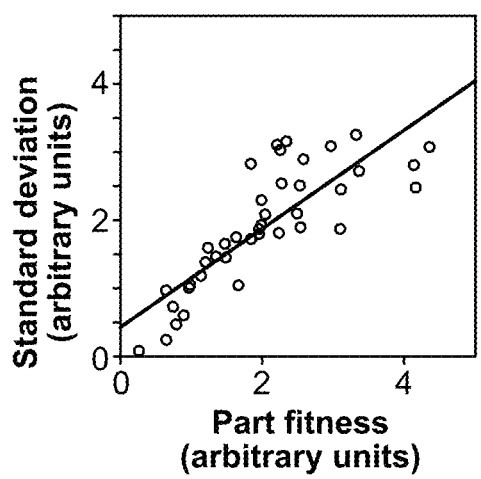
Figure 11B:
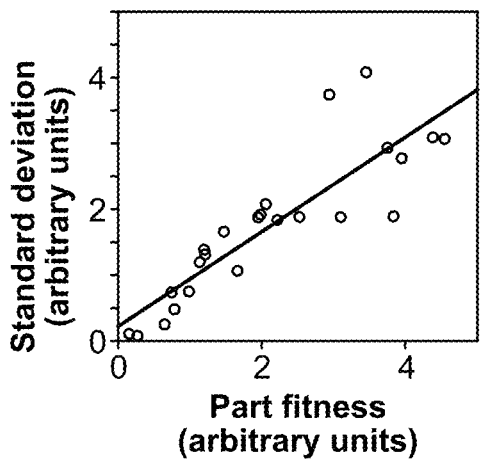
Figure 11C:
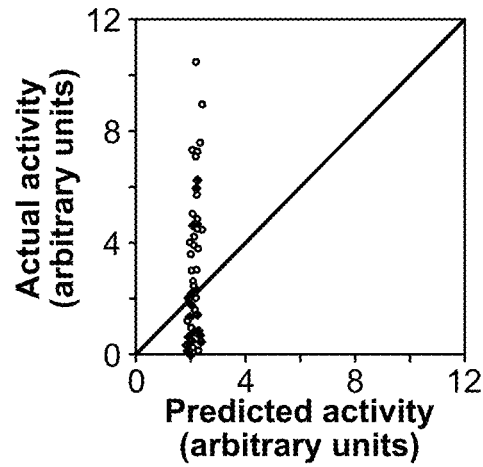
Figure 11C:
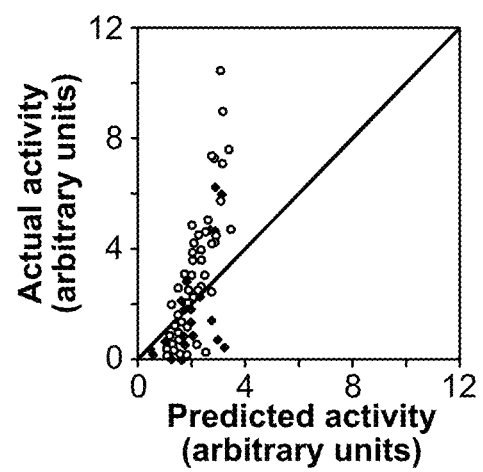
Figure 11C:
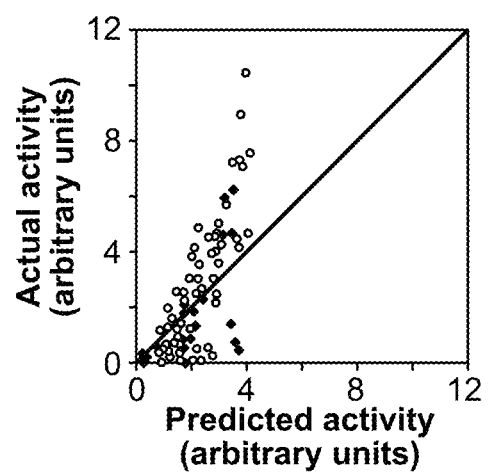

FIG. 11A depicts part fitnesses (left axis) as a log ratio normalized to average part fitness, and part standard deviation (error bars, right axis) shown at each level of the assembly hierarchy including base parts (top), cistron parts (middle), and half-clusters (bottom). Part names corresponding to the assembly graph in FIGS. 1B-1C are labeled above bars. FIG. 11B presents that plotted relationships between part fitness and part standard deviation are correlated with a variances of $R^2=0.77$ for base parts (top), $R^2=0.68$ for cistron parts (middle) and $R^2=0.75$ for half-clusters (bottom). FIG. 11C shows predicted cluster activity plotted against actual activity. Open circle points represent the original 84 library constructs and black diamonds are the 21 additional gene clusters constructed to verify predictability. Level of correlation to the y=x line improves at more advanced levels of assembly from $R^2=0.06$ for base parts (top) to $R^2=0.37$ for cistron parts (middle) and $R^2=0.54$ for half-clusters (top).

Figure 12B:
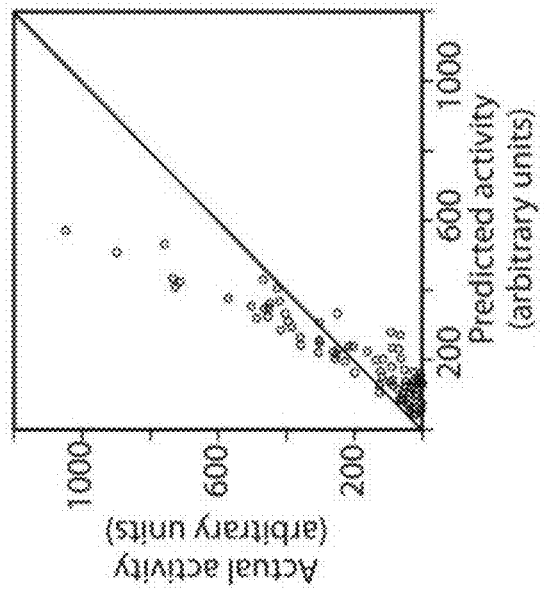
Figure 12A:
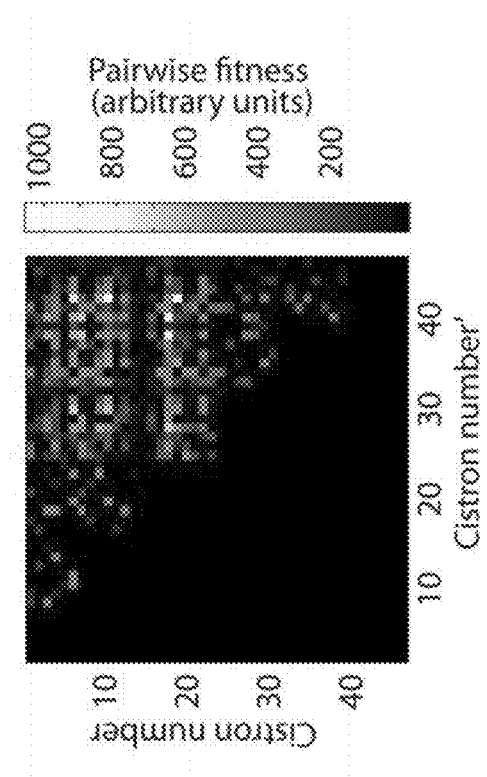

FIG. 12A presents a heatmap of pairwise part fitness for each combination of cistron parts, with shaded key showing corresponding values. Combinations not present in the library were given scores of 0 (black box) in the heatmap. FIG. 12B shows that the relationship between predicted and actual gene cluster activity using the pairwise fitness values in the prediction leads to an improved correlation to the y=x line, with $R^2=0.69$.

Figure 13:
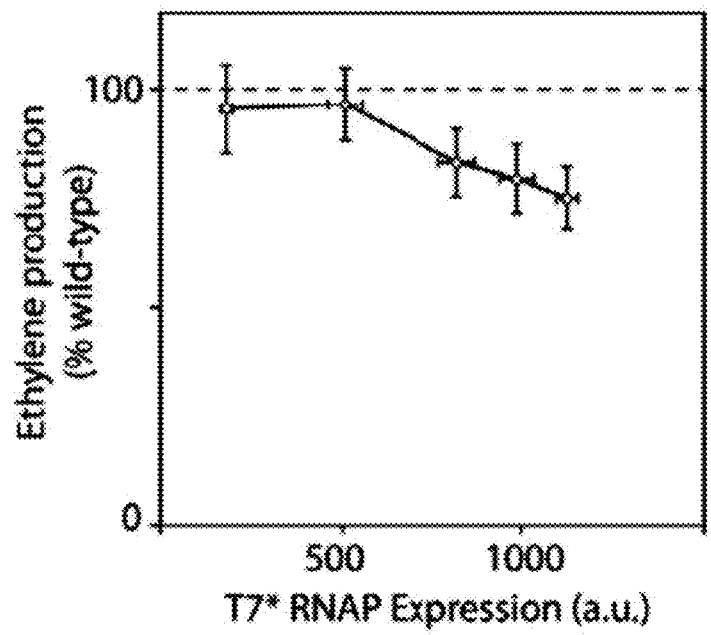

FIG. 13 depicts the robustness of natural nifUSVWZM under orthogonal control. Nitrogenase activity is plotted as a function of T7* RNAP expression. Points depict arithmetic mean of four measurements (two technical replicates of two biological replicates), with error bars denoting sample standard deviation.

Figure 14:
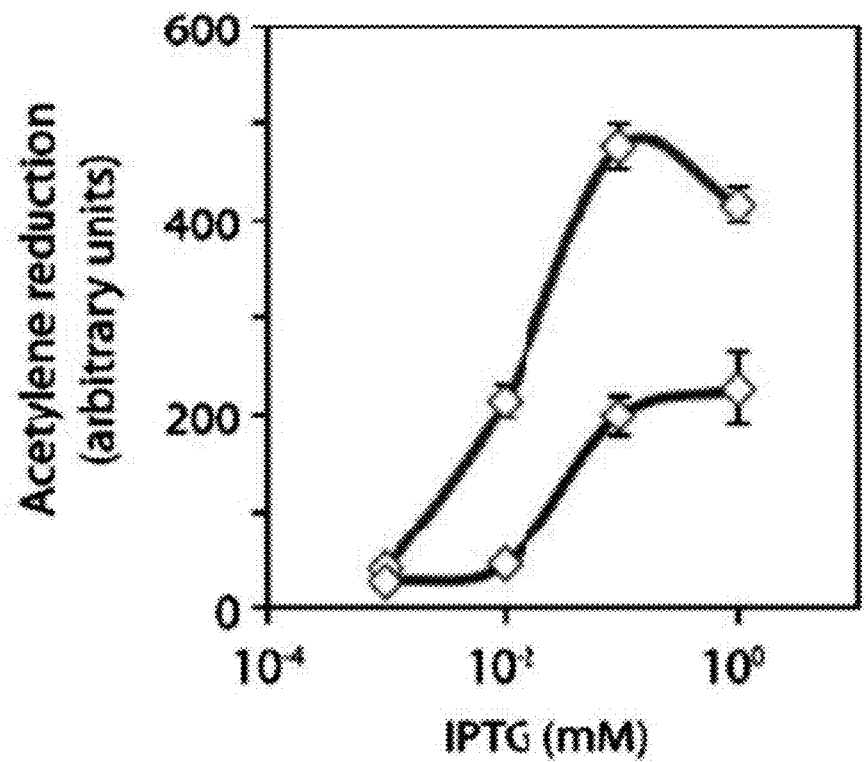

FIG. 14 shows optimization of the controller plasmid for *E. coli* MG1655. Ethylene production as a function of IPTG concentration for strains containing the original controller plasmid, N249, or the improved plasmid pCV27002. Error bars represent sample standard deviation from four measurements.

Figure 15A:
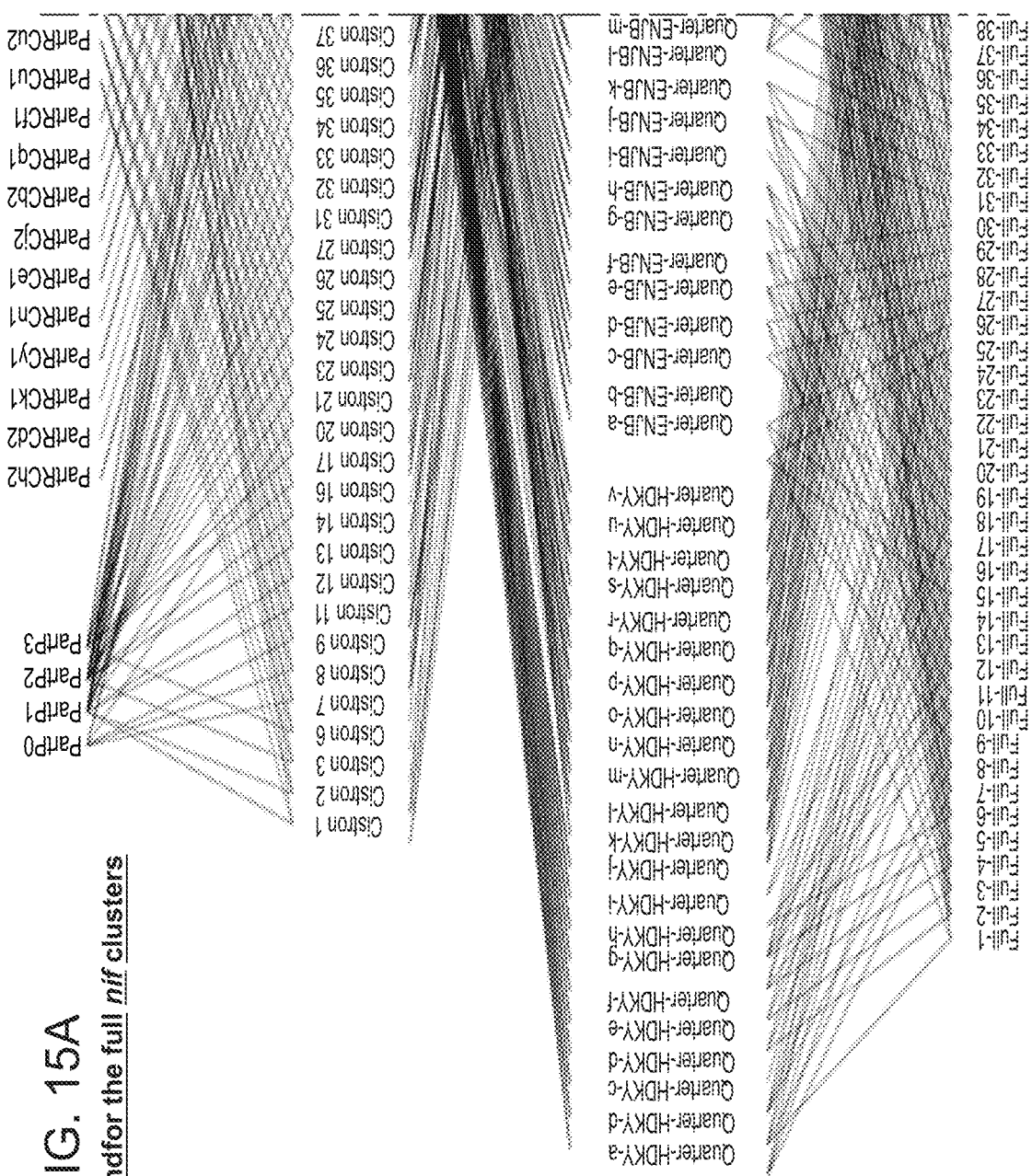
Figure 15B:
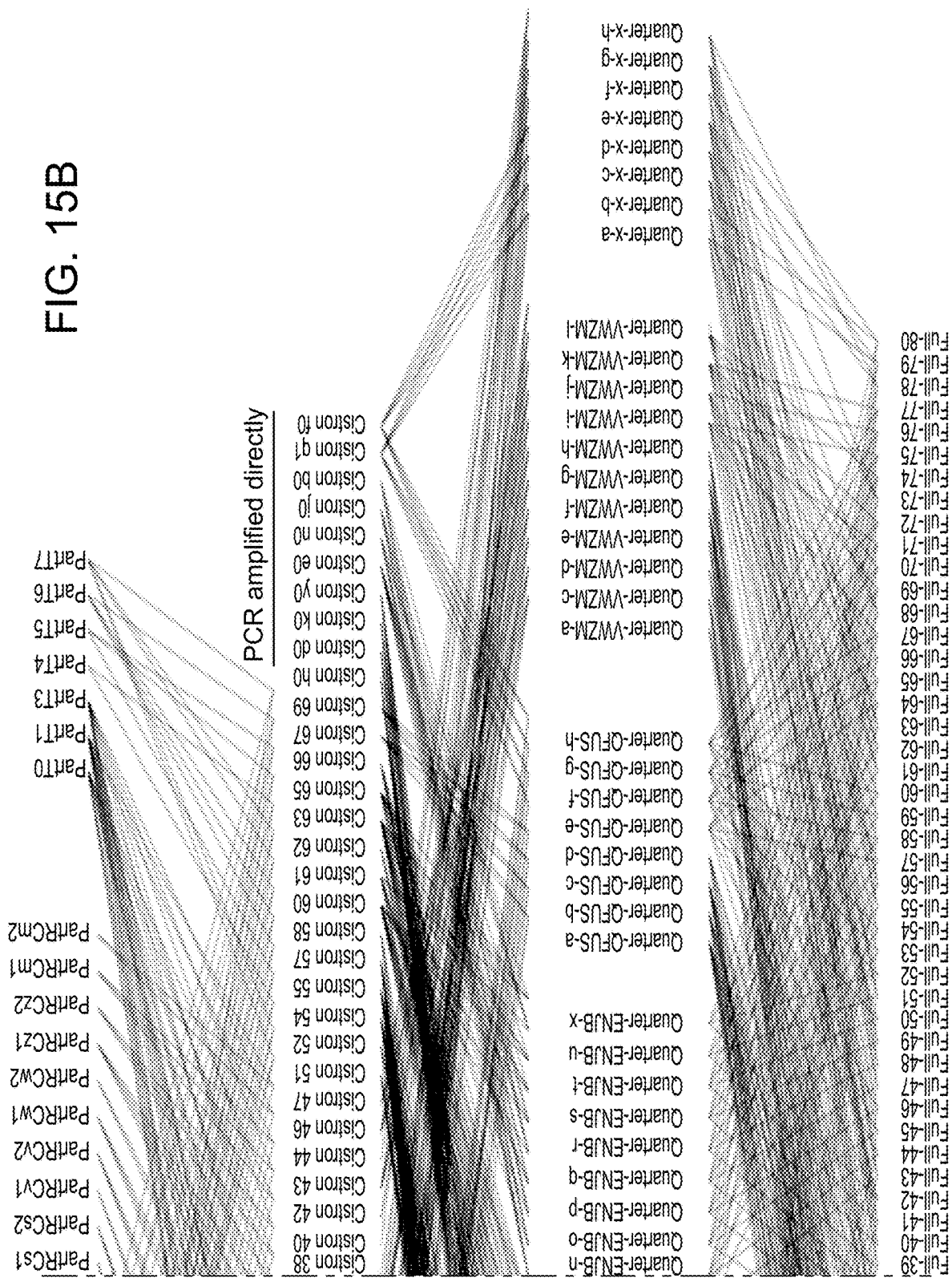

FIGS. 15A-15B depict an assembly graph for full nitrogenase gene cluster, with lines showing compositional relationship from base parts (top) through cistrons, quarter-clusters, and full clusters (bottom).

Figure 16A:
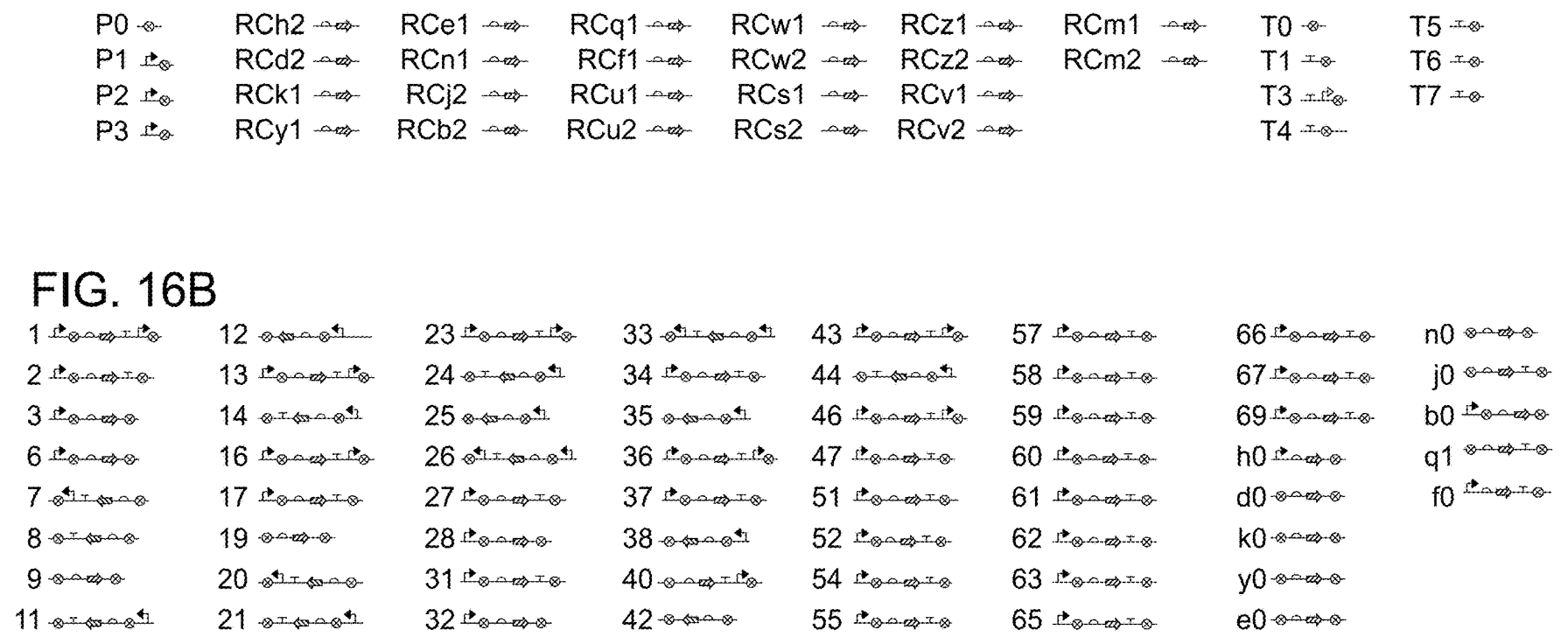
Figures 6D, 16C:
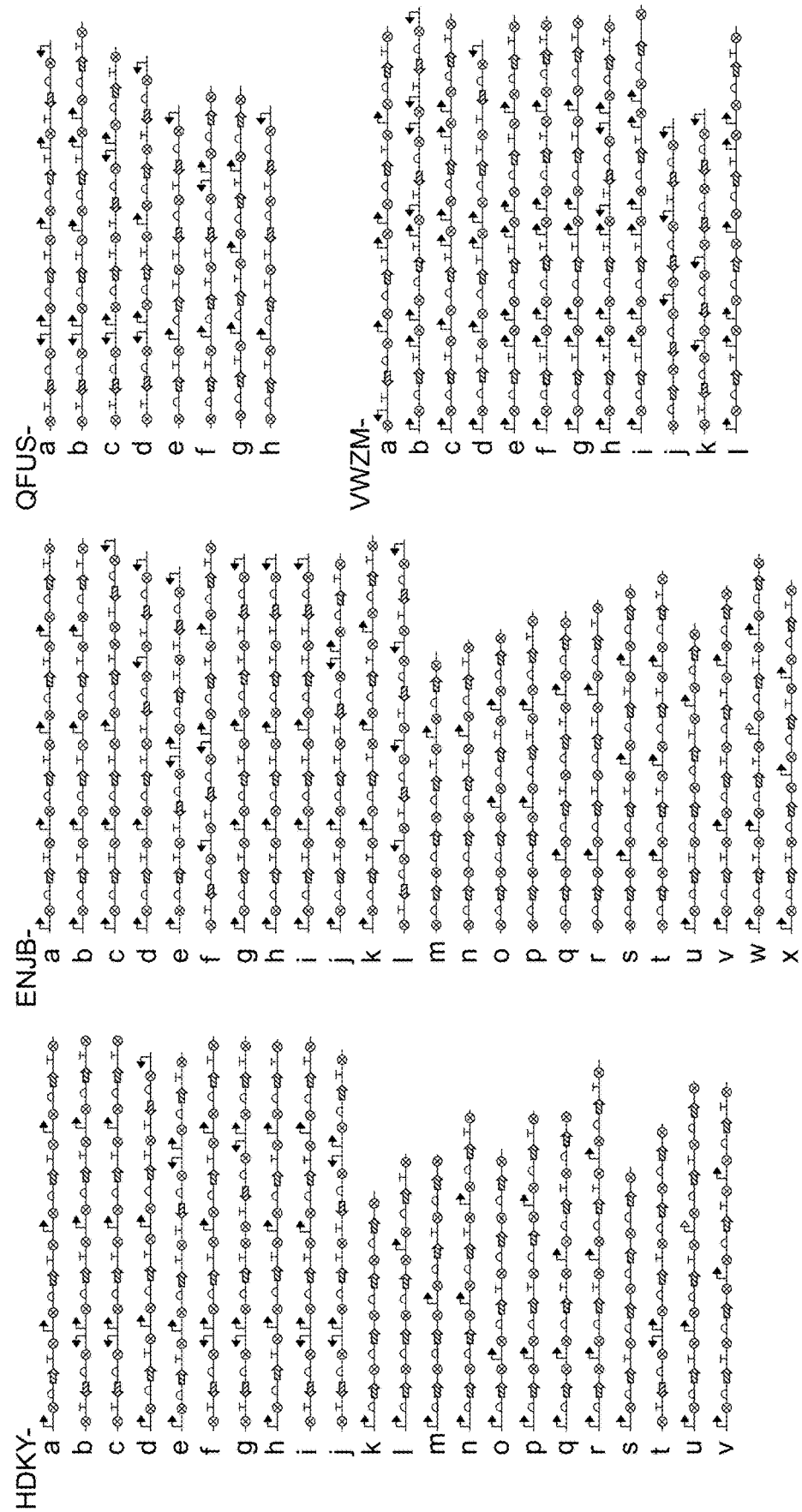
Figure 16D:
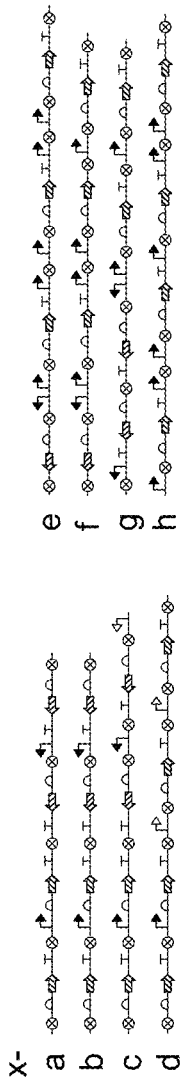

FIG. 16A depicts icon representations of the base parts used during construction of the full nif gene cluster library, including base parts. FIG. 16B shows the cistron parts used during library construction. FIGS. 16C-16D show quarter-cluster parts from library construction. Quarter-cluster parts are grouped by gene content with the last group (x-) constituting non-standard gene groupings resulting from direct incorporation of nifUSVWZM library clusters. Parts correspond to the assembly graph in FIGS. 15A-15B.

Figure 17B:
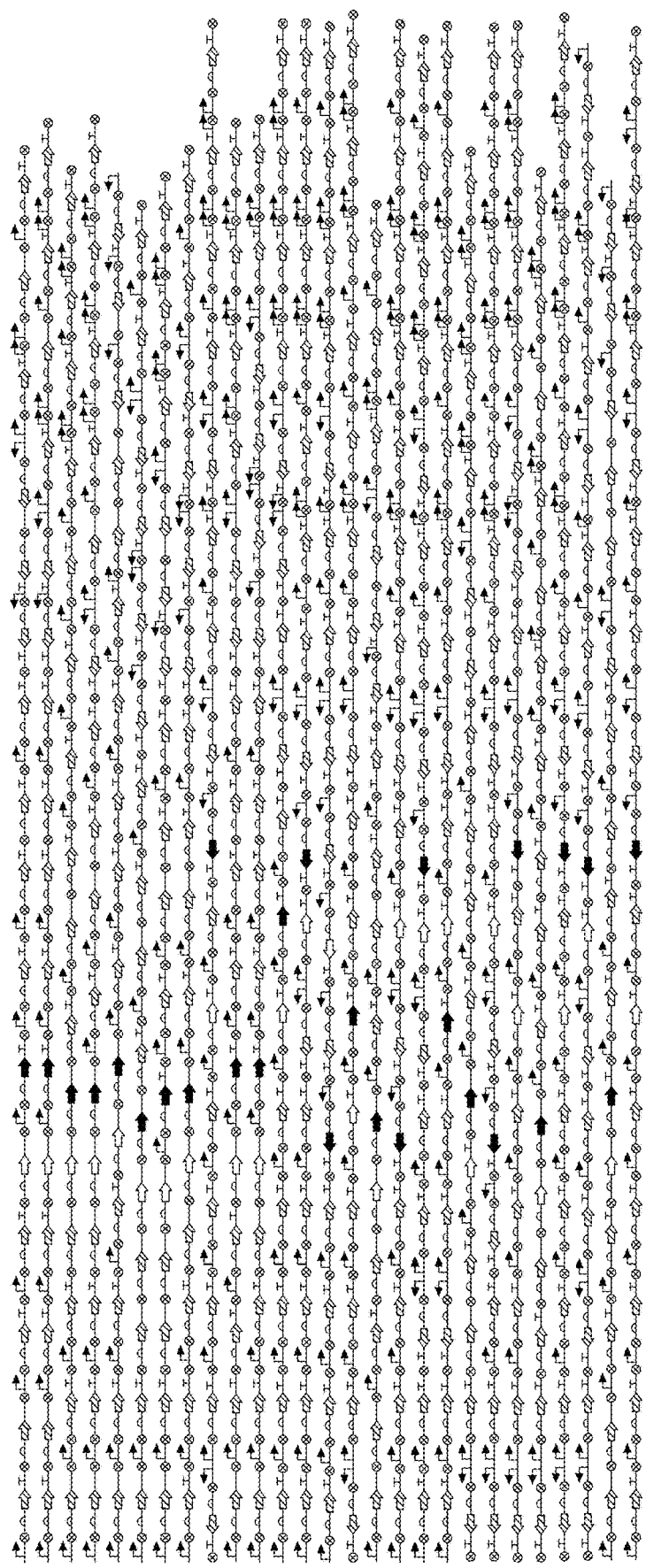
Figure 17C:
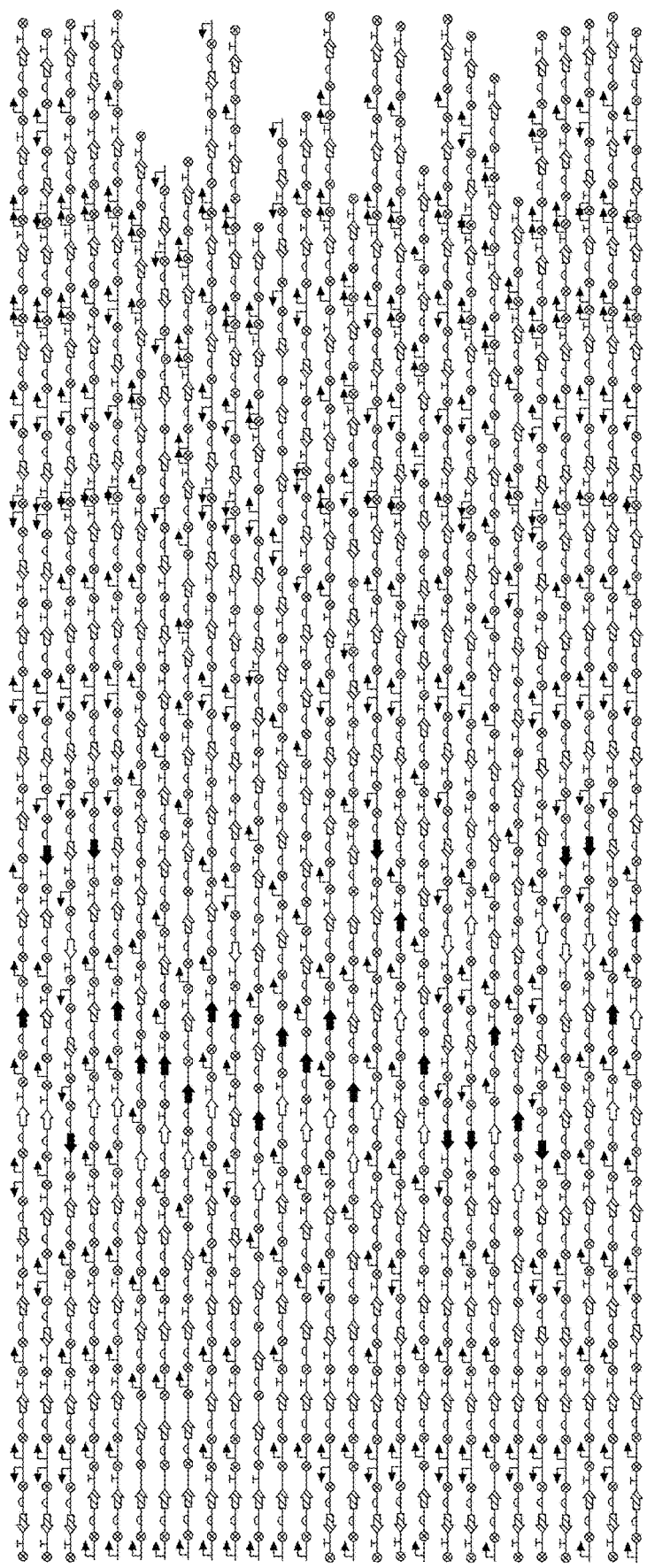

FIGS. 17A-17C schematically present the highlighted organization of nifE and nifN in full nif gene clusters that are shown in rank order according to nitrogenase activity.

Figures 18A, 18B, 18C:
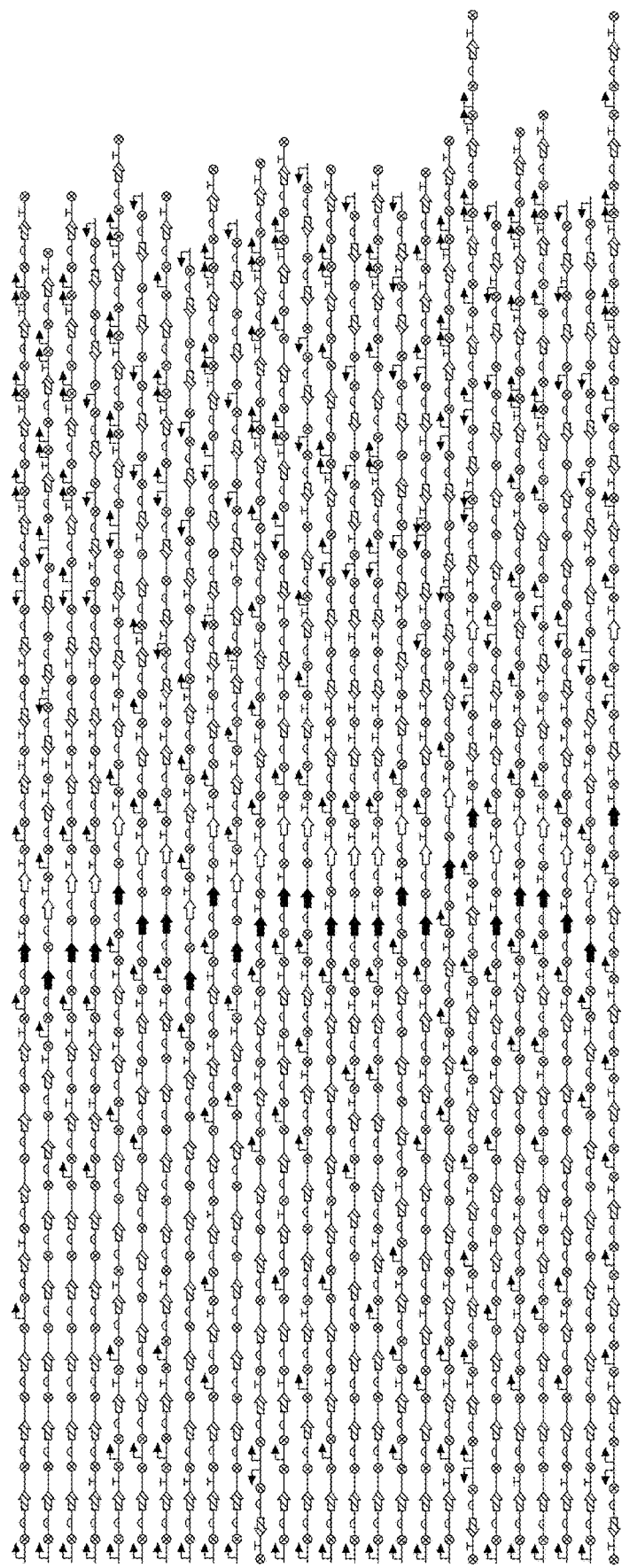
Figure 18B:
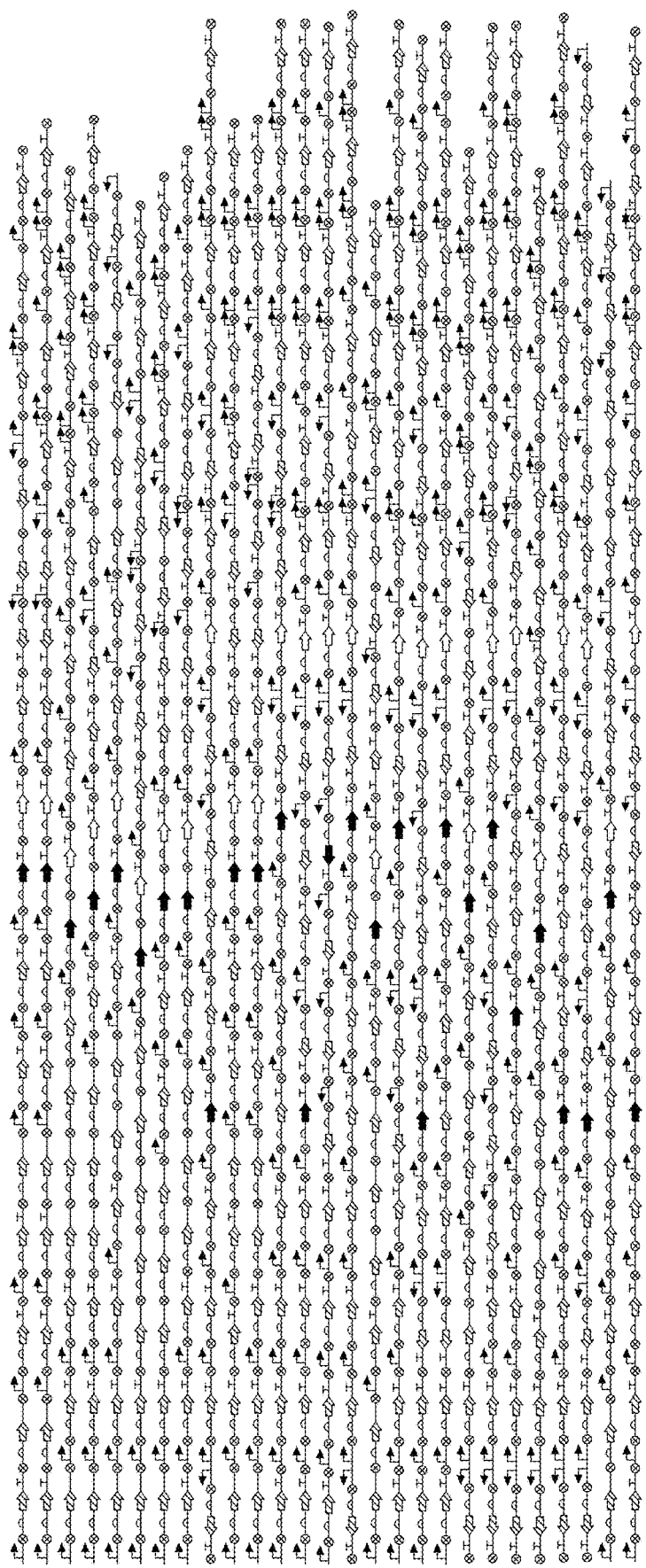
Figure 18C:
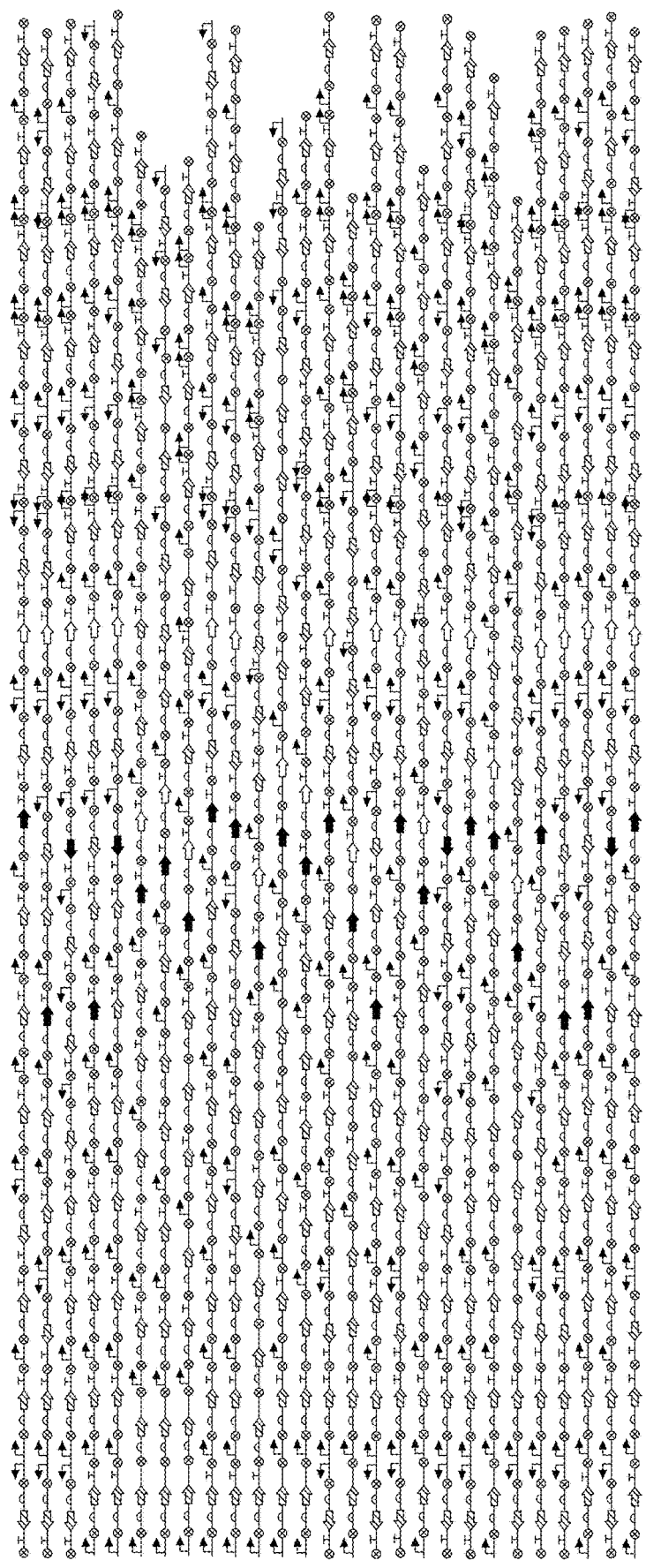

FIGS. 18A-18C schematically present the highlighted organization of nifB and nifQ in full nif gene clusters that are shown in rank order according to nitrogenase activity.

Figure 19A:
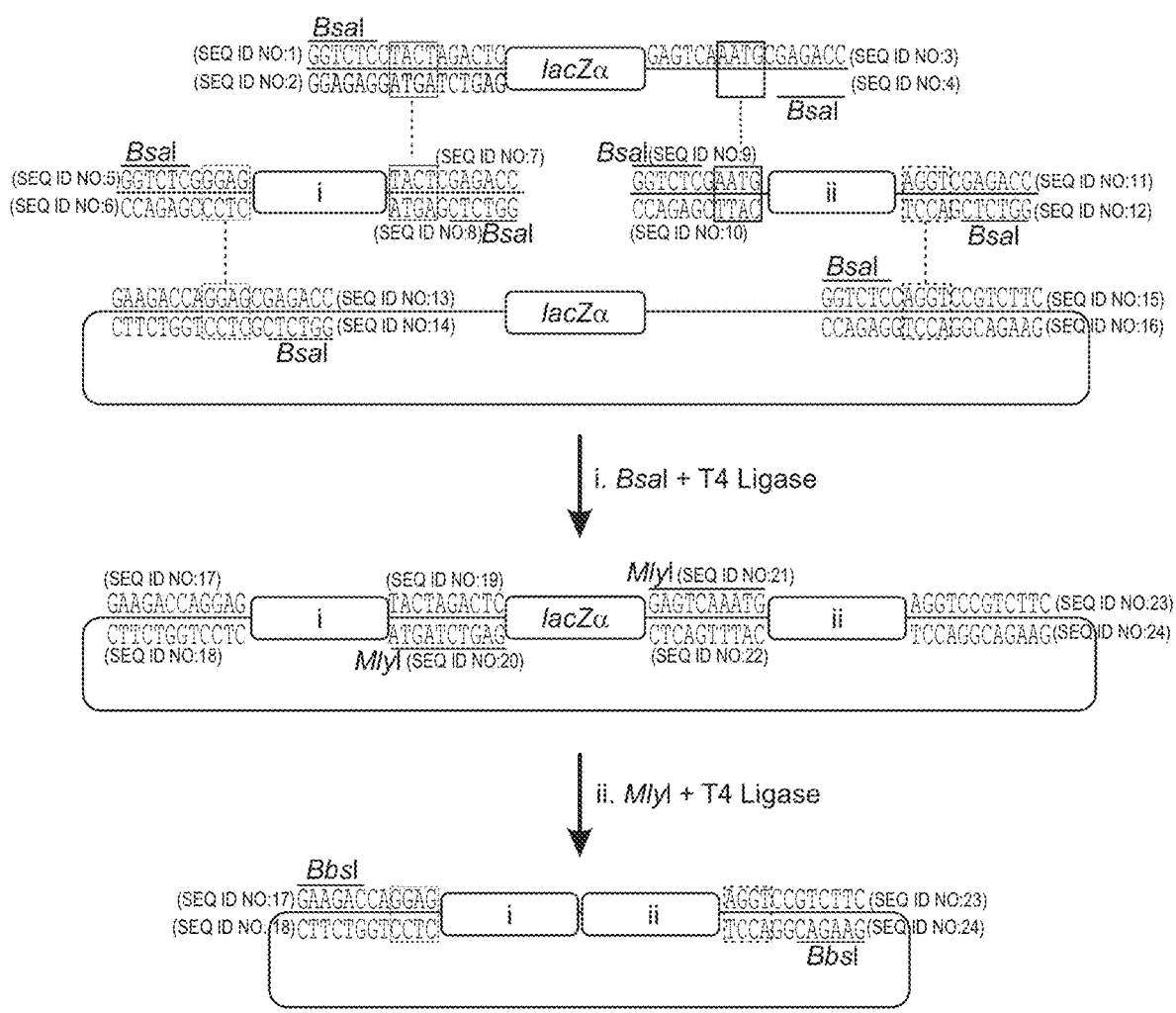
Figure 19B:
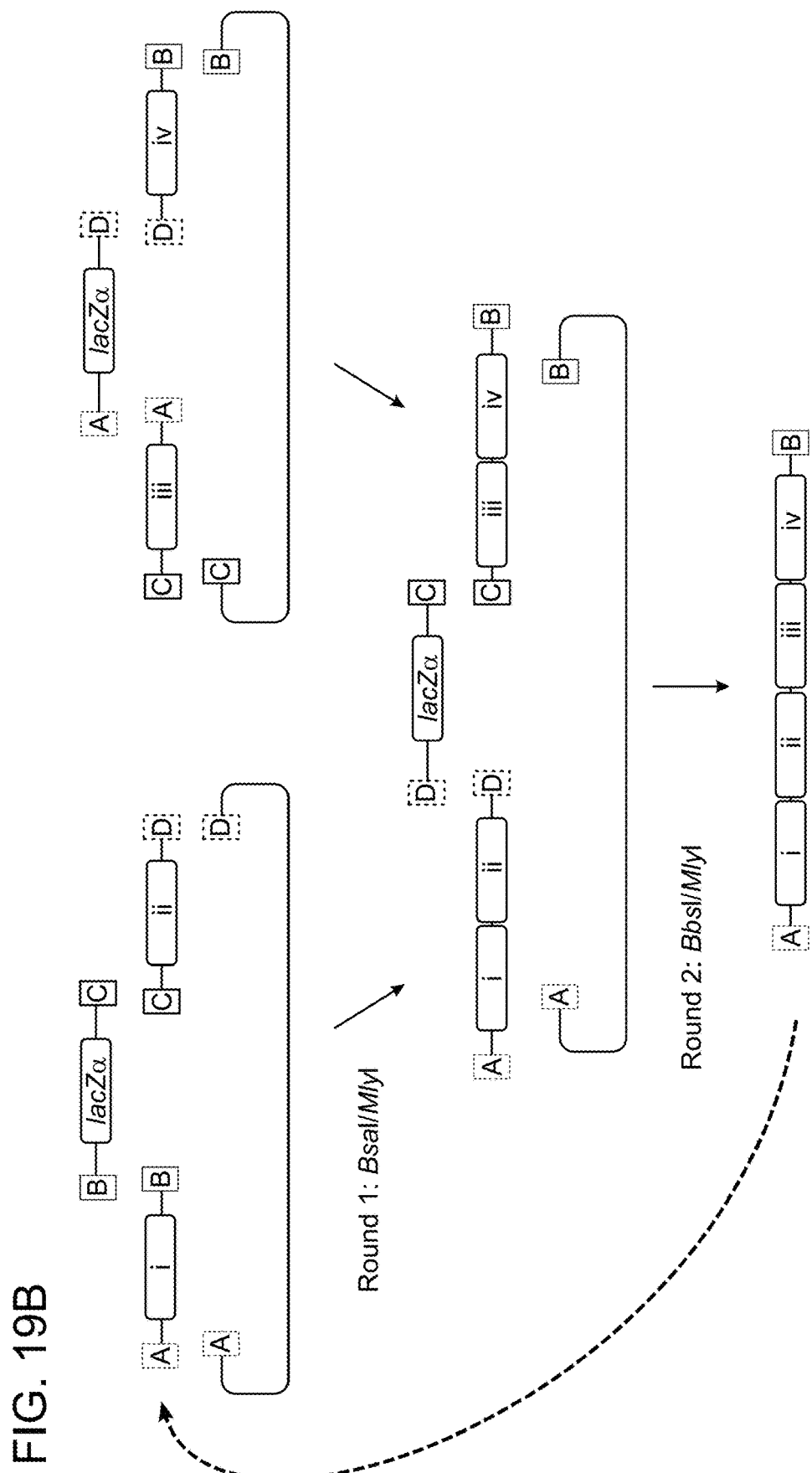

FIG. 19A presents a schematic depiction of the Scarless Stitching method including sequence-level details for joining two parts (numbered boxes) with cohesive ends generated during initial restriction digestion/ligation reaction highlighted with boxes. FIG. 19B presents a schematic drawing of two full founds of Scarless Stitching illustrates possible organization of cohesive ends, here represented simply by one-letter codes A-D, to direct the assembly of a four-part design. Dotted arrow shows where the final product could be re-inserted for additional rounds.

Figure 20:
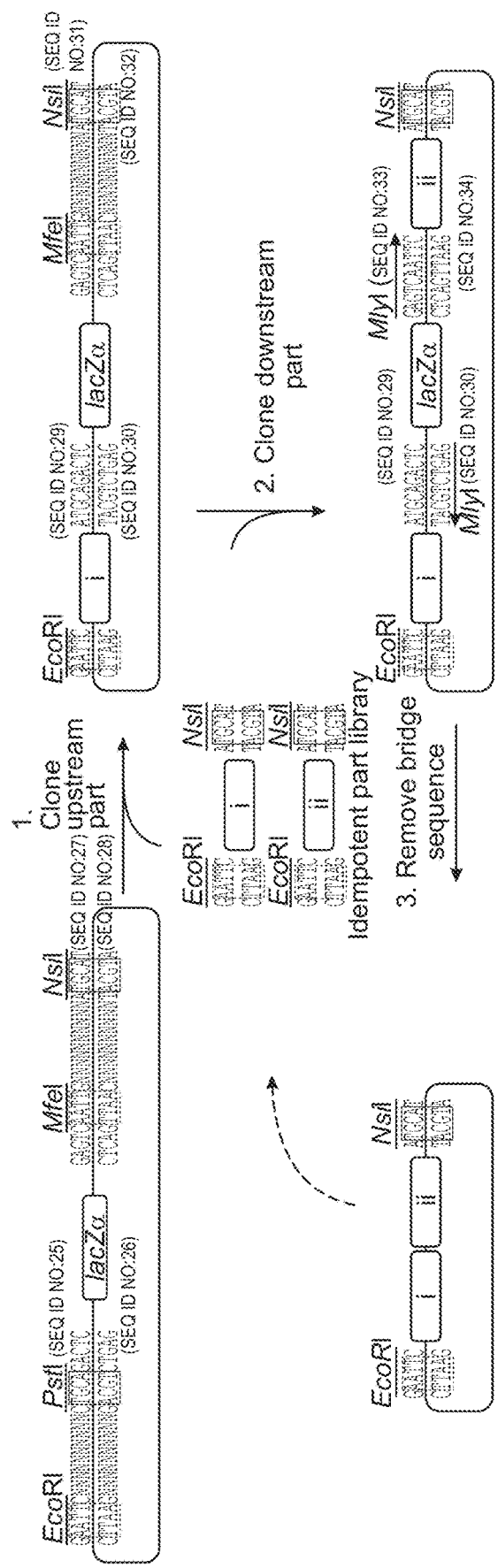

FIG. 20 shows the designed idempotent version of Scarless Stitching including sequence-level representation of a itempotent cloning technique with restriction recognition sites labeled and cohesive ends generated during cloning highlighted with boxes. Dotted arrow shows that final product can be placed back into indempotent part library for further concatenation.

Figure 21:
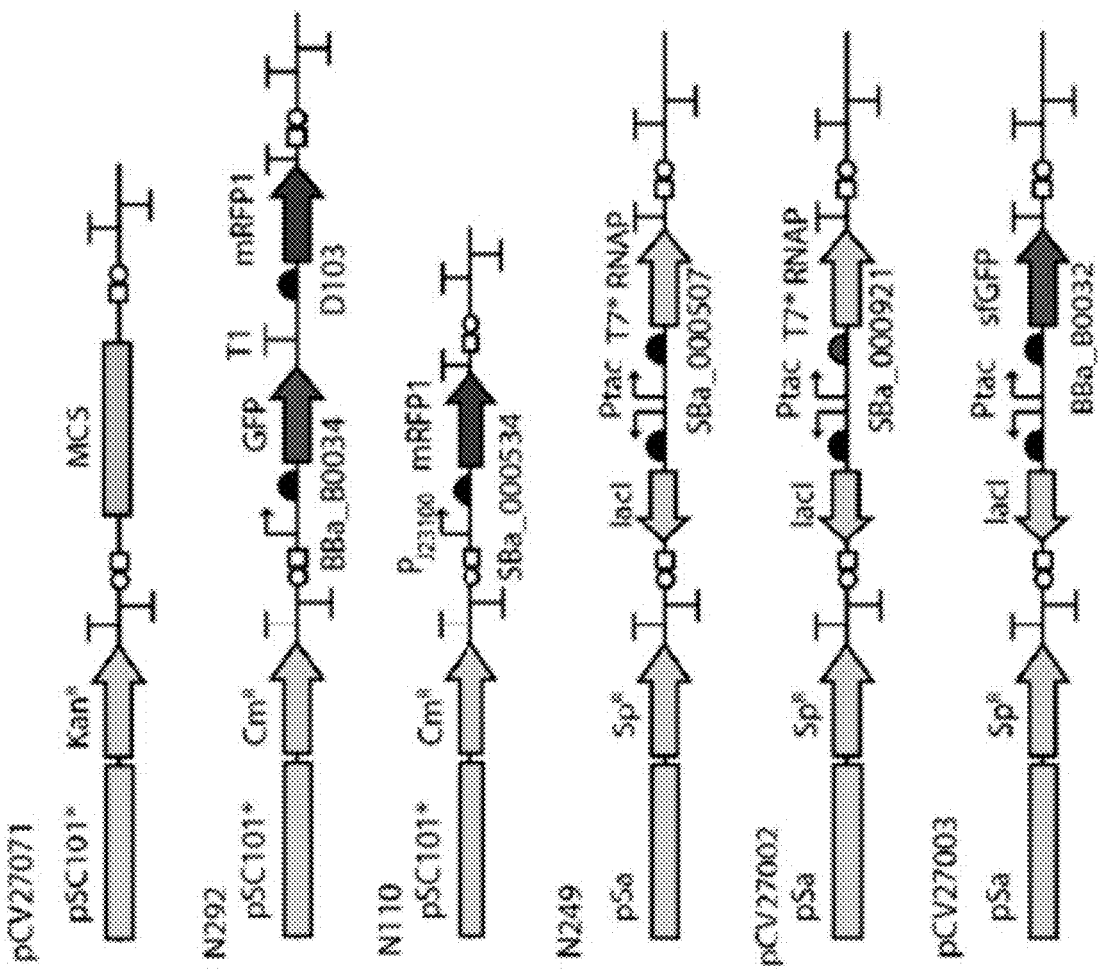

FIG. 21 presents maps for key plasmids used in the presented examples. Genetic parts are labeled above or below construct, and BioBrick prefix and suffix are denoted with open square and circle, terminator parts are in the shape of a T.

Figure 22:
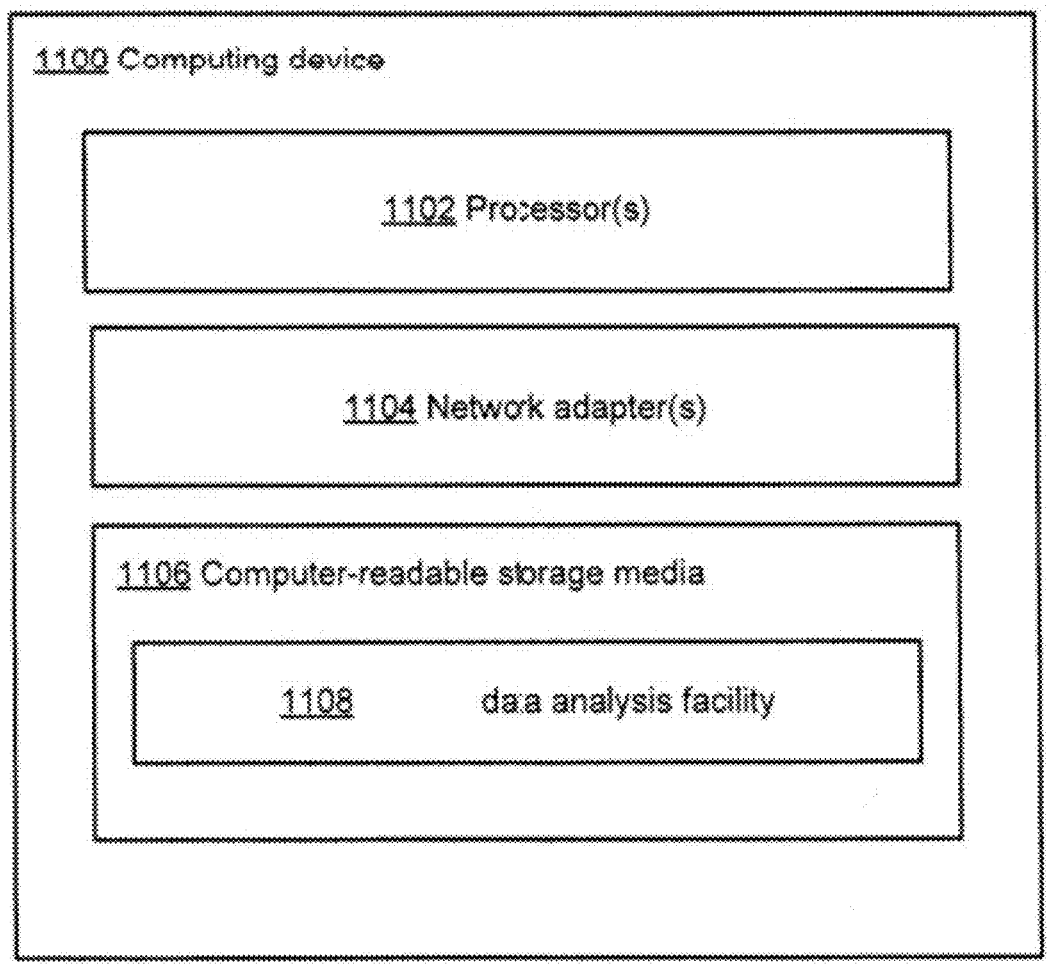

FIG. 22 is a block diagram illustrating an exemplary computing device in which some embodiments may be implemented.

Figure 23:
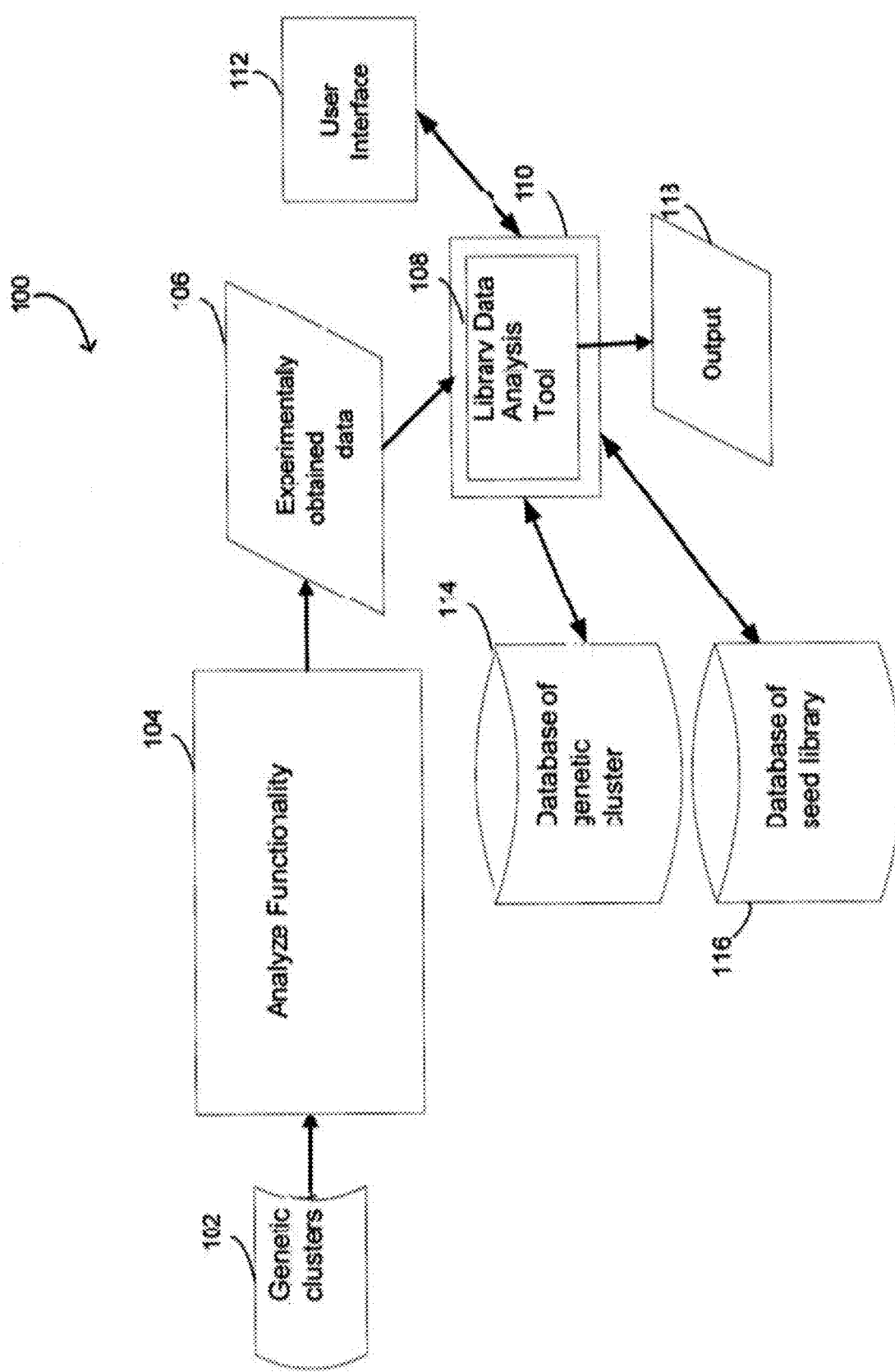

FIG. 23 is a flow chart showing an exemplary process for generation and processing of information.

DETAILED DESCRIPTION

The invention in some aspects relates to new methods for generating highly diverse sets of nucleic acids in a rapid high throughput manner. The new methods are demonstrated herein using a refactored nitrogen fixation (nif) gene cluster to build permutations that have radically reorganized genetics that could not be achieved starting from a wild-type cluster.

The methods of the invention may be used to generate a multitude of different gene systems. The ability to develop highly diverse molecules in a rapid high throughput manner has many advantages. For instance, clusters of genes may be optimized to produce altered functionality resulting in different activity levels and profiles. As shown in the examples below, in one experiment, more than 80 variants of the nifUSVWZM operon were constructed each differing in regulatory parts and architecture (gene order, orientation, operon occupancy) from one another. Even with dramatic changes a number of the constructs exhibited activity, and one of the structures even achieved 100% of the native nif activity, although it had an orientation reversal. A second library of 80 clusters that scrambled the architecture of all 16 essential nif genes (~2 Mb of DNA assembly) was built. Interestingly, the most functional variants had no aspects of the wild-type architecture conserved. This work demonstrated a surprising plasticity in the genetic organization of gene clusters and underscores the value of refactoring as a tool for a multitude of uses such as hypothesis testing and genetic optimization.

The refactoring process involves several levels of restructuring the genetic clusters. For example, the codons of essential genes in a genetic cluster are changed to create a DNA sequence as divergent as possible from the wild-type (WT) gene. This may be achieved through codon optimization. Recoded genes are computationally scanned to identify internal regulators. These regulatory components may then be removed. They are organized into operons and placed under the control of synthetic parts (promoters, ribosome binding sites, and terminators) that are functionally separated by spacer parts. Finally, a controller consisting of genetic sensors and circuits that regulate the conditions and dynamics of gene expression is added. As shown in the examples, this approach has been applied to an agriculturally relevant gene cluster from *Klebsiella oxytoca* encoding the nitrogen fixation pathway for converting atmospheric N2 to ammonia. The native gene cluster consists of 20 genes in seven operons and is encoded in 23.5 kb of DNA. The methods of the invention have enabled the construction of a "refactored" gene cluster that shares little DNA sequence identity with the wild type (WT)

Thus, the invention includes methods for producing libraries of genetic components, including diverse genetic libraries and diverse seed libraries. The method for producing diverse genetic libraries includes identifying a target genetic cluster of genes, producing a plurality of distinct non-naturally occurring genetic clusters from the target genetic cluster by preparing a plurality of modular units from one or more genetic components using a scarless stitching assembly, reassembling the modular units in a plurality of distinct patterns to produce the plurality of distinct non-naturally occurring genetic clusters, wherein the plurality of distinct non-naturally occurring genetic clusters form the diverse genetic library.

As used herein, a "genetic cluster" refers to a set of two or more genes that encode gene products. A target, naturally occurring, or wild type genetic cluster is one which serves as the original model for the refactoring. In some embodiments, the gene products are enzymes. In some embodiments, the gene products of a cluster function in a biosynthetic pathway. Gene clusters appropriate for practice of the invention described herein will be clear to one of ordinary skill in that art. In some embodiments, the gene cluster that is refactored is the nif nitrogen fixation pathway. Non-limiting examples of gene clusters include pathways for the synthesis of amino acids or amino acid derivatives, such as the 6-aminocaproic acid pathway; pathways for the synthesis of antibiotics; pathways for the synthesis of metabolites, such as the spectinabilin pathway; pathways for the degradation of molecules, such as the alkyxanthine degradation pathway.

The genetic clusters may encode proteins of a biosynthetic pathway. A biosynthetic pathway, as used herein, refers to any pathway found in a biological system that involves more than one protein. In some instances these pathways involve 2-1,000 proteins. In other instances the number of proteins involved in a biosynthetic pathway may be 2-500, 2-100, 5-1000, 5-500, 5-100, 5-10, 10-1,000, 10-900, 10-800, 10-700, 10-600, 10-500, 10-400, 10-300, 10-200, 10-100, 50-1,000, 50-500, 50-100, 100-1,000, or 100-500. Examples of biosynthetic pathways include but are not limited to the nitrogen fixation pathway, The naturally occurring genetic cluster is used as a template to design a plurality of distinct non-naturally occurring genetic clusters. The plurality of distinct non-naturally occurring genetic clusters refers to at least 2. In some instances the plurality is 5-1,000, 5-100, 5-500, 10-1,000, 10-500 or 10-100. A non-naturally occurring genetic cluster, as used herein refers to a genetic cluster that has at least two of the genes found in the corresponding genetic cluster. In some instances the non-naturally occurring genetic cluster will have at least 50%, at least 60%, at least 70%, at least 80%, at least 90%, at least 95% or 100% of the genes found in the corresponding naturally occurring genetic cluster. While the non-naturally occurring genetic cluster has at least two of the genes found in the naturally occurring molecule, those genes may differ in nucleotide sequence, position and/or orientation from the naturally occurring molecule.

The synthetic nucleic acids created by the methods of the invention can be used to produce genetically modified organisms including modified bacteria, yeast, mammals, plants, and other organisms. Genetically modified organisms may be used in research (e.g., as animal models of disease, as tools for understanding biological processes, etc.), in industry (e.g., as host organisms for protein expression, as bioreactors for generating industrial products, as tools for environmental remediation, for isolating or modifying natural compounds with industrial applications, etc.), in agriculture (e.g., modified crops with increased yield or increased resistance to disease or environmental stress, etc.), and for other applications. These synthetic nucleic acids also may be used as therapeutic compositions (e.g., for modifying gene expression, for gene therapy, etc.) or as diagnostic tools (e.g., as probes for disease conditions, etc.).

As used herein "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. The nucleotide sequences are displayed herein in the conventional 5'-3' orientation.

Each genetic cluster is organized into transcriptional units which are composed of a plurality of modular units. A modular unit is a discreet nucleic acid sequence that is made up of one or more genetic components. A genetic component may include anything typically found in a genetic fragment. For instance a genetic component incudes but is not limited to genes, regulatory elements, spacers, non-coding nucleotides. Some or all of these are found within each modular unit. Within the modular unit one or more of the synthetic regulatory elements may be genetically linked to one or more protein coding sequences of the genetic cluster.

While multiple modular units may be composed of the same gene and regulatory elements, the units may differ from one another in terms of the orientation, position, number etc. of the gene and regulatory elements. Other modular units may have some elements in common with other modular units but include some different elements. Yet other modular units may be completely distinct and do not overlap with other modular units. The great diversity of the modular units is what leads to the diversity of the assemble d genetic clusters in a library.

The modular units within the genetic cluster are arranged such that the plurality of distinct non-naturally occurring genetic clusters are distinct from a naturally occurring genetic cluster based on the number, the order, and/or the orientation of particular genetic components. The number of genetic components within a modular unit may be easily varied. For instance, one modular unit may have a single promoter or terminator, whereas another modular unit may have 5 promoters and 2 terminators. The variation that may be achieved by manipulation of this factor is significant. Additionally the order of the components within a modular unit may be varied dramatically. Multiple sets of modular units may be generated where a single order of two components may be switched. This factor would also generate significant diversity. Switching the orientation of a component in the modular unit is also a viable way of generating diversity. While it may be expected that switching the orientation of one or more genetic components might interfere with functionality it has been demonstrated herein that genetic clusters having different orientation are actually functional.

In some instances the refactored genetic clusters of the library have naturally occurring non-coding DNA, naturally occurring regulatory sequences, and/or non-essential genes that have been removed from at least one or in some instances all of the transcriptional units. These may be replaced by synthetic regulatory sequences, not replaced at all or replaced by spacers. A spacer simply refers to a set of nucleotides or analogs thereof that don't have a function such as coding for a protein or in any way regulating the activity of the gene cluster.

One or more genes typically are included in a modular unit. The genes correspond to the genes in the naturally occurring genetic cluster and they may in some instances, have the identical sequence and/or position and or/orientation to the naturally occurring molecule. However in some in instances the genes in the modular units vary by one or more of these factors. When a gene has a different nucleotide sequence from the naturally occurring gene, it may be that the gene is transcribed into the same set of amino acids as that of the naturally occurring protein. This can occur when the gene has different nucleotides that produce the same codon. A codons refers to a trinucleotide sequence that is specific for a specific amino acid. This variability can be captured by randomized codons. This means that the nucleotide sequence can be specifically designed to include a different nucleotide sequence, but one which encodes the exact same amino acids. In some instances, the nucleotide sequence can be varied to capture amino acids falling within similar structural and or charge groups, in order to produce proteins which may be similar but have some differences.

Thus, in some instances, the genes may be designed to encode proteins having conservative amino acid substitutions to provide functionally equivalent variants, or homologs of the proteins. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

The genetic components in the genetic cluster typically will include at least one synthetic regulatory element. A synthetic regulatory element is any nucleic acid sequence which plays a role in regulating gene expression and which differs from the naturally occurring regulatory element. It may differ for instance by a single nucleotide from the naturally occurring element. Alternatively it may include one or more non-natural nucleotides. Alternatively it may be a totally different element. In each case, it may be considered to be an exogenous regulatory element (i.e. not identical to the naturally occurring version). Thus, a "regulatory element" refers to a nucleic acid having nucleotide sequences that influence transcription or translation initiation or rate, or stability and/or mobility of a transcription or translation product. Regulatory regions include, without limitation, promoter sequences, ribosome binding sites, ribozymes, enhancer sequences, response elements, protein recognition sites, inducible elements, protein binding sequences, 5' and 3' untranslated regions (UTRs), transcriptional start sites, transcription terminator sequences, polyadenylation sequences, introns, and combinations thereof.

In some embodiments, the regulatory sequence will increase the expression of a gene. In other embodiments, the regulatory sequence will decrease the expression of a gene. In some embodiments the regulatory sequence may be a protein-binding sequence, for example a transcription factor binding site. In some embodiments, the regulatory sequence may be a polymerase-binding site. In some embodiments, the regulatory sequence is a terminator. The terminator may require an additional factor to indicated the end of the sequence for transcription, for example a rho-dependent terminator. In some embodiments, a regulatory sequence is a sequence that binds a ribosome, such as a ribosome-binding site (RBS). In some embodiments, the regulatory sequence indicates where translation will begin. It will be evident to one of ordinary skill in the art that regulatory sequences differ in their strength of regulation. For example, there exist strong promoter sequences, gene expression from which is higher than gene expression from a weak promoter sequence. Similarly, there exist strong RBS sequences that recruit and bind ribosomes with higher affinity than a RBS sequence that is characterized as weak. In some embodiments, the regulatory sequence may be an inducible or conditional regulatory sequence. In some embodiments, the regulatory sequence will exist 5' or upstream of a protein-coding sequence. In other some embodiments, the regulatory sequence will exist 3' or downstream of a protein-coding sequence. In still other embodiments, the regulatory sequence may be present within a protein-coding sequence. Any given protein-coding sequence may be regulated by one or more regulatory sequences. Non-limiting examples of regulatory sequences include the bacteriophage T7 promoter, sigma 70 promoter, sigma 54 promoter, lac promoter, rho-dependent terminator, stem-loop/rho-independent terminator.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid also can be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. The exogenous elements may be added to a construct, for example using genetic recombination. Genetic recombination is the breaking and rejoining of DNA strands to form new molecules of DNA encoding a novel set of genetic information.

"Expression" refers to the process of converting genetic information of a polynucleotide into RNA through transcription, which is catalyzed by an enzyme, RNA polymerase, and into protein, through translation of mRNA on ribosomes.

Promoters may be constitutive or inducible. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268:1766-1769 (1995), see also Harvey et al, Curr. Opin. Chem. Biol., 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J. Clin. Invest., 100:2865-2872 (1997)]. Still other types of inducible promoters which may be useful in this context are those which are regulated by a specific physiological state, e.g., temperature, acute phase, a particular differentiation state of the cell, or in replicating cells only.

The regulatory elements may be in some instances tissue-specific. Tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, a insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some instances the modular units or genetic clusters may be designed to lack in restriction recognition sites. Restriction endonucleases cleave DNA with extremely high sequence specificity and due to this property they have become indispensable tools in molecular biology and molecular medicine. Over three thousand restriction endonucleases have been discovered and characterized from a wide variety of bacteria and archae. Comprehensive lists of their recognition sequences and cleavage sites can be found at REBASE.

Some aspects of the invention pertain to transcription and translation of a genes As used herein, a gene or a RNA transcribed from a DNA sequence is referred to as "monocistronic" if upon transcription only one protein is encoded on a molecule of RNA. Also used herein, "polycistronic" refers to a gene or a RNA transcribed from DNA sequence that encodes more than protein. In some embodiments, genes referred to as polycistronic exist within an operon structure. In some embodiments, expression of genes within an operon are regulated by the same one or more regulatory sequence(s).

The genetic clusters of the invention may be expressed in vivo in an organism or in vitro in a cell. The organism or cell may be any organism or cell in which a DNA can be introduced. For example, organisms and cells according to the invention include prokaryotes and eukaryotes (i.e. yeast, plants). Prokaryotes include but are not limited to Cyanobacteria, *Bacillus subtilis, E. coli, Clostridium*, and *Rhodococcus*. Eukaryotes include, for instance, algae (*Nannochloropsis*), yeast such as, *S. cerevisiae* and *P. pastoris*, mammalian cells, such as for instance human cells, primary stem cell lineages, embryonic stem cells, adult stem cells, rodents, and plants. Thus, some aspects of this invention relate to engineering of a cell to express proteins from the modified genetic clusters.

As used herein the term "isolated nucleic acid molecule" refers to a nucleic acid that is not in its natural environment, for example a nucleic acid that has been (i) extracted and/or purified from a cell, for example, an algae, yeast, plant or mammalian cell by methods known in the art, for example, by alkaline lysis of the host cell and subsequent purification of the nucleic acid, for example, by a silica adsorption procedure; (ii) amplified in vitro, for example, by polymerase chain reaction (PCR); (iii) recombinantly produced by cloning, for example, a nucleic acid cloned into an expression vector; (iv) fragmented and size separated, for example, by enzymatic digest in vitro or by shearing and subsequent gel separation; or (v) synthesized by, for example, chemical synthesis. In some embodiments, the term "isolated nucleic acid molecule" refers to (vi) an nucleic acid that is chemically markedly different from any naturally occurring nucleic acid. In some embodiments, an isolated nucleic acid can readily be manipulated by recombinant DNA techniques well known in the art. Accordingly, a nucleic acid cloned into a vector, or a nucleic acid delivered to a host cell and integrated into the host genome is considered isolated but a nucleic acid in its native state in its natural host, for example, in the genome of the host, is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein.

Methods to deliver expression vectors or expression constructs into cells, for example, into yeast cells, are well known to those of skill in the art. Nucleic acids, including expression vectors, can be delivered to prokaryotic and eukaryotic cells by various methods well known to those of skill in the relevant biological arts. Methods for the delivery of nucleic acids to a cell in accordance to some aspects of this invention, include, but are not limited to, different chemical, electrochemical and biological approaches, for example, heat shock transformation, electroporation, transfection, for example liposome-mediated transfection, DEAE-Dextran-mediated transfection or calcium phosphate transfection. In some embodiments, a nucleic acid construct, for example an expression construct comprising a fusion protein nucleic acid sequence, is introduced into the host cell using a vehicle, or vector, for transferring genetic material. Vectors for transferring genetic material to cells are well known to those of skill in the art and include, for example, plasmids, artificial chromosomes, and viral vectors. Methods for the construction of nucleic acid constructs, including expression constructs comprising constitutive or inducible heterologous promoters, knockout and knockdown constructs, as well as methods and vectors for the delivery of a nucleic acid or nucleic acid construct to a cell are well known to those of skill in the art, and are described, for example, in J. Sambrook and D. Russell, Molecular Cloning: A Laboratory Manual, Cold Spring Harbor Laboratory Press; 3rd edition (Jan. 15, 2001); David C. Amberg, Daniel J. Burke; and Jeffrey N. Strathern, Methods in Yeast Genetics: A Cold Spring Harbor Laboratory Course Manual, Cold Spring Harbor Laboratory Press (April 2005); John N. Abelson, Melvin I. Simon, Christine Guthrie, and Gerald R. Fink, Guide to Yeast Genetics and Molecular Biology, Part A, Volume 194 (Methods in Enzymology Series, 194), Academic Press (Mar. 11, 2004); Christine Guthrie and Gerald R. Fink, Guide to Yeast Genetics and Molecular and Cell Biology, Part B, Volume 350 (Methods in Enzymology, Vol 350), Academic Press; 1st edition (Jul. 2, 2002); Christine Guthrie and Gerald R. Fink, Guide to Yeast Genetics and Molecular and Cell Biology, Part C, Volume 351, Academic Press; 1st edition (Jul. 9, 2002); Gregory N. Stephanopoulos, Aristos A. Aristidou and Jens Nielsen, Metabolic Engineering: Principles and Methodologies, Academic Press; 1 edition (Oct. 16, 1998); and Christina Smolke, The Metabolic Pathway Engineering Handbook: Fundamentals, CRC Press; 1 edition (Jul. 28, 2009), all of which are incorporated by reference herein.

The present invention includes the individual genetic clusters described herein, as well as libraries of genetic clusters produced by methods described herein and libraries or parts or seeds of the genetic clusters. In some embodiments, the libraries are in solution, or are lyophilized. In some embodiments, the libraries are bound to a substrate, e.g., wherein each member of the library is bound to an individually addressable member, e.g., an individual area on an array (e.g., a microarray), or a bead.

In one embodiment, a genetic clusters includes a nucleotide sequence that is at least about 85% or more homologous or identical to the entire length of a naturally occurring genetic cluster sequence, e.g., at least 5%, 10%, 15%, 20%, 25%, 30%, 35%, 40%, 50% or more of the full length naturally occurring genetic cluster sequence). In some embodiments, the nucleotide sequence is at least about 90%, 91%, 92%, 93%, 94%, 95%, 96%, 97%, 98%, 99% or 100% homologous or identical to a naturally occurring genetic cluster sequence. In some embodiments, the nucleotide sequence is at least about 85%, e.g., is at least about 90%, 91%, 92%, 93%, 94%, 95%, 96%, 97%, 98%, 99% or 100% homologous or identical to a genetic cluster sequence, in a fragment thereof or a region that is much more conserved, such as an essential, but has lower sequence identity outside that region.

Calculations of homology or sequence identity between sequences (the terms are used interchangeably herein) are performed as follows.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

In many cases the nucleic acids described herein having naturally occurring nucleotides and are not modified. In some instances, the nucleic acids may include non-naturally occurring nucleotides and/or substitutions, i.e. Sugar or base substitutions or modifications.

One or more substituted sugar moieties include, e.g., one of the following at the 2' position: OH, SH, $SCH_3$, F, OCN, $OCH_3$ $OCH_3$, $OCH_3$ $O(CH_2)n$ $CH_3$, $O(CH_2)n$ $NH_2$ or $O(CH_2)n$ $CH_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of a nucleic acid; or a group for improving the pharmacodynamic properties of a nucleic acid and other substituents having similar properties. Similar modifications may also be made at other positions on the nucleic acid, particularly the 3' position of the sugar on the 3' terminal nucleotide and the 5' position of 5' terminal nucleotide. Nucleic acids may also have sugar mimetics such as cyclobutyls in place of the pentofuranosyl group.

Nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-T7; and Gebeyehu, G., et al. Nucl. Acids Res., 15:4513 (1987)). A "universal" base known in the art, e.g., inosine, can also be included.

In the context of the present disclosure, hybridization means base stacking and hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as the term is used in the art, refers to the capacity for precise pairing between two nucleotides. For example, if a nucleotide at a certain position of an nucleic acid is capable of hydrogen bonding with a nucleotide at the same position of a second nucleic acid, then the two nucleic acids are considered to be complementary to each other at that position. The nucleic acids are complementary to each other when a sufficient number of corresponding positions in each molecule are occupied by nucleotides that can hydrogen bond with each other through their bases. Thus, "specifically hybridizable" and "complementary" are terms which are used to indicate a sufficient degree of complementarity or precise pairing such that stable and specific binding occurs between the nucleic acids. 100% complementarity is not required.

Techniques operating according to the principles described herein may be implemented in any suitable manner. Included in the discussion above is a description of the steps and acts of various processes that compare and optimize the rapid architectural prototyping of a refactored gene cluster. The processing and decision blocks of these descriptions as well as corresponding flow charts represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 1106 of FIG. 22 described below (i.e., as a portion of a computing device 1100) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, a computer-readable storage medium accessible via one or more networks and accessible by the device/processor, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

FIG. 22 illustrates one exemplary implementation of a computing device in the form of a computing device 1100 that may be used in a system implementing techniques described herein, although others are possible. It should be appreciated that FIG. 22 is intended neither to be a depiction of necessary components for a computing device to operate as an opportunity evaluation system in accordance with the principles described herein, nor a comprehensive depiction.

Computing device 1100 may comprise at least one processor 1102, a network adapter 1104, and computer-readable storage media 1106. Computing device 1100 may be, for example, a desktop or laptop personal computer, a personal digital assistant (PDA), a smart mobile phone, a server, or any other suitable computing device. Network adapter 1104 may be any suitable hardware and/or software to enable the computing device 1100 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 1106 may be adapted to store data to be processed and/or instructions to be executed by processor 1102. Processor 1102 enables processing of data and execution of instructions.

The data and instructions stored on computer-readable storage media 1106 may comprise computer-executable instructions implementing techniques which operate according to the principles described herein. In the example of FIG. 22 computer-readable storage media 1106 stores computer-executable instructions implementing various facilities and storing various information as described above. Computer-readable storage media 1106 may store an MS/MS data analysis facility 1108 which may comprise, for example, computer-executable instructions that, when executed by processor 1102 perform processing in accordance with the techniques as described herein. In some embodiments, the data analysis facility 1108 may comprise computer-executable instructions that, when executed by processor 1102, implements the seed data analysis tool 108 (FIG. 22) to facilitate generation of diverse genetic clusters.

While not illustrated in FIG. 22, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

A goal of the work described herein was to overcome the challenges of engineering complex pathways that are often very large and genetically complex. The current process of genetic design and transfer of a system to a new host, involves the laborious steps of assembling parts into a single construct or the creation of random library with a defined type of diversity (e.g., random mutagenesis or part insertions). The examples of the invention described herein exploit the modularity of a refactored nif gene cluster to build permutations that have dramatically reorganized genetics that could not be achieved starting from the wild-type cluster, as is the typical approach using currently available methods. The methods described within are also useful with any other gene cluster. First, 84 variants of the nifUSVWZM operon were constructed that differ in regulatory parts and architecture (gene order, orientation, operon occupancy). Expression of one of the variant gene clusters achieved 100% of the native nif activity, as measured by an acetylene reduction assay, but this variant contained 5 transcription units and a reversal of gene orientation. A second library of 80 clusters was built that rearranged the architecture of all 16 essential nif genes (~2 Mb of DNA assembly). No aspects of the wild-type architecture were conserved amongst the most functional variants, highlighting the surprising plasticity in the genetic organization of gene clusters that would not have been revealed using currently available genetic engineering approaches The invention described herein implements a multiplexed approach to genetic design, where constructs were generated based on a set of parts and constraints between the parts of the nifUSVWXM operon from *Klebsiella oxytoca*. The nif operon was refactored in these examples by systemically eliminating all native regulation and converting the system to a module set of well-defined and characterized genetic parts (Temme, K., et al., 2012). This involved the elimination of all non-coding DNA and the removal of regulatory and non-essential genes. The 16 essential genes were codon randomized to identify DNA sequences that encode the same amino acid sequence but were as far as possible from the wild-type sequence in order to remove regulation internal to the genes. These genes were organized into operons/transcriptional units under control of T7 RNA polymerase promoters, terminators, and synthetic ribosome binding sites. The transcriptional units of the library that was built incorporated as little pre-conceived design information possible, while maintaining the correct part dependencies required for transcription and translation (FIG. 1). Finally, a controller plasmid was constructed that contains synthetic sensors and circuits and produces an attenuated T7* RNA polymerase that then activates the operons. The method of assembling genetic parts, including genes, promoters, terminators, and RBSs, and the constraints or rule sets of transcription and translation were articulated by the genetic computer programming language EUGENE. This allowed for new constructs to be generated and existing constructs to be scanned to determine if they conform to the rule sets. The success of refactoring the nif pathway of *K. oxytoca* opens up the possibility of engineering other valuable biosynthetic pathways including for the production of pharmaceuticals, insecticides, or herbicides.

Results
Multiplexed Design of Alternative Genetic Encodings of the nifUSVWZM Operon There was little guiding information available regarding the importance of the genetic organization of the native *K. oxytoca* nifUSVWZM operon, so the genetic architecture was allowed to vary considerably. Constructs were allowed that contain different operon structures, gene orders, and changes in orientation. The only architectural constraint that was imposed was to limit nifUSV to the first half of the cluster and nifWZM to the second half to ease the process of assembly (FIG. 1B). Note that this does not mean that these two sets of genes appeared in the same operon. Several non-standard design features were allowed in the library, including tandem promoters, transcriptional interference resulting from converging transcripts, and genes after terminators that rely on read-through for transcription.

Genetic parts were selected to vary the expression levels of component genes across a defined range. Three T7 RNAP promoters were selected to vary transcription (SBa_000920, 0.025±0.009 REU; SBa_000445, 0.084±0.037 REU; and SBa_000446, 0.120±0.041 REU), which covers a range consistent with levels tolerated by the wild-type and refactored clusters 12. The same set of codon-randomized open reading frames for the six genes were used as described previously (Temme, K., et al. 2012). A single terminator was reused through the design (SBa_000450, TS=2.62±0.58) (Chen, Y. J., et al. 2013). A total of 12 RBSs were designed using the RBS Calculator (ref 30) to provide strong and weak RBSs for each gene. This includes six from the original refactored cluster, four that were designed to be 5-fold higher (for nifU, V, W, Z) and two that were designed to be 5-fold weaker (for nifS, M). Seven spacers composed of random 50 bp DNA sequences (randomly generated and then computationally scanned for functional sequences) were included to increase the distance between RBSs and upstream elements and to separate cistron parts (Example 2).

Multiplexed Construction of the nifUSVWZM Library

A hierarchal DNA assembly strategy was developed to efficiently combine genetic parts to form intermediate composite parts and ultimately whole clusters. Each level of the hierarchy uses a different DNA assembly strategy that is optimal for the size and types of parts that exist at that stage (FIG. 1B). At all stages that incorporate diversity, methods were avoided that required oligonucleotide bridges (Gibson, D. G., et al. 2009; Gibson, D. G., et al. 2010; Moon, T. S., et al. 2012; Engler, C., et al. 2008; Noskov, V. N., et al. 2012; de Raad, M., et al. 2013) between parts because the number of oligonucleotides required would become prohibitive in assembling large libraries of highly permuted parts. The first stage combined individual parts (spacers, promoters, RBSs, genes, terminators) to form approximately cistron-sized constructs. At this point, scarless assembly was used in order to avoid the introduction of new sequences at the seams which can have a dramatic impact on activity (Crook, N.C., et al. 2011). We developed a simple "Scarless Stitching" method that is a combinatorial and binary technique using an additional type II restriction endonuclease digestion/ligation reaction to remove the bridging scar (Example 5). In total, 48 unique cistron-level parts were built for the nifUSVWZM library (FIGS. 8A, 8B, and 8C).

The cistron-level constructs were then combined to form half-clusters via the MoClo variation of Golden Gate assembly (Weber, E., et al. 2011; Werner, S., et al. 2012), which provides an easy method to make permutations. While this method is scarless when building a single construct, scars are introduced when building libraries. For the nif libraries, these scars were placed in the spacers that separate cistron parts. After building the cistron parts, one round of PCR was used to customize the flanking regions of each cistron, which contain MoClo cohesive ends that determine the eventual order and orientation in future assembly steps. The cluster assembly was performed in two stages to reduce the number of parts assembled in a single step to <5. Twenty-four half-clusters were built: 12 for nifUSV and 12 for nifWZM. These were then put together in different combinations to build the full clusters using the same assembly process. A total of 84 clusters were designed and built as part of the initial nifUSVWZM library (FIG. 1B).

Screening and Analysis of the nifUSVWZM Library

Figure 2A:
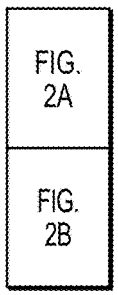
FIGS. 2A-2B depict a rank ordered list of gene clusters and shows their composition and activity based on screening results for the nifUSVWZM library. Gene cluster identity is listed left of the bar graph, and error bars denote sample standard deviation from two replicates. The dashed line denotes the activity of the original synthetic operon. Characterized genetic parts include promoters P1 ($028\pm0.014$ REU; 23 bp), P2 ($0.067\pm0.040$ REU; 23 bp), and P3 ($0.12\pm0.057$ REU; 23 bp), CDSs nifU (825 bp), nifS (1203 bp), nifV (1143 bp), nifW (258 bp), nifZ (447 bp), and nifM (801 bp), terminator T1 (Ts=6.4; 48 bp) and RBSs. RBS sizes range from 31-39 bp.
Figure 2A:
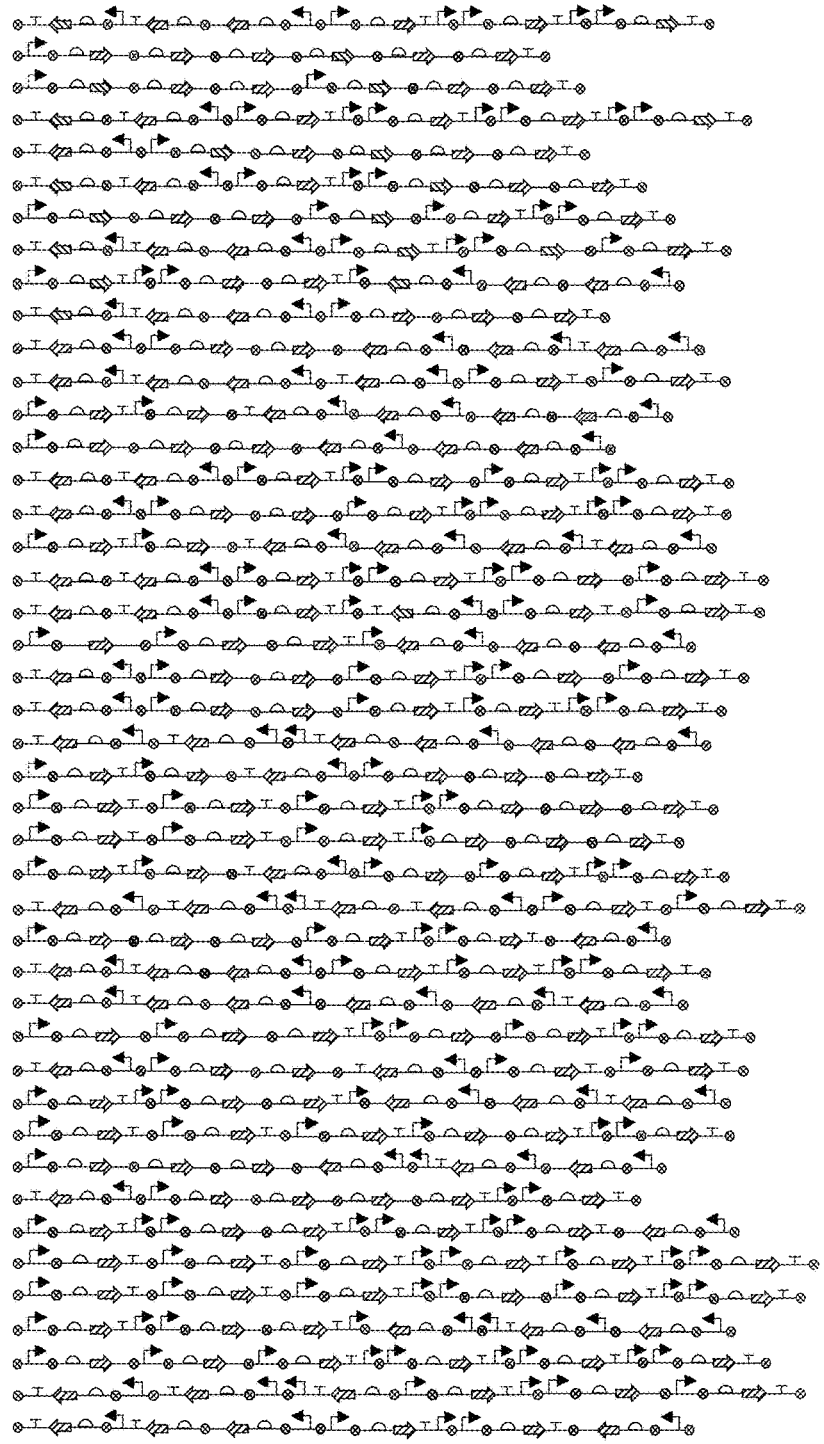
Figure 2A:
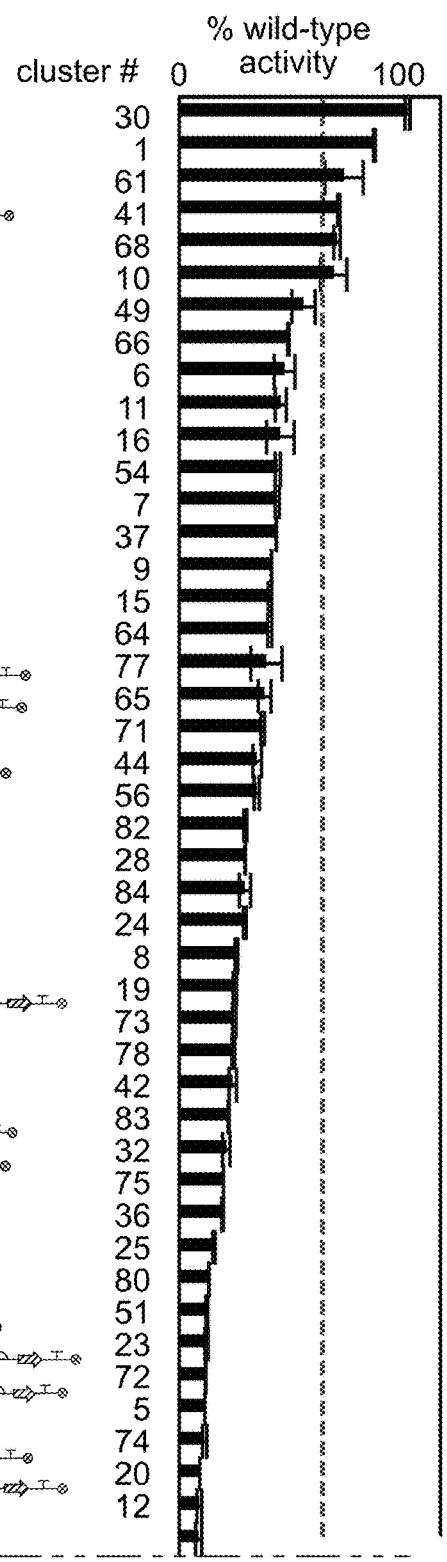

All permuted gene clusters were introduced into *K. oxytoca* NF10 (ΔnifUSVWZM) bearing a controller containing the IPTG-inducible Ptac promoter driving the expression of an attenuated T7* RNAP (plasmid N249) (Temme, K., et al. 2012). Each variant was characterized using an acetylene reduction assay and compared to wild-type *K. oxytoca* M5a1 (FIG. 2A). Under these conditions, the original refactored nifUSVWZM operon is only able to achieve 60%±1.2% activity of the wild-type operon. One variant (USVWZM #30) recovered full wild-type activity (100%±7 1.0%), but had a completely different genetic architecture compared to wild-type, with five transcription units, different gene order and a change in orientation between nifUVS and nifZMW. Additionally, tandem promoters control nifZ and nifM. However, it is noteworthy that the second best operon (USVWZM #1, 87%±0.5%) had the same single-operon architecture as the first refactored version, with only different parts used for RBSs and spacers. The next three variants (USVWZM #61, #41, and #68) had high activity (73%±8.5%, 71%±0.5%, and 70%±1.4%) but also differed significantly in their architectures with (2, 5, and 3) operons and (2, 8 and 4) promoters. The diversity of genetic architectures present in the top-five performing variants highlights the genetic plasticity of this operon.

Figure 2B:
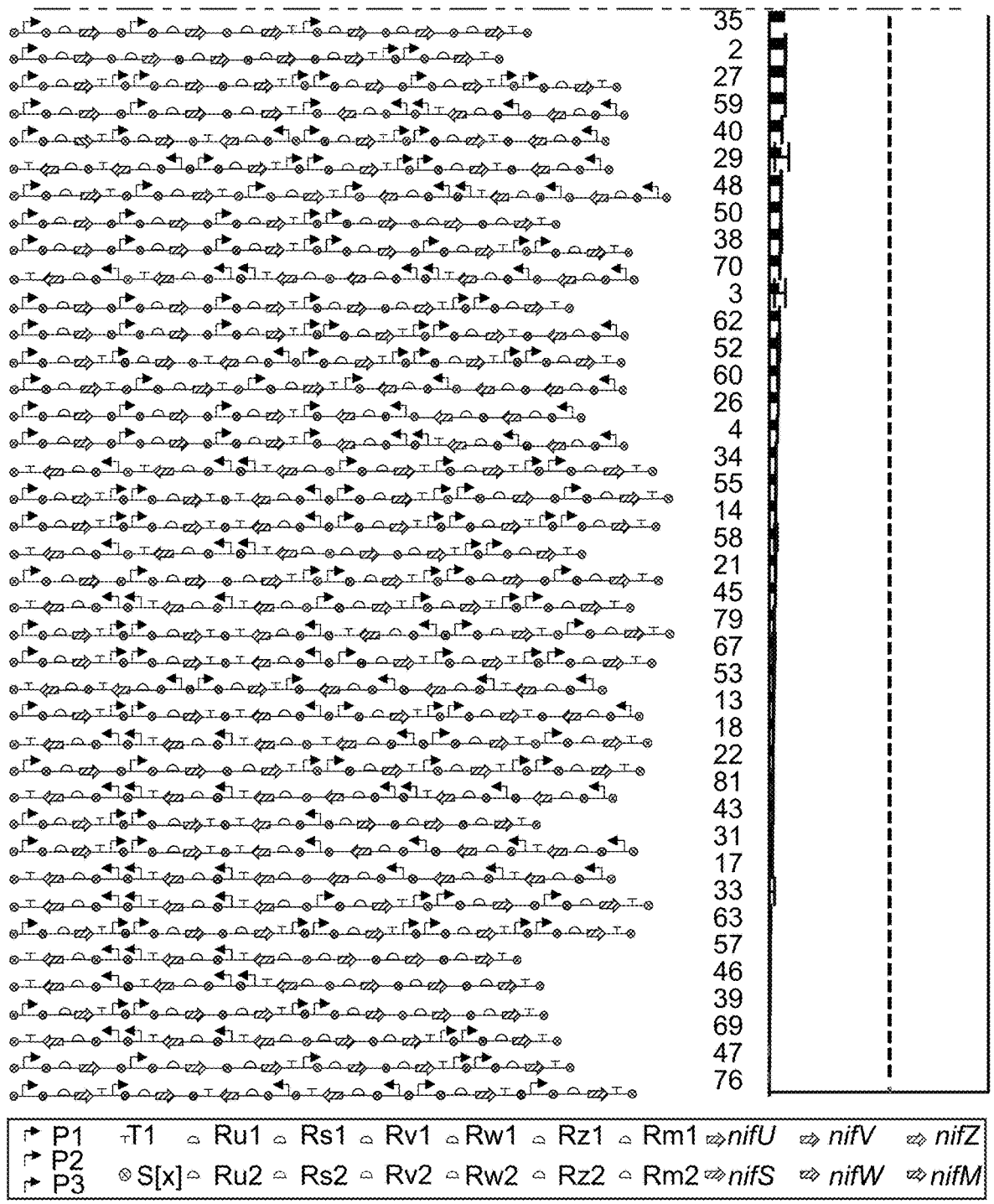
Figure 2C:
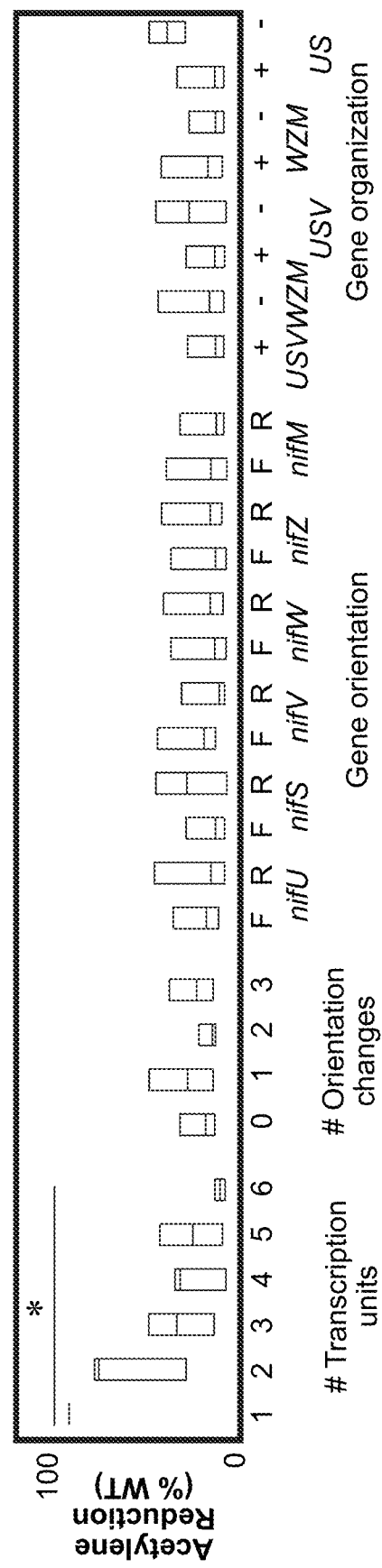
FIG. 2C shows the relationship between several sequence features (x-axis) and acetylene reduction activity. Boxes bound the 25th-75th percentile data points with horizontal line demarking the median value. Asterisk denotes a significant correlation (Spearman coefficient $\rho=0.36$, $p<0.001$).

The library was analyzed to determine if there were correlations between nitrogenase activity and particular genetic features, including gene orientation and order, part combinations, and part activity (FIG. 2B). Gene orientation and order did not correlate with activity and the wild-type order was not enriched amongst the most active constructs. Surprisingly, neither the number of reverse-oriented genes nor the number of orientation changes correlated with activity. There was a significant negative correlation with the number of transcription units (as well as the number of promoters and terminators, which are related); however, there were many outliers.

Mapping the Design Landscape of the nifUSVWZM Operon

Figure 3A:
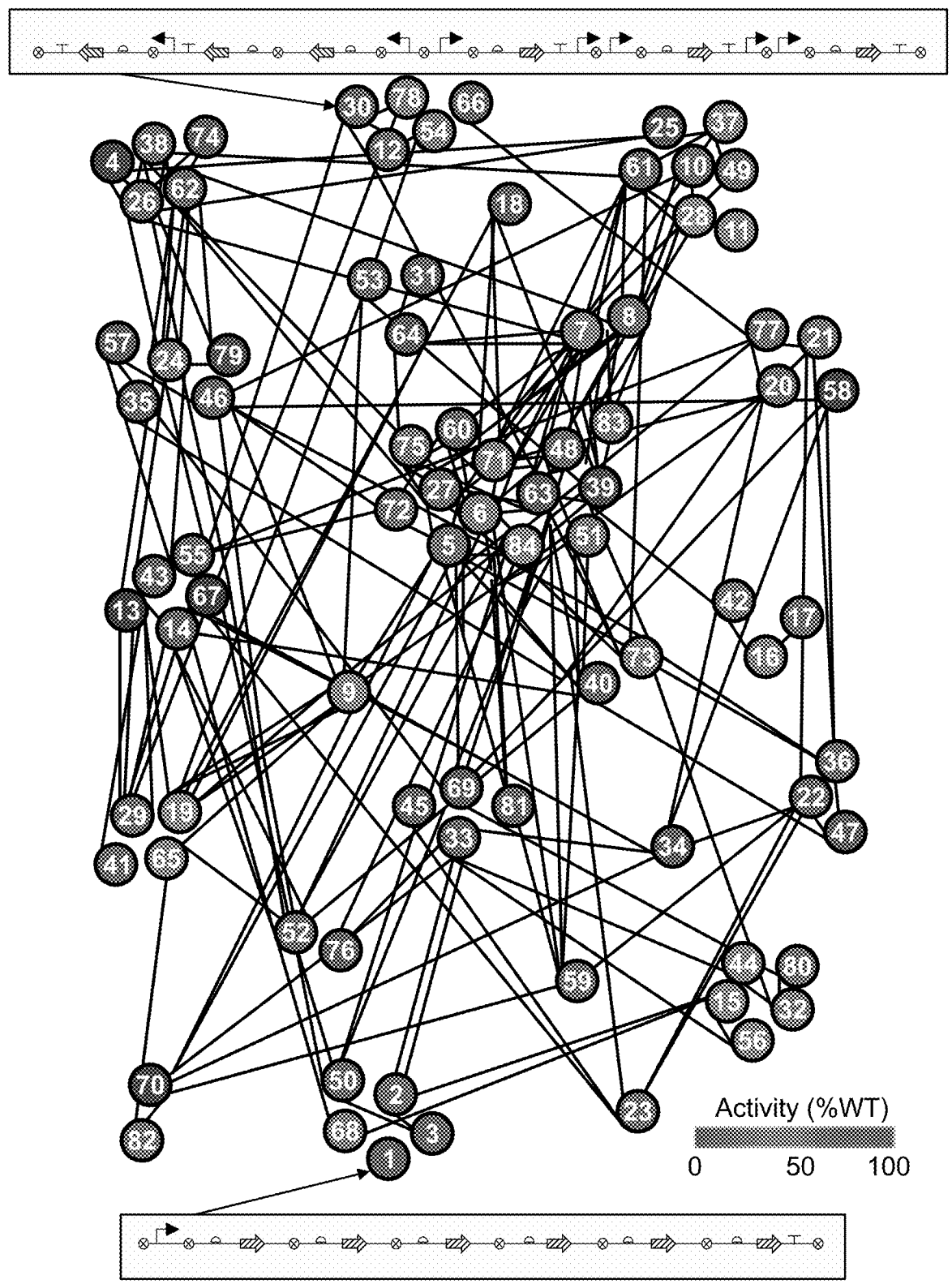
FIG. 3A depicts a ball and edge diagram with gene clusters as nodes grouped by a Markov Clustering Algorithm and shaded according to activity level. Edges connect nodes with genetic distance<0.315. Graphic representation of two most active sequences are shown above (USVWZM #30) and below (USVWZM #1) the diagram.

The plasticity of the refactored nifUSVWZM operon was surprising; variants with different genetic architectures were able to achieve essentially the same function. One can imagine a hyperdimensional "fitness landscape" where genetically similar clusters are close in space and the fitness describes the nitrogenase activity. This is visualized as a map (FIG. 3A), where each node represents a construct and the edges connect similar constructs, which are then clustered (Example 4). While there were some groups of constructs where each member had similar activity, moderate-high activity variants were spread throughout the space. To quantify this, autocorrelation function was calculated as measure of similarity over a genetic distance. This function captures how much the activity changes as one moves further from a starting (wild-type) construct. Then, the distance between two constructs is considered to be the number of cistrons that have to be changed to convert one into the other. The decline in the autocorrelation function was consistent with the NK-model (N=6) when K≈1-240-43. This implied that the landscape had few local minima and could be well approximated by considering pairwise interactions between cistrons (FIGS. 12A and 12B).

The size of the neutral network can also be used to quantify the space. During an evolutionary walk, neutral evolution accelerates adaptation by allowing a population to drift in evolutionary space, thereby increasing the probability that individual mutants will discover improvements (Huynen, M. A., et al. 1996). From the perspective of engineering, this represents the number of alternative genetic architectures that can achieve the same design goal. The size of the neutral networks can be visualized using a spectral graph, where each ring from the center represents sequences further from the distance (Aita, T., et al. 1998). Even at high activities, 11% of the paths are neutral or higher and at moderate activities, this increased to 68%. This implies that during evolution many alternative genetic structures could be explored through neutral drift with little impact on activity.

Additivity and Context Dependence of Genetic Parts and Composites

The ease by which a cluster is optimized is dictated by the structure of the fitness landscape. When parts do not interact, their contribution to the activity is additive and this leads to a smooth landscape (Aita, T., et al. 1998; Wells, J. A., et al. 1990). This is easy to optimize because each part can be tuned individually and then combined. While individual parts may be non-additive (e.g., a promoter because its contribution to activity depends on the gene to which it is fused), larger composite parts (e.g., an operon) may exhibit additivity as a unit. In effect, this is assumed when a sub-portion of a larger construct is optimized and then placed back into the greater context; for example, in the optimization of nifUSVWZM individually and then inserting it back into the context of the full nif cluster. In contrast, when parts or composite parts interact, this can lead to frustration in the landscape because the optimal part in one context may be suboptimal in another. Such interactions could occur due to requirements of one gene product on the levels of another or because of genetic context effects, where the neighboring regions of DNA interfere with the function of a part (Lucks, J. B., et al. 2008; Cardinale, S., et al. 2012).

The nifUSVWZM library was analyzed to determine the extent of non-additivity. The hierarchical assembly structure (FIG. 1B) was used to examine the additivity for parts at different levels. The contribution of each part was calculated by averaging the activity of all constructs bearing that part and the standard deviation was viewed as a measure of how genetic context impacts the contribution of the part to activity (FIG. 11A) (Mutalik, V. K., et al. 2013). As expected, the sum of the calculated part activities correlated poorly with the activity of the complete operon ($R2=0.06$) (FIG. 11C). Weighted averages of the cistrons were correlated with the activities of the full constructs ($R^2=0.37$) and the half-clusters increased further ($R^2=0.54$). Considering pairwise interactions between cistrons increased the correlation significantly, from $R^2=0.37$ to 0.68 (FIGS. 12A and 12B).

Robustness to Changes in RNA Polymerase Concentration

Figure 4A:
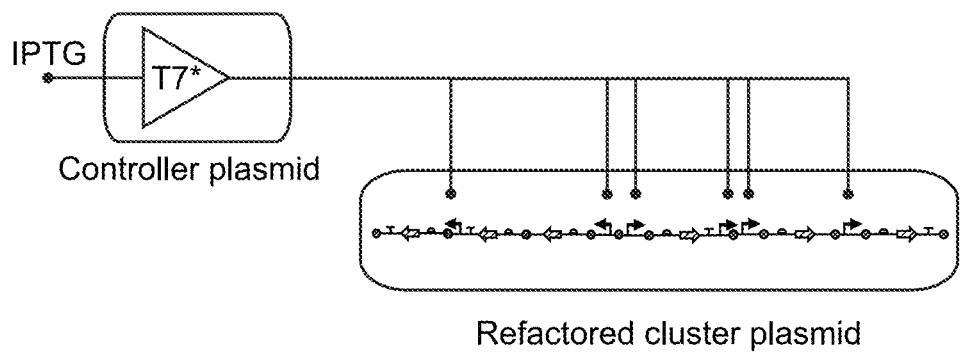
FIG. 4A schematic presents a complete refactored system that allows for IPTG-inducible control of T7* RNA polymerase expression, which in turn determines expression levels from T7 promoters located within each gene cluster.

Operons have been proposed as a mechanism to maintain protein ratios despite changes in the promoter activity (Price, M. N., et al. 2005; Iber, D. A., et al. 2006; Lim, H. N., et al. 2011; Liang, L. W., et al. 2013; Price, M. N., et al. 2006; Dandekar, T., et al. 1998). In comparing the top nifUSVWZM variants that emerged from the screen, it would be possible that a variant with disrupted operons had high activity, but was less robust over a range of RNA polymerase concentrations. The refactored system was induced by a "controller," which simplified testing this by varying the concentration of IPTG to change the concentration of T7 RNA polymerase, which was the sole input to all of the promoters (FIG. 4A).

Figure 4B:
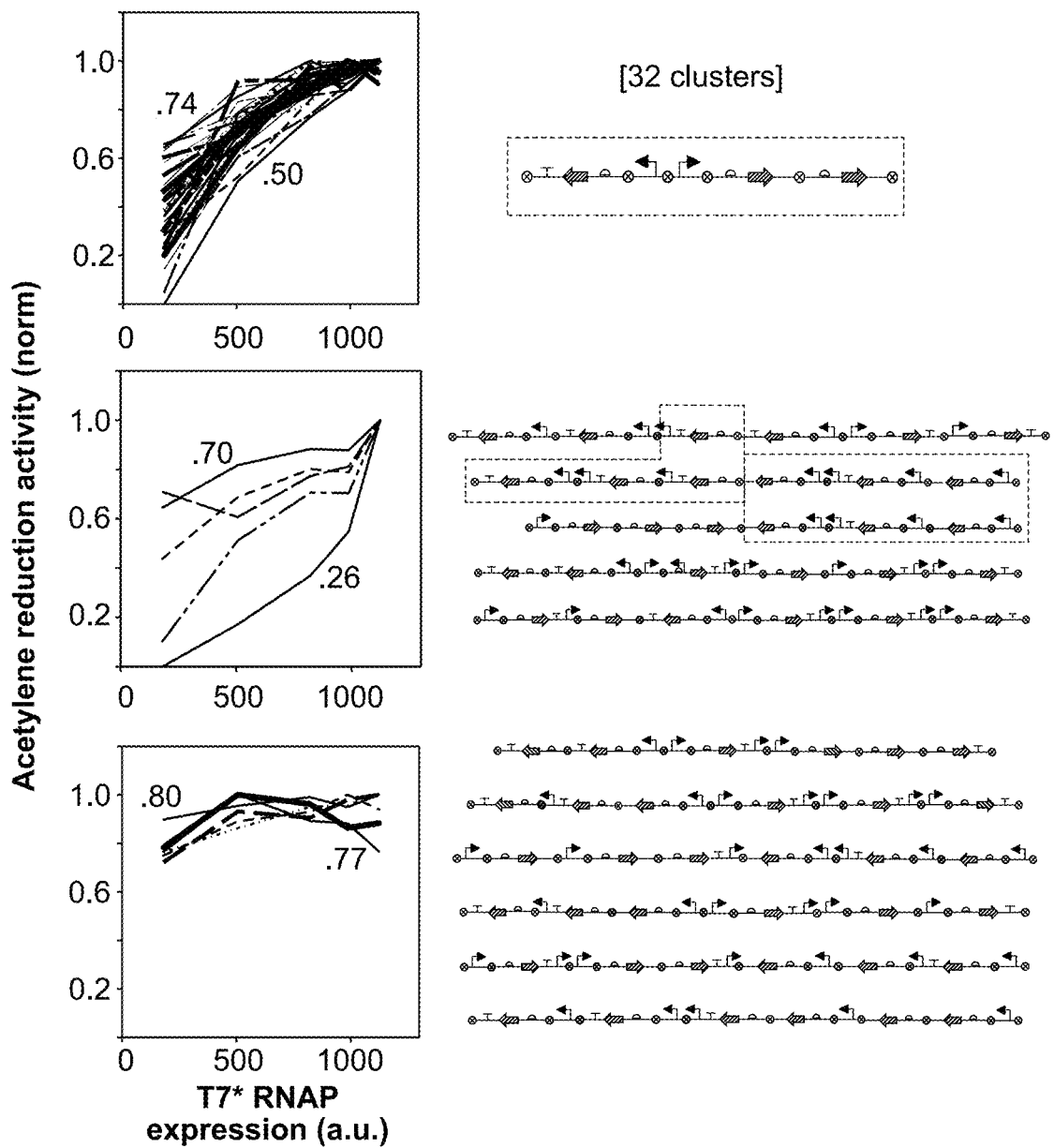
FIG. 4B shows six panels of different response patterns to increasing T7* RNAP expression. Traces highlight the most and least robust examples from each of the response groupings, with the associated robustness values indicated. Genetic sequence motifs that are overrepresented in each response grouping are highlighted in dashed boxes. These enrichments are significant with $p<0.05$ as determined by Pearson's chi-squared test.
Figure 4C:
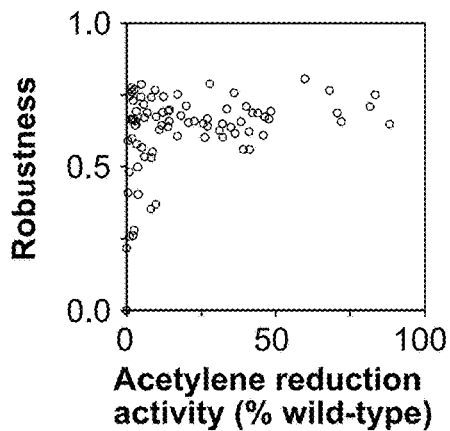
FIG. 4C depicts acetylene reduction activity plotted against gene cluster robustness. Data points do not show a significant correlation (Spearman coefficient $\rho=0.21$, $p>0.05$).
Figure 4D:
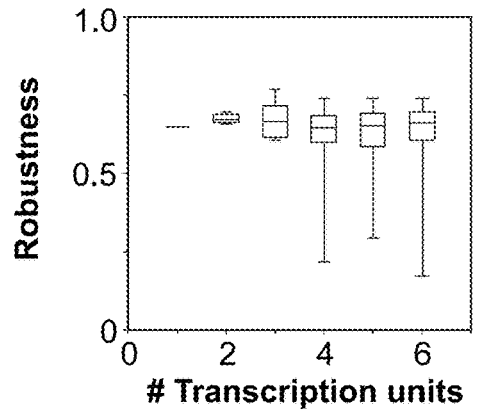
FIG. 4D presents a box-and-whisker plot of number of transcription units versus robustness showing population median (center line), second and third quartile bounds (box), and maximum/minimum data points (whiskers). Data points do not show a significant correlation (Spearman coefficient $\rho=0.07$, $p>0.05$).
Figure 4D:
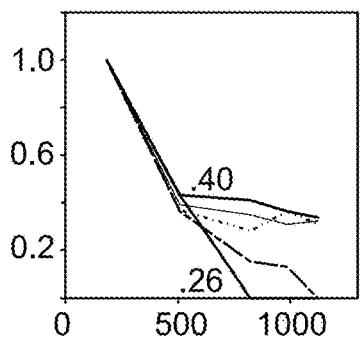
Figure 4D:
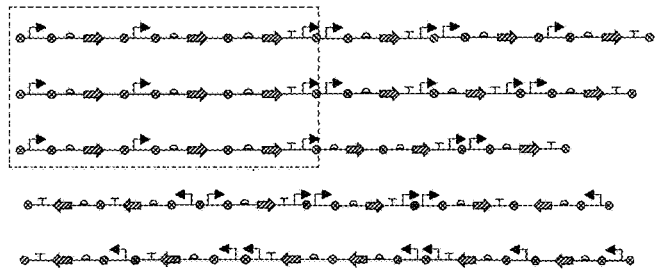
Figure 4D:
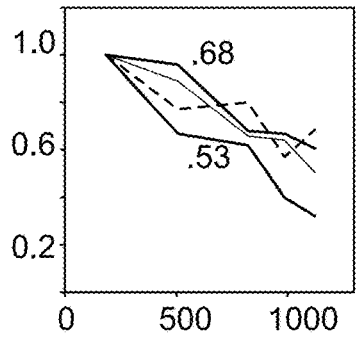
Figure 4D:
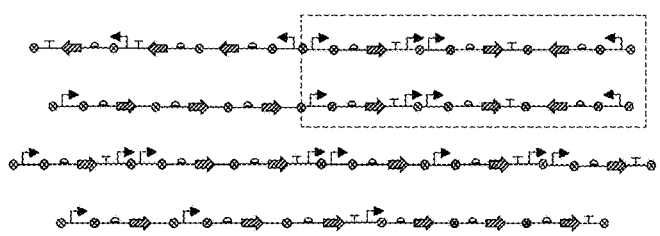
Figure 4D:
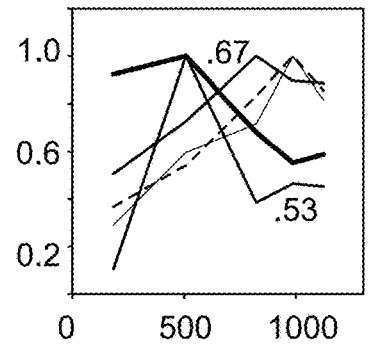
Figure 4D:
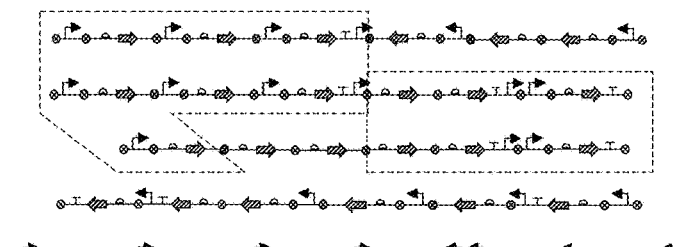

For each of the 57 most active nifUSVWZM variants, the robustness was quantified by measuring the nitrogenase activity at five levels of IPTG induction across two orders of magnitude (FIG. 4C). The majority (32) of the variants monotonically increased in activity as a function of RNA polymerase concentration. However, a variety of other behaviors were also observed. There was a subset of 6 clusters that were very robust over a wide range of RNA polymerase concentrations, showing almost no change in activity. Remarkably, the top cluster identified in the library (USVWZM #30) was in this category, demonstrating that it had both the highest activity as well as highest robustness, despite having broken the operon structure with seven promoters. Other behaviors were also observed, including those that were high at low concentrations and declined monotonically as RNA polymerase was increased. Five showed optimal performance at intermediate concentrations of RNA polymerase. Control experiments were performed to ensure that: 1. negative robustness correlations were not merely the result of increasing toxicity upon greater IPTG induction, and 2. insensitivity was not an artifact of T7 RNAP-independent expression (Example 4). Several cistrons and half-clusters where found to be statistically enriched in one particular robustness category (grey shaded motifs in FIG. 4C). No significant correlation was found between robustness and a number of features, including the orientation of each gene, a requirement for transcriptional read-through, and numbers of predicted transcription units, promoters, and terminators.

Figures 5A, 5B, 5C:
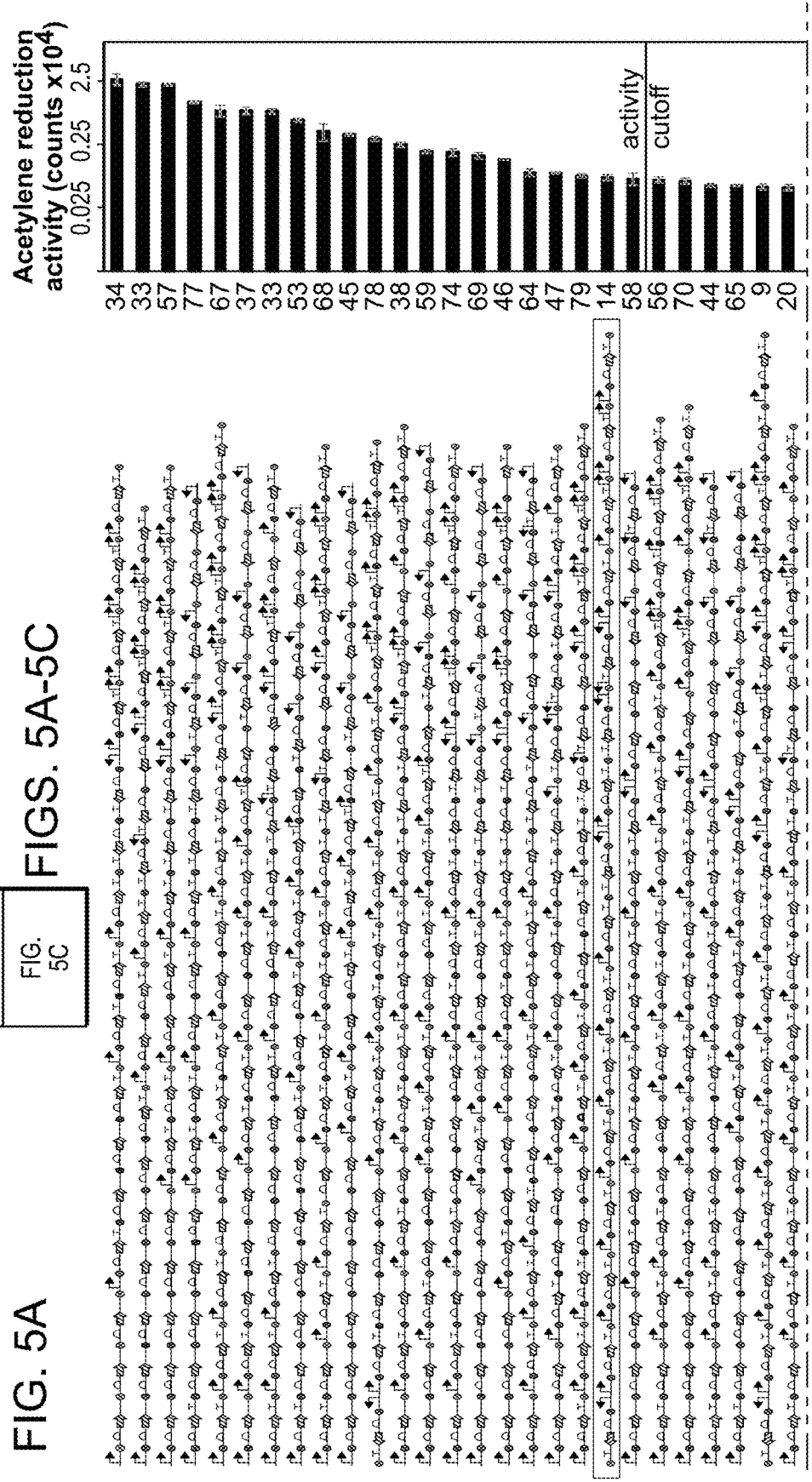
FIGS. 5A-5C show a rank-ordered list of full refactored gene clusters including their composition and log-scale activity. Gene cluster identity is listed left of bar graph, and error bars denote sample standard deviation for two replicates. Characterized genetic parts are identical to FIGS. 2A-2B, with the addition of with the additional promoter P4 ($0.60\pm0.032$ REU; 23 bp), terminators T4 (Ts=5.0; 53 bp), T5 (Ts=3.1; 57 bp), T6 (Ts=4.1; 47 bp), and T7-Ts=2.7; 49 bp), and CDSs nifH (882 bp), nifD (1452 bp), nifK (1563 bp), nifY (663 bp), nifEb (1374 bp), nifN (1386 bp), nifJ (3504 bp), nifB (1407 bp), nifQ (504 bp), and nifF (531 bp).
Figure 5B:
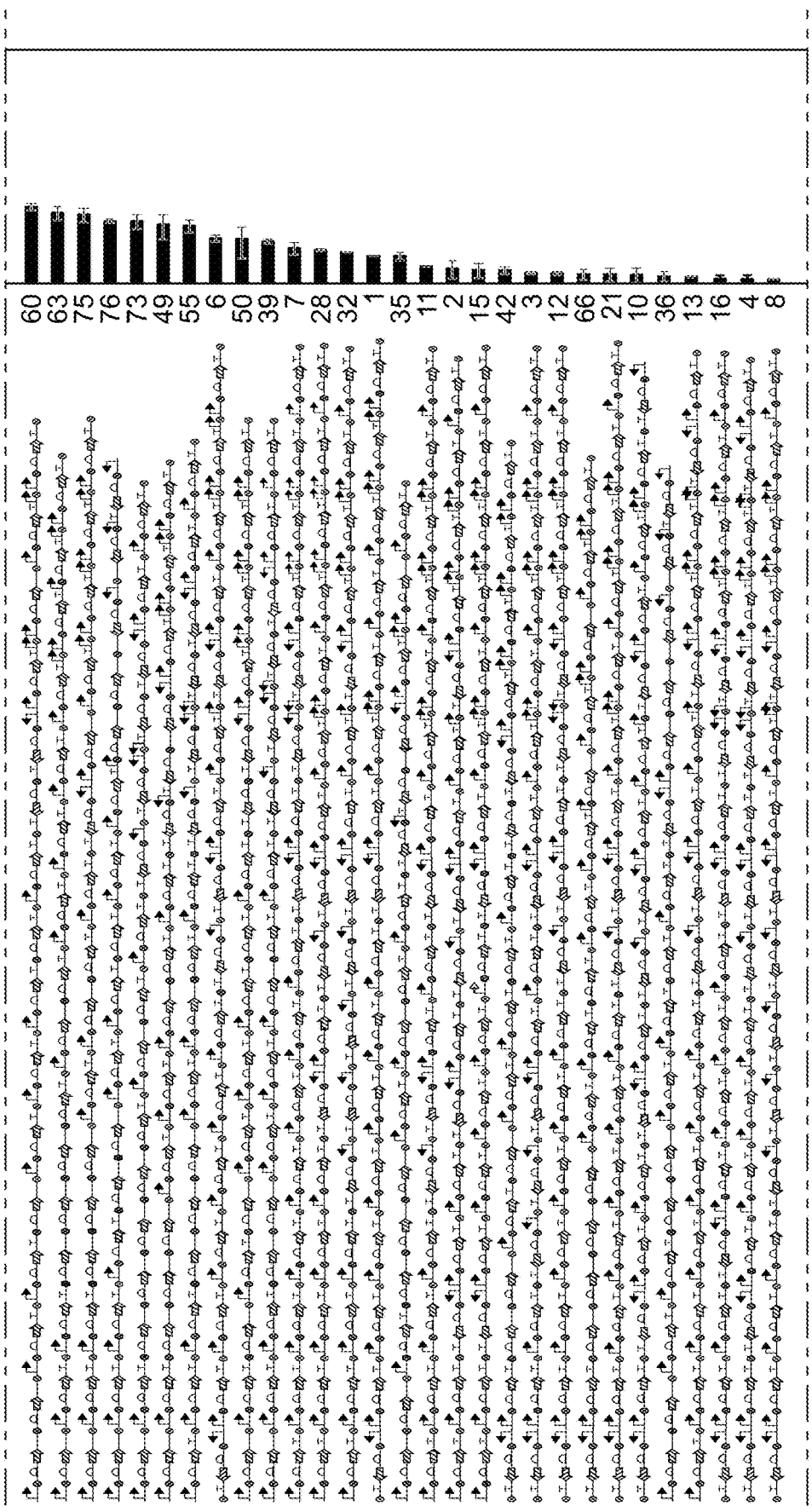
Figure 5C:
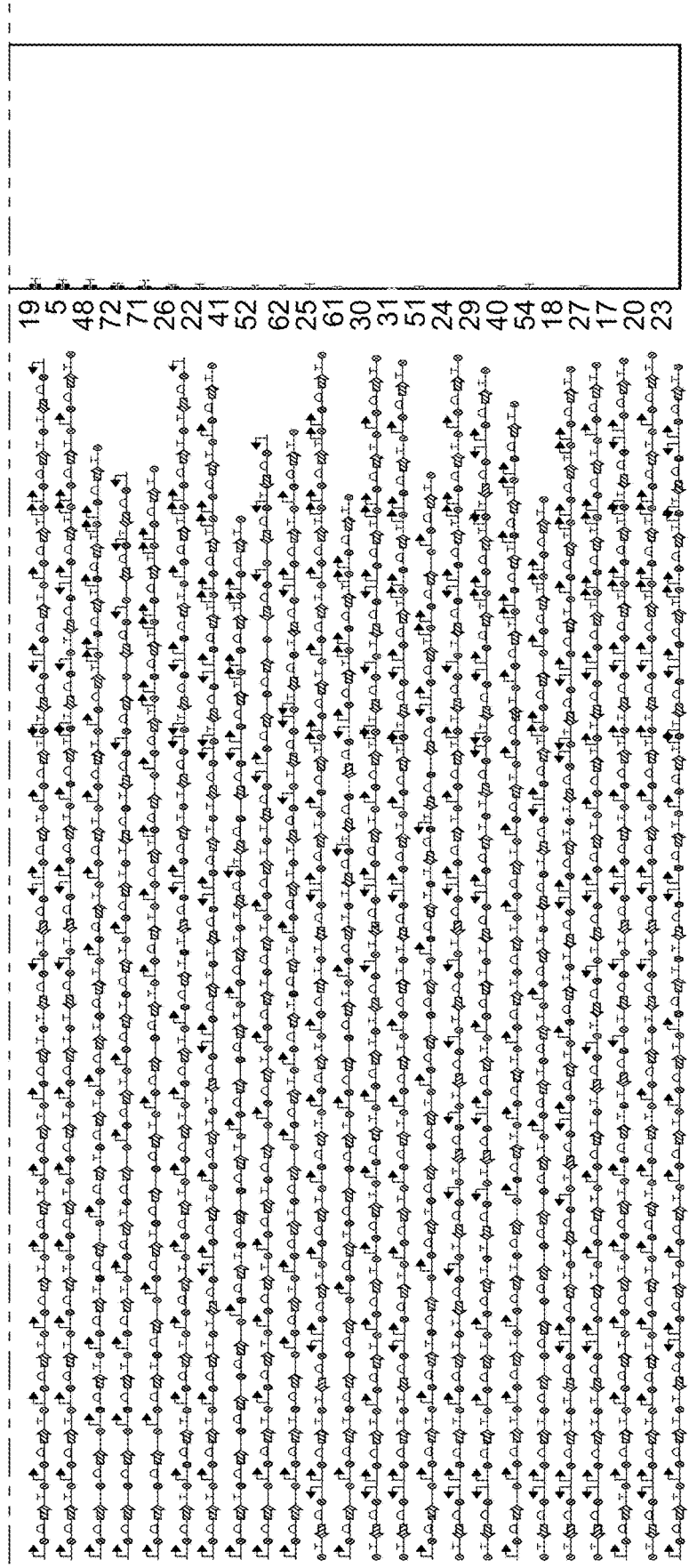
Figure 5D:
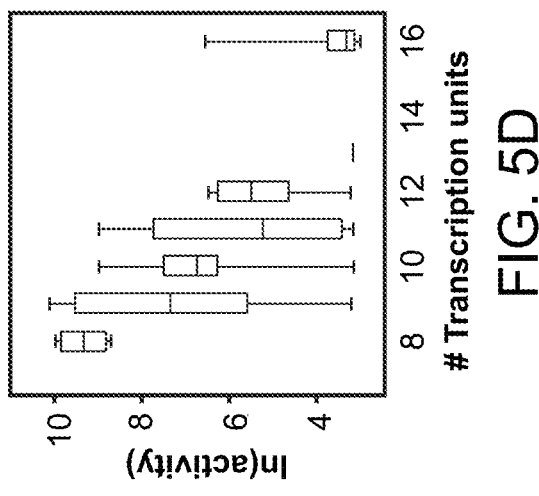
FIG. 5D presents a box-and-whisker plot of number of transcription units versus the natural log of gene cluster activity, showing population median (center line), second and third quartile bounds (box) and maximum/minimum data points (whiskers). There is a strong Spearman correlation of $\rho=-0.64$ ($p<10-9$).
Figure 5E:
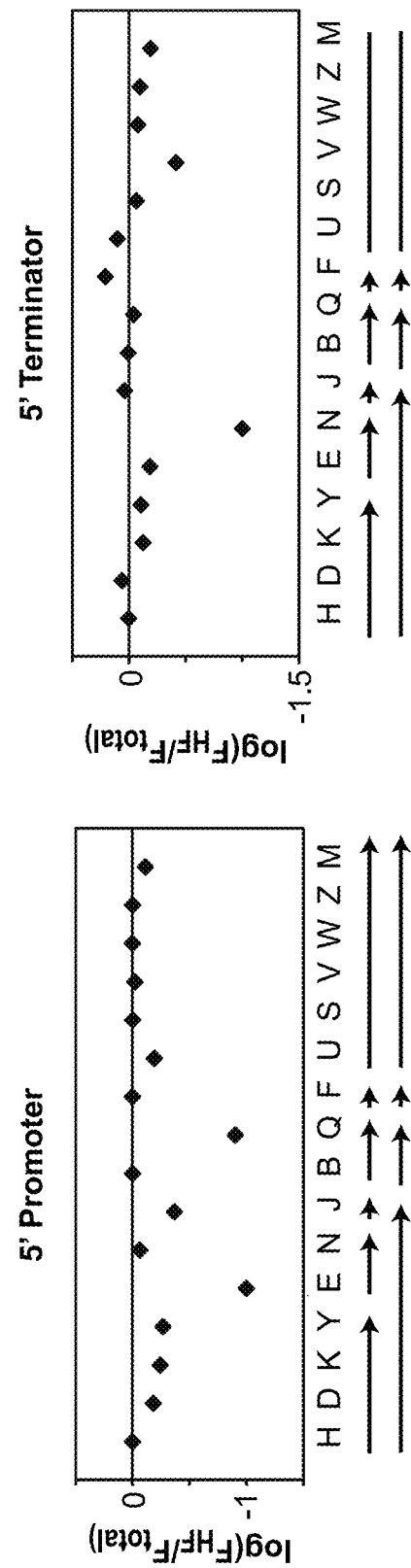

Division of the Complete Nif Gene Cluster into Monocistronic Transcription Units The results from screening the nifUSVWZM library yielded many active variants where the operon structure was disrupted. The degree to which this was possible for the complete nif cluster was determined. The first version of the refactored system maintained similar operon occupancy as the wild-type: the only changes were that the nifHDKY, nifEN, and nifJ were combined into the same operon and the nifF orientation was reversed. A library of permutations of the entire 16-gene 10 refactored nif cluster was designed and assembled in order to identify biases in whether genes need to be neighboring, occur in the same operon, or orientation (FIG. 5A, 5B, 5C).

The full library of 80 constructs was built through two rounds of design and construction (presented in FIG. 15-18). In brief, the approach taken was similar to that used to build the initial nifUSVWZM library except: 1. new strong terminators were used to avoid homologous recombination (Chen, Y. J., et al. 2013), and 2. to ease assembly genes were grouped as nifHKDY/nifENJB/nifQFUS/nifVWZM. A subset of 48 library members was more conservatively designed using constructs from the nifUSVWZM library that had relatively high activities (USVQZM #30, 41, 66, 16, 7, 9, 19, and 23). The DNA assembly was performed following a hierarchal scheme similar to FIG. 1B (FIG. 15)). Nitrogenase activity of the library was measured in E. coli MG1655 (using a controller built for this host) because of increased transformation efficiency for constructs>25 kb (FIG. 5A). In the library, variants with up to 9 transcription units were found that have identical activity with the original refactored system (that has 4 transcription units) (FIG. 5B). After this, the average activity of the clusters declined as the number of transcription units increased. Notably, there were individuals that maintained high activity and even a few fully monocistronic variants (16 transcription units) were active. The highest is highlighted in red in FIG. 5B and has a rearranged gene order: rDHKYJENBrFQrSrUWZMrV, where r indicates reverse orientation. These data indicated that the decrease in activity for more transcription units was because it required more perturbations from a functional variant, but that the particular operon structure of the wild-type or refactored systems were not requirements for activity.

The library was divided at an activity cutoff to compare the features observed in higher-activity clusters with those that had low or no activity. From this, it was observed that several places where the placement of an upstream promoter or terminator, was damaging to the activity, either because it disrupted an operon or was sensitive to perturbed expression levels (FIG. 5C). As compared to the first refactored cluster, it was deleterious to put an upstream promoter in front of nifE or nifQ or a terminator upstream of nifN. It is noteworthy that nifEN was amongst the most conserved operon when compared across species (Suh, M. H., et al. 2002). These proteins form a complex and in some organisms they are fused. Together with nifB and nifQ, these genes form the first commitment step of Fe—Mo—Co biosynthesis and are tightly coregulated (Martinez-Noel, G., et al. 2011; Hernandez, J. A., et al. 2002).

Discussion

In synthetic biology, design is hampered by the genetics of natural systems that have emerged from evolutionary forces. Design choices cannot be cleanly implemented without triggering a web of secondary effects. For example, a desired change in gene order may be tolerable in itself, but if there are promoters internal to the ORFs, then this could create transcriptional interference (Liang, L. W., et al. 2013). Further, it is not possible to make part substitutions; for example, if genes are translationally coupled then it is not possible to swap in an RBS of a different strength or a codon-optimized gene for a new host. These types of changes are required for optimization (Stephanopoulos, G., 2007; Levin-Karp, A., et al. 2013), part conversion for transfer to a new host, or mining genes from databases to create diversity (Bayer, T. S., et al. 2009; Medema, M., et al. 2011). As demonstrated, a refactored gene cluster can be used as a platform to build extremely different architectures and implement design choices that would not be possible with the wild-type system. A surprising result was that many of these highly perturbed systems were functional at all and, in fact, some were able to achieve wild-type levels of activity.

Design rules were difficult to extract from the libraries and it appears that there are very few requirements that features of the wild-type nif cluster be preserved. Of course, this could be an artifact that results from measuring activity only under artificial laboratory conditions. Aspects of regulation or organization may be important for a specific environmental niche. Indeed, it has been observed for other systems that operon structures enable different combinations of genes to be expressed in different environmental conditions (Sorek, R., et al. 2010; Guell, M., et al. 2009). Recent work has shown that while evolutionary pressures may favor operon formation for co-regulated genes, operon architecture is not necessary to coordinate gene expression (Liang, L. W., et al. 2013). This supports previous claims that the formation of operons can be neutral in some cases and adaptive in others (Price, M. N., et al. 2006). Co-translational folding of interacting proteins has been implicated as a driving force behind gene localization (Dandekar, T., et al. 1998) and may be important for the pairing of nifEN, which function together in a protein complex (Temme, K., et al. 2012; Suh, M. H, et al. 2002). Of the many potential features of the native nif operon that could need to be conserved, it is remarkable that this appears to be the only one strongly correlated with activity.

It is intriguing to note that similar diversity is present in natural gene clusters from different species (FIG. 6) (Fischbach, M. A., et al. 2008). Gene order conservation (synteny) is observed for four subsets of genes (nifHDK, nifENX, nifUSV, and nifWZM) that then appear in different arrangements. But even within these subsets, there can be considerable diversity. For example, the core nitrogenase genes nifHDK often occur together, but there are examples where they are divided in different combinations and orientations (Kaneko, T., et al. 2010; Enkh-Amgalan, J., et al. 2006; Thiel, T., et al. 1997). Across genomes, the most conserved pair is nifEN, but even they have an example of being split in S. meliloti (Enkh-Amgalan, J., et al. 2006). The nifUSV and nifWZM operons are often highly disrupted and there are many changes in order, orientation, and location, even within species (Oh, C. J., et al. 2012; Ran, L., et al. 2010; Stucken, K., et al. 2010). This observation was mirrored in our findings, with the nifUSVZM genes being very tolerant to different architectures (FIGS. 2A and 2B). The libraries of refactored clusters are representative of significantly more diversity than what can be obtained in 12 available genomic sequence data. This offers a platform where different genetic architectures can be directly compared side-by-side in a single host organism.

Directed evolution has proven to be a powerful approach to optimize biological systems, including proteins, pathways, and whole genomes (Cobb, R. E., et al. 2012). The approach described herein, based on the multiplexed design and construction of pathways, is essentially a new approach to the directed evolution of large, multi-part systems. The system was able to be constrained according to rules known to be important (for example, creating genetic structures consistent with transcription and translation), while allowing all other aspects of the organization to vary. This forms the basis for the construction of a library that is then screened for activity, and builds on approaches to evolve multi-gene systems that are largely characterized by the introduction of genetic diversity at a single part type (Schmidt-Dannert, C., et al. 2000; Alper, H., et al. 2005; Wu, J., et al. 2005; Du, J., et al. 2012), a single genetic locus (Pfleger, B. F., et al. 2006), or for a single property, such as gene order (Bikard, D., et al. 2010). For small systems, design space has been searched more broadly to explore diversity over multiple part types and loci either rationally or randomly (Ramon, A. and Smith, H. O., 2011; Sleigh, S. C., and Sauer, H. M., 2013; Xu, P., et al. 2012; Crameri, A., et al. 1997; Yokobayashi, et al. 2002). This strategy, which assembles parts in a defined and highly permuted manner, can be applied to gene clusters comprising 100 genetic parts. This is essential in enabling the genetic design to take place at a higher level of abstraction without concern for the sequence-level details of DNA assembly. Even in screening a modest number of variants, one variant was identified that was significantly improved activity and has a radically different genetic architecture.

Materials and Methods

Strains and Media

*Escherichia coli* DH5a (Sambrook, J., et al. 1989) was used for routine cloning and plasmid propagation. *E. coli* MG1655 (Jensen, K. F., et al. 1993) was used as a heterologous host for screening full refactored nitrogen fixation gene clusters, as we observed reduced electroporation efficiencies in *Klebsiella* for plasmids over 20 kilobases. *Klebsiella oxytoca* M5a1 (Stacy, G. S., et al. 1992) was used to determine wild-type nitrogenase activity levels, and knock-out mutant strains *K. oxytoca* NF10 (Temme, K., et al. 2012) was used to screen synthetic nifUSVWZM operons. Luria-Bertani (LB) medium (10 g/L tryptone, 5 g/L yeast extract, 10 g/L NaCl; VWR cat. #90003-350) with appropriate antibiotic supplementation was used for strain maintenance and plasmid construction in *E. coli* strains. LB-Lennox medium (10 g/L tryptone, 5 g/L yeast extract, 5 g/L NaCl; Invitrogen cat. #12780-052) was used for strain maintenance in *K. oxytoca* strains. All nitrogen fixation assays were performed in minimal medium (25 g/L Na2HPO4, 3 g/L KH2PO4, 0.25 g/L MgSO4·7H2O, 1 g/L NaCl, 0.1 g/L CaCl2·2H2O, 2.9 mg/L FeCl3, 0.25 mg/L Na2MoO4·2H2O, and 20 g/L sucrose). Growth medium is defined as minimal medium supplemented with 6 mL/L of 22% ammonium acetate (filter sterilized). De-repression medium is defined as minimal medium supplemented with 1.5 mL/L of 10% serine (filter sterilized). Phosphates were dissolved in distilled water and autoclaved separately from the remaining ingredients to prevent precipitation and sterile medium components were freshly mixed before each use. Antibiotic selection was performed with spectinomycin (100 mg/L; MP Biomedicals cat. #021 5899305), kanamycin (50 mg/L; Gold Bio cat. #K-120-5), ampicillin (100 mg/L; Affymetrix cat. #11259 5), and/or chloramphenicol (33 mg/L; VWR cat. #AAB20841-14). Isopropyl-β-D-1-thiogalactopyranoside (IPTG; Gold Bio cat. #I2481C25 259) was supplemented to medium for induction at various levels. Blue-white screening of colonies resulting from DNA assembly reactions was performed on LB-agar plates (1.5% Bacto agar; VWR cat. #90000-760) supplemented with 0.15 mM IPTG, 60 mg/L 5-bromo-4-chloro-indolyl-β-Dgalactopyranoside (Roche cat. #10 745 740 001), and appropriate antibiotics.

DNA Assembly and Verification

The promoter parts, RBS/CDS parts, and terminator parts that entered into the pipeline at the highest level of the assembly tree were themselves constructed using standard cloning techniques including isothermal assembly (Gibson, D. G., et al. 2009; Gibson, D. G., et al. 2010) and PCR-ligation (Moon, T. S., et al. 2012). All promoter parts are flanked by sequences "GGAG" (upstream) and "TACT"

(downstream), RBS/CDS parts are flanked by sequences "AATG" (upstream) and "AGGT" (downstream), and terminator parts (TPs) are flanked by sequences "TACT" (upstream) and "AATG" (downstream). These four-bp sequences correspond to 5'-overhanging single-stranded cohesive ends when digested with restriction enzymes BbsI (promoter and RBS/CDS parts) or BsaI (terminator parts). Application of the Scarless Stitching method (FIG. 6. and FIGS. 7A and 7B.) to create a seamless junction between any combination of promoter part and RBS/CDS part proceeds as follows: 20 fmol each of promoter part plasmid, RBS/CDS part plasmid, pMJS20BC, and pMJS23AD are mixed with 5 U BbsI (New England Biolabs, Ipswich, Mass., cat. #R0539S) and 5 U T4 DNA Ligase (Promega, Madison, Wis., cat. #M1794) in a total of 10 µl 1× Promega T4 DNA Ligase Buffer and incubated at 37° C. for 4.5 hours. Next, a 10 µl solution containing 5 U MlyI (New England Biolabs, cat. #R0610S) and 5 U T4 DNA Ligase in 1× Promega T4 DNA Ligase Buffer is added to each reaction and incubated an additional 30 min at 37° C. Reactions are terminated by incubating at 50° C. for 5 min and 80° C. for 10 min. Constructed plasmids are transformed into E. coli and prepared for sequence confirmation by Sanger sequencing using standard techniques. The efficiency of this method was established by reconstructing a GFP coding sequence from two halves (Supplementary Information). Scarless stitching of a promoter-RBS/CDS construct to a terminator part follows a similar protocol to that described above, with pMJS25DB and pMJS24AC replacing pMJS20BC and pMJS23AD, and BsaI (New England Biolabs cat. #R0535S) replacing BbsI. For unknown reasons, the efficiency of this second round was significantly worse than the first, with single base pair deletions present in at the part junction in over 70% of the sequenced constructs. Constructs containing a promoter part, RBS/CDS part, and terminator part are considered 'cistron parts'.

Sequence-verified cistron parts are PCR amplified to give each construct specific cohesive ends upon BbsI digestion that dictate the orientation and relative position in the overall assembly. PCR products are cloned into Level 1 plasmids (pCV27069) with the appropriate flanking cohesive ends using a Golden Gate assembly reaction (Engler, C., et al, 2008; Weber, E., et al. 2011; Werner, S., et al. 2012). At this stage each part is sequence verified. Fourteen of the 48 cistron parts contained a 1-2 bp deletion in the beginning of the terminator part (see Example 4), but as the first 6 bp of the terminator parts are not part of the hairpin structure and are not expected to affect termination efficiency (Chen, Y. J., et al. 2013), these were still carried further in the library assembly. Three (nifUSVWZM library) or four (monocistron library) Level 1 plasmids are combined by BsaI digestion/ligation into Level 2 plasmids (pCV27070) using a Golden Gate assembly reaction to intermediate assembly plasmids dubbed half-clusters or quarter-clusters for the nifUSVWZM or monocistron libraries, respectively. Finally, Level 2 plasmids are combined by BbsI digestion/ligation into the expression vector pMJS2001AC to form Level 3 plasmids containing 6 or 16 genes of the nifUSVWZM operon or complete refactored nif gene cluster.

Level 2 and Level 3 plasmids are verified by colony-multiplex PCR using primers that anneal to the CDS sequences of each gene. Colonies are picked into 10 µl of sterile H2O and boiled at 100° C. for 10 min. Boil preps are centrifuged to pellet cell debris, and 0.5 µl supernatant is used as template in 5 µl PCR reactions using Phusion High-Fidelity DNA Polymerase (New England Biolab, cat. #M0530L) with standard reaction conditions and the following heat cycle in a Bio-Rad C1000 Touch Thermal Cycler (Hercules, Calif.): 98° C. for 30 s, 35 cycles of 98° C. for 10 s, 60° C. for 30 s, and 72° C. for 15 s, followed by 72° C. for 10 min. PCR reactions are analyzed by agarose gel electrophoresis or on a Qiaxcel (Qiagen, Germantown, Md.) with a DNA Screening cartridge and 320 s separation time. The Golden-Gate assembly of cistron-parts into larger constructs proceeds through a cut-and-paste type mechanism and is likely less error prone than polymerase-dependent cloning techniques. Multiplexed PCR verification tests whether product constructs contain each of the desired parts. Performing a multiplex PCR reaction produced a characteristic pattern of products that could be analyzed by agarose gel electrophoresis or capillary electrophoresis. Test assemblies of complete refactored nitrogenase gene clusters with the gene order and orientation unchanged revealed an efficiency of the four-piece Golden-Gate reactions to be >80%. Because expected PCR product profiles for gene clusters with permuted gene order and orientation are unique and complex we screened for correct constructs by checking at least three colonies from each reaction by multiplex PCR. Correct constructs were selected as those producing identical product profiles in 3/3 or 2/3 replicates.

Nitrogenase Activity Assay

Nitrogenase activity is determined in vivo via the previously described acetylene reduction assay (Temme, K., et al. 2012; Stewart, W. D., et al. 1967). Each strain is grown in 2 ml growth medium (supplemented with required antibiotics) in 15 mL culture tubes for 14 hours in an incubated shaker (30° C., 250 rpm). Cultures are diluted in 2 ml derepression medium (supplemented with required antibiotics and inducers) to a final OD600 of 0.5 in 10 ml glass vials with PTFE/silicone septa screw caps (Supelco Analytical, Bellefonte, Pa. cat. #SU860103). Headspace in the bottles was repeatedly evacuated and flushed with N2 gas using a vacuum manifold equipped with a copper catalyst O2 trap. After 5 hour incubation at 30° C. and 250 rpm in an incubated shaker, headspace was replaced with 1 atm argon. Acetylene was freshly generated from $CaC_2$ in a Burris bottle, and 1 ml was injected into each bottle to start the reaction. Cultures were incubated at 30° C., 250 rpm for 15 hr before the assay was quenched by the addition of 500 µl of 4 M NaOH to each vial. Ethylene production was analyzed by gas chromatography on an Agilent 7890A GC system (Agilent Technologies, Inc. Santa Clara, Calif. USA) equipped with a PAL headspace autosampler and flame ionization detector as follows. 250 µL headspace preincubated to 35° C. was sampled and separated on a GS-CarbonPLOT column (0.32 mm×30 m, 3 micron; Agilent) at 60° C. and a He flow rate of 1.8 ml/min. Detection occurred in a FID heated to 300° C. with a gas flow of 35 mL/min H2 and 400 mL/min air. Under these conditions, acetylene eluted at 3.0 min post injection and ethylene at 3.7 min. Ethylene production was quantified by integrating the 3.7 min peak using Agilent GC/MSD ChemStation Software.

Computational Autocorrelation Analysis

Hamming distances between gene clusters in the nifUSVWZM library were generated between six digit strings of cistron parts. Only two pairs of gene clusters were separated by a distance of 1, and these were excluded from the analysis to avoid large errors arising from the small sample set. The maximum distance using this metric is 6. An autocorrelation function: (Fontana, W., et al. 1993)

$$p(d) = \frac{<f(x)f(y)>_{d(x,y)=d} - <f>^2}{\sigma^2}$$

where σ2=<f²>−<f>², and f(x) and f(y) are all pairwise combinations of gene clusters separated by a cistron-level hamming distance, was evaluated for distances 2-6 and results plotted in (FIG. 4B). There were not sufficient pairs with d=1 to include this in the analysis. Autocorrelation functions for theoretical landscapes based on the NK-model were generated with the following equation: (Fontana, W., et al. 1993)

$$p(d) = \left(1 - \frac{d}{N}\right)\left(1 - \frac{K}{N-1}\right)^d$$

where d is the cistron-level Hamming distance, N is the total number of parts, in this case six, and K is the order of interaction, ranging from 0 to 5.

Computation Neutral Path Spectral Charts

For each of the 84 nifUSVWZM gene clusters, the nitrogenase activity of the other 83 library members were plotted as a function of their cistron-level hamming distance from the original gene cluster. From these graphs, upper and lower boundaries denoting +/−5% wild-type nitrogenase activity were used to determine the fraction of neighboring gene clusters at each distance, d, that represent fitness improvements, fitness decreases, or neutral fitness evolution. These are plotted in spectral graphs (Aita, T., et al. 1998) with the innermost circle representing d=2 and the outermost circle representing d=6. At each circle, the fraction of gene clusters at that distance with lower fitness are measured clockwise from the vertical axis, the fraction of gene clusters with neutral fitness are measured counterclockwise from the vertical axis, and the remaining area represents the fraction of gene clusters with improved fitness. Plots in FIG. 3C represent averages for clusters with rank order 1-10 (top ten), 25-54 (middle thirty) and 55-84 (bottom thirty).

Example 2

Design and Characterization of Synthetic Genetic Parts

The relative expression units (REUs) were determined as a measure of promoter strength for each of T7 promoters used in library design and construction. Promoter strength was calculated using a slightly different method than previously reported (Temme, K., et al. 2012). T7 promoters used in this study were measured by cloning them into the P23100 locus of the internal standard plasmid N110. By maintaining the same RBS in the measurement plasmid and the internal standard, we can bypass the RBS Adjustment step when calculating REUs (Temme, K., et al. 2012). The adjusted protocol is outlined in FIG. 7A, along with the experimentally determined promoter strengths (FIGS. 7A and 7B).

Two ribosome binding sites for each CDS in the nif gene cluster were implemented in the library design and construction. The RBS from the original refactored gene cluster2 was reused and is given the label R[x]1, where [x] is a lowercase letter corresponding to the CDS name. R[x]2 corresponds to a second RBS designed with a five-fold difference in strength as predicted by the RBS calculator (Salis, H. M., et al. 2009). For nifDNJBQUVWZ, the second RBS is 5× stronger that the original. For nifHKYEFSM, 5× stronger designs could not be predicted with the RBS calculator, as the required strength fell outside of the limits for this tool. In these cases, the second RBS was designed to be 5× weaker than the original RBS. In two instances, designed RBSs had to be modified to remove MlyI restriction sites prior to their incorporation in the assembly pipeline. These parts, Ry3 and Rf3, were re-screened by the RBS calculator to ensure their predicted strength was not significantly affected by the substitution.

Terminators sequences were taken from previous studies (Temme, K., et al. 2012; Chen, Y. J., et al 2013), but were re-characterized to determine their strength against the T7* RNAP used here. Terminators were cloned into the T7 terminator characterization plasmid, N292 (SBa_000566) and introduced to the K. oxytoca expression host containing controller plasmid N249 (SBa_000560). GFP and RFP expression was measured under the same assay conditions as described above for promoter characterization. Terminator strengths, reported as the fold reduction in RFP expression compared to a control plasmid lacking a terminator, are as follows: T1, 2.61±0.58; T4, 5.56±1.27; T5, 2.82±0.51; T6, 3.60±0.72; T7, 3.03±0.95.

New spacer sequences were designed using the Random DNA Generator (www.faculty.ucr.edu/~mmaduro/random.htm) with a size of 50 bp (S0-S17) and a GC content of 50%. Initially, spacers S0-S3, which always precede an RBS in the designed libraries, were screened to ensure they do not encode RBS sites. Spacers S10-S17, present in terminator parts, were screened to ensure they do not interrupt the terminator hairpin structure. Spacers S101-S113 arose upon insertion of a 4 base pair MoClo scar into the cistron-separating spacers from the original refactored gene cluster. Scars were preferentially inserted into the 5' section of spacers to minimize polar effects on downstream RBS sites. For example, the 50 bp spacer, SBa_000453, from the original refactored gene cluster was divided by a 4 base pair scar into spacers S101 (5 bp) and S102 (45 bp).

All genetic parts present in the nifUSVWZM and full 16-gene libraries are reported in the attached Excel supplementary files with their computationally predicted terminator, RBS, and sigma-70 promoter strengths. Terminator strength was computed with the terminator calculator (Chen, Y. J., et al. 2013), using a window length of 30 bases or 40 bases depending on part size. RBS strength was determined via the RBS calculator v1.1 (salis.psu.edu/software) (Salis, H. M., et al. 2009) using Klebsiella as the host organism, although the relavent 16s rRNA sequence is completely conserved between this and E. coli, so the predicted values can be applied to both screening strains. Calculation of a RBS strength is dependent on the presence of a start codon in the sequence to be screened, so to ensure that a value was returned for each genetic part, an 'ATG' start codon was appended to the 3' end of each sequence. While the upstream and downstream genetic context is known to effect RBS strength, we did not screen part sequences in each possible combination. Thus, the reported RBS strength represents the maximum, context independent value for each genetic part. Large genetic parts (>85 bases) were screened for sigma-70 dependent promoters using an algorithm that includes a score for UP elements 6. Other parts were screened with the BPROM online tool that scores −35 and −10 regions and the spacing between them (linux1.softberry.com).

The hierarchical DNA assembly pipeline produces intermediate assembly products that can be reused in multiple designs. Icon depictions of the intermediate constructs described FIR 1 B are shown in FIGS. 8A, 8B, and 8C.

Example 3

Library Description Using EUGENE

The nifUSVWZM library samples a small set of possible designs from a large design space. Eugene is a specification language (Bilitchenko, L., et al. 2011) for describing design sets combinatorially. In a Eugene specification, a designer defines a library of genetic parts mapped to their part types, and using these part types, defines the abstract structure for a library of genetic designs. Eugene takes as input the parts library and rules that constrain how parts are allowed to be combined and produces an exhaustive list of designs that fit the abstract design defined in the specification. This design space is defined by the parts library and the abstract design.

The parts of the nifUSVWZM library are described by defining promoter, spacer, RBS-gene, and terminator parts. The design space is constrained with the following rules: (i) a gene cluster is composed of between one and six operons, (ii) each cluster contains exactly one copy of each of the six genes, and (iii) the U, S, V, genes are positioned before the W, Z, and M genes.

Each gene is packaged as a cistron and is preceded by a promoter or a spacer and followed by a terminator or a spacer. This is specified in Eugene as follows. There are six defined abstract designs, with the i-th abstract design describing an operon that contains i cistrons. Another set of six abstract designs are defined with the same sequential structure as before, but oriented in the opposite direction. Any design from the nifUSVWZM library design space can be composed from the concatenation of some subset of these 12 abstract designs, or equivalently, the Cartesian product of some subset of these 12 design spaces. A procedure in Eugene computes each possible cluster in this abstract design space. This space, however, also contains invalid designs such as, for example, one that contains multiple copies of each gene. This product design space is sieved using Eugene rules. Three sets of rules are defined: rules requiring all six genes to be present; rules requiring U, S, and V genes to be positioned before W, Z, and M genes; and rules requiring there to be exactly one copy of each of the six genes. Finally, we use built-in Eugene functions to reify the abstract design space to obtain designs with specific parts from the parts library.

Example 4

Correlation Between Sequence Features and Activity of the nifUSVWZM Library

Sequence features including gene orientation, order, and numbers of promoters, terminators, transcription units and more were tabulated for each member of the nifUSVWZM library. To search for correlation between sequence features described by discrete variables (i.e. number of transcription units, number of tandem promoters, number of reverse-oriented genes, etc.), the acetylene reduction activity of each gene cluster was plotted as a function of number of sequence features present in that construct. Spearman correlation coefficients and probability scores were calculated for each relationship using the Statistics Toolbox 'con' function in Matlab (Mathworks, Inc., Natick, Mass.). For sequence features that could not be described by discrete variables, for instance 'orientation of nifS', Pearson's chi-squared test was applied to see if either state was statistically enriched or de-enriched in the top 25% of the gene clusters. Regardless of statistical method used, a probability score of $p<0.05$ was used to infer significance. Several sequence features were anti-correlated with acetylene reduction activity, including number of transcription units, promoters, terminators, and tandem promoters (FIG. 9). No significant (de-)enrichment was found for gene orientation.

Toxicity Measurements of the nifUSVWZM Library

As the strict requirement for anaerobic conditions prevented facile measurement of culture optical density during activity screens, a separate experiment was performed to look for toxicity across the range of induction concentrations tested. Screening strains containing the nifUSVWZM library were grown in 0.5 mL cultures in 96-well deepwell plates. As with activity screening, cells were grown in LB-Lennox and Minimal Growth medium prior to inoculation of Derepression Medium. Prior to inoculation, OD600 measurements were made in a plate-reader by diluting seed cultures 1:10 in clear-bottom 96-well plates. Wells were individually diluted to equivalent OD's, and were inoculated into the Derepression Medium at $OD_{600}$=0.5. Medium containing 0.0316 mM, 0.1 mM, 0.316 mM, 1 mM, and 3.16 mM IPTG was inoculated in separate deep-well plates, and plates were allowed to equilibrate in an anaerobic chamber for 15 minutes with no lids. Plates were then sealed with aluminum sealers and incubated at 30° C. with agitation for 22 hrs. Final OD measurements were made in a plate reader after once again diluting cultures 1:10 in minimal media. Results indicate a general toxicity from strains expressing the refactored system, however the observed optical density measurements do not correlate with robustness pattern groupings.

Controllerless Activity of the nifUSVWZM Library

Combining characterized genetic parts into different local contexts can lead to the unintended formation of functional DNA sequences are part junctions (Yao, A. I., et al. 2013). To ensure that the gene clusters that are seemingly insensitive to changing IPTG concentrations do not owe their activity solely to T7* RNAP-independent transcription, the controllerless activity was measured for each strain in the nifUSVWZM library.

The entire nifUSVWZM library was introduced to the screening strain K. oxytoca NF10 lacking the T7 controller plasmid N249. Each of the resulting strains was assayed using the standard conditions, except no IPTG was added for induction. In general, the T7* RNAP-independent activity corresponds to less than 11% of total activity in the majority of cases. When analyzing gene cluster robustness to induction levels, these T7* RNAP-independent activity levels were subtracted from total activity measurements across all IPTG concentrations. Corrected activity measurements were not allowed to drop below 0 (no activity). The gene clusters that do not respond strongly to changing induction levels (FIG. 4B) do not contain high T7* RNAP-independent activities (15% of total activity), however the gene clusters with steep negative responses to increasing induction (FIG. 4B) do have significant T7* RNAP-independent activities (85% of total activity).

Additivity of Parts of the nifUSVWZM Library

The fitness of a genetic part, whether for a base-part or an intermediate construct in the assembly, is defined as the arithmetic mean of the measured nitrogenase activities of full gene clusters containing that part. For instances when a part is repeated several times in the same gene cluster (especially common for the promoter parts and terminator parts), that cluster's activity is factored into the mean an equivilant number of times. The fitness of a part is formally captured with the following notation:

$$f(x) = \frac{1}{m_{total}} \sum_{i=1}^{n} m_i * \text{activity}(C_i)$$

in which is the number of occurrences of part x in gene cluster C, for a library with a total of n gene clusters. Part fitness is shown for initial and intermediate parts in the assembly hierarchy in FIG. 11A as the logarithm of the ratio of individual part fitness to average part fitness. Better than average parts fall above the x-axis and worse than average parts fall below the x-axis.

A part's standard deviation is the sample standard deviation of the fitness calculation. If a part has a low standard deviation, the clusters in which it appears all have very similar nitrogen fixation activities. Conversely if a part has a high standard deviation, it means the clusters in which it appears have a wide range of nitrogen fixation activities. Part standard deviation was found to correlate with part fitness at each level of the assembly hierarchy (FIG. 11B). This correlation explains the intuitive but important observation that containing a low-fitness part can guarantee that a gene cluster will have low activity, but that containing a high fitness part cannot guarantee that a gene cluster will have high activity. In other words, low-fitness parts tend to be dominant over high-fitness parts.

Part fitness and part standard deviation are both used to predict the total activity of a gene cluster from its component parts. We used a weighted average of part fitnesses (f), with the weights determined by the reciprocal of the part standard deviation ($\sigma$):

$$\text{Predicted Activity} = \sum_{i=1}^{n} f_i \frac{\left(\frac{2}{\sigma_i}\right)}{\sum_{j=1}^{n} \frac{2}{\sigma_j}}$$

With this equation, parts that have low standard deviations factor more heavily into the final prediction. The quality of this prediction is given by calculated R-squared value to the y=x line (FIG. 11C). Half-cluster parts yield the best predictions, explaining over 50% of the variance in the experimental data. The quality of predictions quickly falls off as earlier parts in the assembly hierarchy are used.

Pairwise Cistron Part Fitness and Predictions of the nifUSVWZM Library.

A major drawback to the fitness calculations and predictions generated above is that they naively assume that genetic parts are independent (i.e. non-interacting) and additive. Based on the analysis of the fitness landscape, this is not accurate for the refactored nifUSVWZM subcluster. An alternative approach requires determining the fitness for unique combinations of genetic parts (equivalent to the interacting terms in multivariate analysis) and predicting cluster activities using these values. As before, the pairwise part fitness for two cistron parts is the mean cluster activity for gene clusters containing both parts. FIGS. 12A and 12B depict the results of calculating fitness values for pairwise combinations of cistron-level parts and their ensuing predictions of gene cluster activity. The prediction in this case is a non-weighted average, as there are not enough measurements for each pairwise combination to determine a standard deviation for the weighting function. It is important to note that the predictions more closely match actual activity compared to the half-cluster predictions from FIG. 11C, even though the cistron-level parts used come from earlier in the assembly hierarchy. The utility of this approach for predicting the activity of novel combinations is limited. We could not predict the activity of the 21 new clusters because they are composed of some pairwise combinations that were not present in the original data set.

Metric for Genetic Distance and the Clustering Algorithm of the nifUSVWZM Library Existing distance metrics for determining gene cluster similarity 1 do not capture changes in the 5'-UTR or promoter regions that are prevalent in the refactored gene cluster libraries produced here, so a new distance metric was created to place library members in sequence space. This distance metric was used in generating the ball-and-edge graph in FIG. 3A. The final distance metric is the sum of four functions, GRD, RBS, PTV, and LEV, explained in more detail below. The distance metric, d, is defined as:

$$d(x, y) = \frac{GRD(x, y) + RBS(x, y) + PTV(x, y) + LEV(x, y)}{4}$$

For any pair of designs x and y, the function GRD (gene reversal distance) measures gene synteny (order and orientation) using the metric of minimum reversal distance, which has shown to be a good estimate of evolutionary distance between organisms (Kececiglu, J., et al. 1995). A reversal is equivalent to an inversion event in the lexicon of genetics. For CDS part sequences cds_x and cds_y, the minimum gene reversal distance GRD is the minimum number of reversals needed to permute the sequence of CDS parts cds_x to cds_y. GRIMM10 was used with the command parameter options "grimm-L-d-s" to compute GRD. The GRD values range between 0 and 6 for the nifUSVWZM library. Formally, the GRD function is defined as follows:

$$raw(GRD)x, y) = \text{minimum number of reversals to permute } cds_x \text{ to } cds_y$$

$$GRD(x, y) = \frac{rawGRD(x, y)}{\max_{\text{over all } u,v \text{ in } nifUSVW2M \text{ library}} rawGRD(u \cdot v)}$$

The function RBS maps the set of pairs of RBS-CDS parts, r_x and r_y, from a pair of designs x and y to their Hamming distance. In the nifUSVWZM library, each gene in x and y has one of two different RBSs preceding it. The function RBS computes the bitwise Hamming distance between r_x and r_y: if the RBSs preceding two otherwise identical genes in x and y are identical, then the Hamming distance between those RBS-gene part pairs is defined to be 0, else it is defined to be 1. The value of the RBS function on designs x and y is the sum of the Hamming distances for each RBS-gene part in x and y. The RBS values range from 0 to 6 for the nifUSVWZM library. Formally, the RBS function is defined as follows:

$$PerGeneRBS(x, y, g) =$$
$$\begin{cases} 0, & \text{rbs-gene part for CDS } g \text{ in } x \text{ is identical to that in } y \\ 1, & \text{otherwise} \end{cases}$$

$$rawRBS(x, y) = \sum_{g \in (U,S,V,W,Z,M)} PerGeneRBS(x, y, g)$$

$$RBS(x, y) = \frac{rawRBS(x, y)}{\max_{\text{over all } u,v \text{ in } nifUSVWWZM \text{ library}} rawRBS(u, v)}$$

The PTL (promoter-terminator locations) function provides additional weight for gene clusters with similar transcription unit architectures. For each CDS g, its PTL is defined as a two-bit vector with the first bit being one if and only if g has a co-oriented promoter preceding it without any intervening terminator or gene, and the second bit being one if and only if g has a co-oriented terminator succeeding it without any intervening promoter or gene. For a design x, we obtain a 12-bit vector in this way. The function PTL takes two designs x and y and maps them to the Hamming distance between their 12-bit vectors. The PTL values range from 0 to 12 for the nifUSVWZM library. Formally, the PTL function is defined as follows:

$PerGenePTLBits(x, g) =$ $\begin{cases} (0, 0), & \text{if } CDS \ g \text{ has neither promoter or terminator } x \\ (0, 1), & \text{if } CDS \ g \text{ has no promoter but a terminator in } x \\ (1, 0), & \text{if } CDS \ g \text{ has a promoter but no terminator in } x \\ (1, 1), & \text{if } CDS \ g \text{ has a promoter and a terminator in } x \end{cases}$ $HammingDistance((a, b), (c, d)) = (a - c)^2 + (b - d)^2$ $PerGenePTL(x, y, g) =$ $\quad HammingDistance(PerGenePTLBits(x, g), PerGenePTLBits(y, g))$ $rawPTL(x, y) = \sum_{g \in \{U,S,V,W,Z,M\}} PerGenePTL(x, y, g)$ $PTL(x, y) = \dfrac{rawPTL(x, y)}{\max_{\text{over all } u,v \text{ in nifUSVWZM library}} rawPTL(u, v)}$ Lastly, the LEV (Levenstein) function specifically compares the similarity of the intergenic regions. For each CDS g, its context is defined as the sequence of parts preceding and succeeding it, up to but excluding the previous and next CDS in the design, respectively. This defines six pairs of intergenic part sequences, two for each gene in a design. The Levenstein distance between two sequences is the minimum number of insertions, deletions, and substitutions of elements in the sequences needed to transform one sequence into the other. The function LEV maps a pair of designs x and y to the sum of their component-wise Levenstein distances between the corresponding pairs of intergenic part sequences. The LEV values range from 0 to 24 for the nifUSVWZM library. Formally, the LEV function is defined as follows:

$CDSContext(x, g) = (\text{sequence of parts before } CDS \ g \text{ in } x,$ $\quad \text{sequence of parts after } CDS \ g \text{ in } x)$ $SequenceLEV(A, B) = \text{minimum number of insertions,}$ $\quad \text{deletions, and substitutions to transform sequence } A \text{ to } B$ $ContextLEV((A, B), (C, D)) = SequenceLEV(A, C) + SequenceLEV(B, D)$ $PerGeneLEV(x, y, g) = ContextLEV(CDSContext(x, g), CDSContext(y, g))$ $rawLEV(x, y) = \sum_{g \in \{U,S,V,W,Z,M\}} PerGeneLEV(x, y, g)$ $LEV(x, y) = \dfrac{rawLEV(x, y)}{\max_{\text{over all } u,v \text{ in nifUSVWZM library}} rawLEV(u, v)}$ The 84 nifUSVWZM sequences with edges <0.315 units according to the distance metric described above were provided as input for a Markov Clustering Algorithm (van Dongen, S. A., 2000) using default parameters. The algorithm is based on a stochastic simulation of flow on a graph of nodes, with flow between nodes weighted by their distance in genetic space. Flow is alternatingly expanded and contracted, and clusters of nodes are identified where flow is mostly trapped. The 23 clusters identified by this approach were laid out by hand and displayed with arcs indicating distance of <0.315 in the metric space. Nodes are shaded according to nitrogenase activity from blue (low activity) to red (high activity).

Robustness of Native nifUSVWZM Under T7* RNAP Control of the nifUSVWZM Library

The robustness of the natural nifUSVWZM operon to varying levels of induction was investigated with the orthogonal T7* RNAP expression system. The wild-type operon was cloned into the vector backbone of pCV27071 behind T7* promoter P2 (SBa_000445), such that the entire described 5'-untranslated region is maintained (ref 12). The resulting plasmid, pCV27001, was introduced to K. oxytoca NF10 with the T7* RNAP controller plasmid N249. The wild-type nifUSVWZM nitrogenase activity was measured via standard conditions with levels of IPTG ranging from 0.0316 mM to 3.16 mM (FIG. X (FIG. S8)). Wild-type activity levels at low induction fell to ~75% WT at high induction. FIG. X (FIG. S9) shows nitrogenase activity from the construct pCV27001 as a function of T7* RNAP expression Identification of Robust and Fragile Architectures of the nifUSVWZM Library To generate the T7* RNAP expression vs. normalized nitrogenase activity plots for FIG. 3, raw nitrogen fixation activities at each level of induction (attached Supplementary File) were first corrected for T7* RNAP-independent activity by subtracting the latter value from each data point, with a lower bound of 0 (i.e. corrected activity levels were not allowed to be negative). Next, nitrogen fixation was normalized to the maximum activity of each gene cluster across the range of induction levels assayed. For this study, a quantitative measure of robustness was generated by integrating under a 3rd order polynomial best fit curve. By this measure, possible robustness values fall between 0 and 1.

Figure 3B:
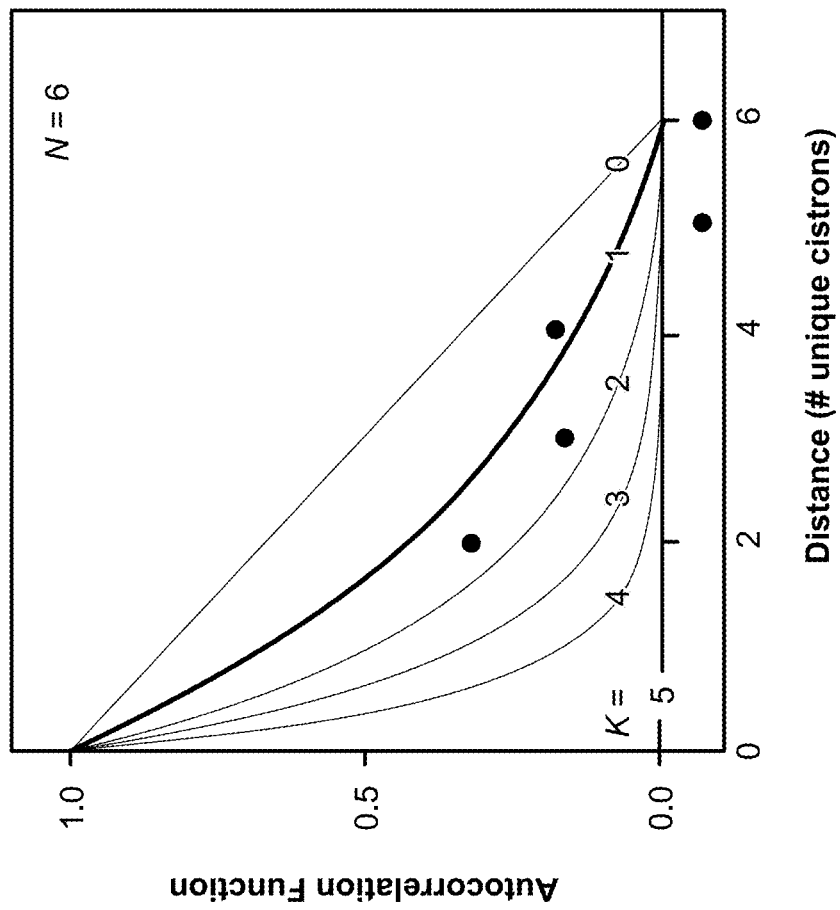
FIG. 3B shows experimental autocorrelation values plotted as a function of cistron-level hamming distance. Traces represent theoretical values for an NK-model landscape with N=6 and K=0-5. The black trace highlights the best fit to experimental data. Surface plots on left represent correlated (K=0), semi-correlated (K=2), or uncorrelated (K=N−1) landscapes.
Figure 3B:
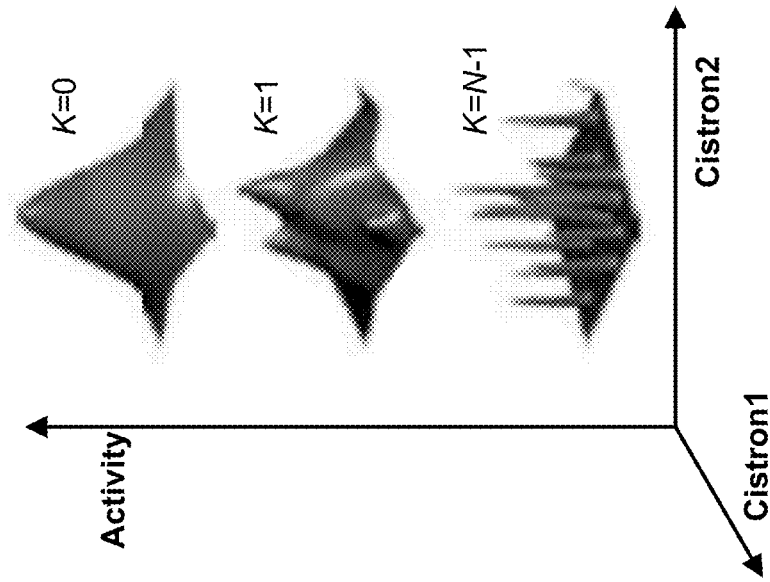

The variety of responses to increasing T7* RNAP expression was illustrated by manually grouping the top 57 normalized robustness traces (those whose variation is sufficiently larger than the measurement error) into 6 bins based on their rough overall shape: (i) convex increasing, (ii) concave/linear increasing, (iii) flat, (iv) convex decreasing, (v) linear decreasing, and (vi) peak-forming. The traces corresponding to the maximum and minimum robustness values for each group are highlighted in red and their robustness values are indicated in FIG. 3.

After binning the response curves based on their shapes, part enrichments or de-enrichments were examined using Pearson's chi-squared test 13, with the statistical critical value denoting a probability of p<0.05 that the enrichments are due to random chance. For each test, the frequency of a genetic part in the entire analyzed set of 57 constructs was taken as the expected probability of falling into one of the six bins by random chance. Chi-squared tests were applied individually for each bin by comparing the expected and observed frequency of part occurrence. Importantly, the original binning of the response curves was performed 'blindly' without reference to the corresponding genotypes.

Similar correlations to those described in Section IV-a above were investigated between general sequence features and robustness, however no significant correlations were observed.

Example 5

Efficiency of "Scarless Stitching" DNA Assembly Method
'The Scarless Stitching method was designed to join genetic sequences in a combinatorial manner without leaving residual scar sequences. While several scarless cloning methods have been described (Gibson, D. G., et al 2009; Gibson, D. G., et al. 2010; Moon, T. S., et al. 2012; Engler, C., et al. 2008), these typically would require unique flanking sequences to be designed to account for each unique part junction in a combinatorial library. Blunt-end ligations have likewise been described that generate scarless constructs, but these methods suffer from poor efficiency or lack of control over part orientation (Ali, S. and Steinkasserer, A., 1995). A method was devised to take advantage of the high-efficiency Golden Gate cloning method to join two parts in a single plasmid separated by a bridging sequence (encoding a lacZα peptide), and then subsequently removing the bridging sequence with a MlyI digestion and blunt-end ligation (FIG. 19).

This method is particularly suited for building multi-part constructs where the relative location of a given part-type is fixed. This method is used to construct 'cistron parts', which each consist of a promoter part, an RBS/CDS part, and a terminator part in that order. Such a design enables each member of the promoter part library to be cloned in front of any member of the RBS/CDS part library. Multi-part scarless constructs are built iteratively with preplanned flanking sequences to allow for subsequent ligations (FIG. 19), alternating between BsaI or BbsI type IIs restriction enzymes with each iteration.

An idempotent version of scarless stitching has likewise been designed which uses traditional restriction digestion/ligation reactions (FIG. 20). Idempotent cloning methods, like the BioBricks and BglBricks methods (Knight, T., 2003; Anderson, J. C., et al. 2010) hold the advantage that relative part order does not need to be pre-determined, and any part from a library can be integrated at any step. While this method was functional, it required multiple rounds of cloning/transformations for a single scarless junction and thus was too tedious for integration into the high-throughput assembly pipeline.

The Golden-Gate dependent, non-idempotent version was favored in the construction of libraries reported here as it allowed the scarless multipart construct to be formed in high efficiency with a two-step, one-pot reaction with high efficiency. This was demonstrated quantitatively using a model system in which a GFP expression construct was divided at a junction within the coding sequence and separated into scarless stiching assembly vectors. Constructs were reassembled using scarless stitching and $E.$ $coli$ transformations were scored. The approximate ratio of fluorescent (successful):white (non-fluorescent):blue (still containing the lacZα peptide) to be 20.4 (±2.1):2.6 (±1.0):1. This corresponds to 88.6%±4.9% success rate if the blue/white screen is employed, or at 84.9%±4.8% success rate if it is not. Sequencing revealed that white colonies resulted from either small deletions at the part junction that produced a frameshift in the GFP coding sequence, or from the complete absence of one of the GFP parts. Sequence verification of fluorescent colonies found 10/10 of the constructs were indeed scarless. In the assembly of the refactored nitrogenase libraries, the first round of Scarless Stitching proceeded with similar efficiencies to what was demonstrated in the model GFP assembly; however, the second iteration yielded small (1-2 bp) deletions at the new part junction in 70-80% of the sequenced products. This is expected to be the result of an exoclease activity of one of the reaction components, possibly BbsI. Attempts to improve the efficiency of this step by heat-killing the enzyme prior to digestion and intramolecular ligation with MlyI were unsuccessful.

Example 6

Key Plasmids Used in Examples 1-5.

| Plasmid | Description | Reference |
|---|---|---|
| N249 | Controller plasmid for T7* RNA polymerase expression | Temme, K, 2012 |
| SBa_000534 | Original refactored gene cluster | Temme, K, 2012 |
| pCV27001 | Wildtype nifUSVWZM operon preceded by promoter P2 | This study |
| pCV27002* | N249 with permutated RBS (E. coli controller) | This study |
| pCV27003 | N249 ΔT7* RNAP::sfGFP | This study |
| N110 | Internal standard for promoter characterization | Temme, K, 2012 |
| pCV27072 | mRFP Kelly promoter standard plasmid | Kelly, J. R., 2009 |
| pCV27073 | N110 with promoter P1 replacement | This study |
| pCV27074 | N110 with promoter P2 replacement | This study |
| pCV27075 | N110 with promoter P3 replacement | This study |
| pCV27076 | N110 with promoter P4 replacement | This study |
| N292 | Terminator T1 characterization plasmid | This study |
| pCV27077 | N292 with terminator T1 removed | Temme, K, 2012 |
| pCV27078 | N292 with terminator T4 replacement | This study |
| pCV27079 | N292 with terminator T5 replacement | This study |
| pCV27080 | N292 with terminator T6 replacement | This study |
| pCV27081 | N292 with terminator T7 replacement | This study |
| pCV27071 | Destination vector for all nif constructs | This study |
| pCV-usvwzm30[b] | Most active nifUSVWZM library construct | This study |
| pCV-usvwzm1[c] | Second active nifUSVWZM library construct | This study |
| pCV-cistron34[d] | Most active full cluster library construct | This study |
| pCV-cistron14[e] | Most active fully monocistronic construct | This study |

GenBank accession numbers:
[a]KF679804;
[b]KF679803;
[c]KF679802;
[d]KF679801;
[e]KF679800

REFERENCES

Aita, T., Husimi, Y. Adaptive walks by the fittest among finite random mutants on a Mt. Fugi-type fitness landscape. J. Theor. Biol. 193:383-405 (1998).

Alper, H., Fischer, C., Nevoigt, E., & Stephanopoulos, G. Tuning genetic control through promoter engineering. Proc. Natl. Acad. Sci. USA 102:12678-12683 (2005).

Bayer, T. S., et al. Synthesis of methyl halides from biomass using engineered microbes. J. Amer. Chem. Soc. 131: 6508-6515 (2009).

Bikard, D., Julie-Galau, S., Cambray, G., & Mazel, D. The synthetic integrin: an in vivo genetic shuffling device. Nucl. Acids Res. 38:e153 doi:10.1093/nar/gkq511 (2010).

Cardinale, S., & Arkin, A. P. Contextualizing context for synthetic biology identifying causes of failure of synthetic biological systems. Biotechnol. J. 7:856-866 (2012).

Chen, Y. J., et al. Characterization of 582 natural and synthetic terminators and quantification of their design constraints. Nat. Methods 10:659-664 (2013).

Cobb, R. E., Si, T., & Zhao, H. Directed evolution: an evolving and enabling synthetic biology tool. Curr. Opin. Chem. Biol. 16, 285-291 (2012).

Crameri, A., Dawes, G., Rodriguez Jr., E., Silver, S., & Stemmer, W. P. C. Molecular evolution of an arsenate detoxification pathway by DNA shuffling. Nat. Biotechnol. 15:436-438 (1997).

Crook, N. C., Freeman, E. S., & Alper, H. S. Re-engineering multicloning sites for function and convenience. Nucl. Acids Res. 39:e92 doi: 10.1093/nar/gkr346 (2011).

Dandekar, T., Snel, B., Huynen, M., & Bork, P. Conservation of gene order: a fingerprint of proteins that physically interact. Trends Biochem. Sci. 23:324-328 (1998).

de Raad, M., Kooijmans, S. A. A., Teunissen, E. A., & Mastrobattista, E. A solid-phase platform for combinatorial and scarless multipart gene assembly. ACS Synth. Biol. 2:316-326 (2013).

Du, J., Yuan, Y., Si, T., Lian, J., & Zhao, H. Customized optimization of metabolic pathways by combinatorial transcriptional engineering. Nucl. Acids Res. 40:e142 doi:10.1093/nar/gks549 (2012).

Engler, C., Kandzia, R., & Marillonnet, S. (2008) A one pot, one step, precision cloning method with high throughput capability. PLoS ONE 3:e3647 doi:10.1371/journal.pone.0003647.

Enkh-Amgalan, J., Kawasaki, H., & Seki, T. Molecular evolution of the nif gene cluster carrying nifI1 and nifI2 genes in the Gram-positive phototrophic bacterium *Heliobacterium chlorum*. Internat. J. Sys. Evol. Microbiol. 56:65-74 (2006).

Fischbach, M. A., Walsh, C. T., & Clardy, J. The evolution of gene collectives: how natural selection drives chemical innovation. Proc. Natl. Acad. Sci. USA 105:4601-4608 (2008).

Fontana, W., Stadler, P. F., Bornberg-Bauer, E. G., Griesmacher, T., Hofacker, I. L., Tacker, M., Tarazona, P., Weinberger, E. D., & Schuster, P. RNA folding and combinatory landscapes. Phys. Rev. E. 47:2083-2099 (1993).

Gibson, D. G., et al. Enzymatic assembly of DNA molecules up to several hundred kilobases. Nat. Methods 6:343-345 (2009).

Gibson, D. G., Smith, H. O., Hutchison III, C. A., Venter, J. C., & Merryman, C. Chemical synthesis of the mouse mitochondrial genome. Nat. Methods 7, 901-903 (2010).

Güell, M., et al. Transcriptome complexity in a genome-reduced bacterium. Science 326:1268-1271 (2009).

Huynen, M. A., Stadler, P. F., & Fontana, W. Smoothness within ruggedness: the role of neutrality in adaptation. Proc. Natl. Acad. Sci. USA 93:397-401 (1996).

Iber, D. A quantitative study of the benefits of co-regulation using the spoIIA operon as an example. Mol. Sys. Biol. 2, 1-6 (2006).

Jensen, K. F. The *Escherichia coli* K-12 "wild types" W3110 and MG1655 have an rph frameshift mutation that leads to pyrimidine starvation due to low pyre expression levels. J. Bacteriol. 175:3401-3407 (1993).

Kaneko, T., et al. Complete genomic structure of the cultivated rice endophyte *Azospirillum* sp. B510. DNA Res. 17:37-50 (2010).

Levin-Karp, A., et al. Quantifying translational coupling in *E. coli* synthetic operons using RBS modulation and fluorescent reporters. ACS Synth. Biol. 2:327-336 (2013).

Liang, L. W., Hussein, R., Block, D. H. S., & Lim H. N. Minimal effect of gene clustering on expression in *Escherichia coli*. Genetics 193, 453-465 (2013).

Lim, H. N., Lee, Y., & Hussein, R. Fundamental relationship between operon organization and gene expression. Proc. Natl. Acad. Sci. USA 108, 10626-10631 (2011).

Lucks J. B., Qi, L., Whitaker, W. R., & Arkin, A. P. Toward scalable parts families for predictable design of biological circuits. Curr. Opin. Microbiol. 11, 567-573 (2008).

Martinez-Noël, G., Curatti, L., Hernandez, J. A., & Rubio, L. M. NifB and NifEN protein levels are regulated by ClpX2 under nitrogen fixation conditions in *Azotobacter vinelandii*. Mol. Microbol. 79:1182-1193 (2011).

Medema, M., Breitling, R., Bovenberg, R., & Takano, E., Exploiting plug-and-play synthetic biology for drug discovery and production in microorganisms. Nat. Rev. Microbiol. 9:131-137 (2011).

Moon, T. S., Lou, C., Tamsir, A., Stanton, B. C., & Voigt, C. A. Genetic programs constructed from layered logic gates in single cells. Nature 491, 249-253 (2012).

Mutalik, V. K., et al. Quantitative estimation of activity and quality for collections of functional genetic elements. Nat. Methods 10:347-353 (2013).

Noskov, V. N., et al. Assembly of large, high G+C bacterial DNA fragments in yeast. ACS Synth. Biol. 1:267-273 (2012).

Oh, C. J., et al. Organization of nif gene cluster in *Frankia* sp. EuIK1 strain, a symbiont of *Elaeagnus umbellata*. Arch. Microbiol. 194:29-34 (2012).

Pfleger, B. F., Pitera, D. J., Smolke, C. D., & Keasling, J. D. Combinatorial engineering of intergenic regions in operons tunes expression of multiple genes. Nat. Biotech. 24:1027-1032 (2006).

Price, M. N., Huang, K. H., Arkin, A. P., & Alm, E. J. Operon formation is driven by coregulation and not by horizontal gene transfer. Genome Res. 15, 809-819 (2005).

Price, M. N., Arkin, A. P., & Alm, E. J. The life-cycle of operons. PLoS Genet. 2, e96. doi: 10.1371/journal.pgen.0020096 (2006).

Ramon, A., & Smith, H. O. Single-step linker-based combinatorial assembly of promoter and gene cassettes for pathway engineering. Biotechnol. Lett. 33:549-555 (2011).

Ran, L., et al. Genome erosion in a nitrogen-fixing vertically transmitted endosymbiotic multicellular cyanobacterium. PLoS ONE 5:e11486 doi:10.1371/journal.pone.0011486 (2010)

Sambrook, J., Fritsch, E. F., & Maniatis, T. Molecular cloning: a laboratory reference manual. Cold Spring Harbor, N.Y.: Cold Spring Harbor Laboratory Press (1989).

Schmidt-Dannert, C., Umeno, D., & Arnold, F. H., Molecular breeding of carotenoid biosynthetic pathways. Nat. Biotechnol. 18:750-753 (2000).

Sleigh, S. C., & Sauro, H. M. Randomized BioBrick assembly: a novel DNA assembly method for randomizing and optimizing genetic circuits and metabolic pathways. ACS Synth. Biol. just accepted Jul. 22, 2013.

Sorek, R., & Cossart, P. Prokaryotic transcriptomics: a new view on regulation, physiology, and pathogenicity. Nat. Rev. Genet. 11:9-16 (2010).

Stacy, G. S., Burris, R. H., Evans, H. J. Biological nitrogen fixation. Chapman and Hall, New York (1992).

Stephanopoulos, G., Challenges in engineering microbes for biofuels production. Science 315:801-804 (2007).

Stewart, W. D., Fitzgerald, G. P., & Burris, R. H. In situ studies on nitrogen fixation with the acetylene reduction technique. Science 158, 536 (1967).

Stucken, K., et al. The smallest known genomes of multicellular and toxic cyanobacteria: comparison, minimal gene sets for linked traits and the evolutionary implications. PLoS ONE 5:e9235 doi:10.1371/journal.pone/0009235 (2010).

Suh, M. H., Pulakat, L., & Gavini, N. Functional expression of the FeMo-cofacter specific biosynthetic genes nifEN as a NifE-N fusion protein synthesizing unit in *Azotobacter vinelandii*. Biochem. Biophys. Res. Comm. 299:233-240 (2002).

Temme, K., Zhao, D., & Voigt, C. A. Refactoring the nitrogen fixation gene cluster from *Klebsiella oxytoca*. Proc. Natl. Acad. Sci. USA 109:7085-7090 (2012).

Temme K., Hill, R., Segall-Shapiro, T. H., Moser, F., & Voigt, C. A. Modular control of multiple pathways using engineered orthogonal T7 polymerases. Nucl. Acid Res. 40:8773-8781 (2012)

Thiel, T., Lyons, E. M., & Erker, J. C., Characterization of genes for a second Modependent nitrogenase in the cyanobacterium *Anabaena variabilis*. J. Bact. 179:5222-5225 (1997).

Weber, E., Engler, C., Gruetzner, R., Werner, S., & Marillonnet, S. A modular cloning system for standardized assembly of multigene constructs. (2011) PLoS ONE 6:e16765 doi:10.1371/journal.pone.0016765.

Werner, S., Engler, C., Weber, E., Gruetzner, R, & Marillonnet, S. Fast track assembly of multigene constructs using Golden Gate cloning and the MoClo System. Bioeng. Bugs 3:38-43 (2012).

Wells, J. A. Additivity of mutational effects in proteins. Biochemistry 29:8509-8517 (1990).

Wu, J., et al. Multivariate modular metabolic engineering of *Escherichia coli* to produce resveratrol from L-tyrosine. J. Biotechnol. (2013), dx.doi.org/10.1016/j.jbiotec.2013.07.030.

Xu, P., Vansiri, A., Bhan, N., & Koffas, M. A. G. ePathBrick: a synthetic biology platform for engineering metabolic pathways in *E. coli*. ACS Synth. Biol. 1:256 266 (2012).

Yokobayashi, Y., Weiss, R., & Arnold, F. H. Directed evolution of a genetic circuit. Proc. Natl. Acad. Sci. USA 99:16587-16591 (2002).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for scarless stitching comprising
identifying at least three consecutive units of a genetic construct, wherein each of the at least three consecutive units is in a partial plasmid and is flanked by a 4-10 nucleotide upstream and downstream flanking sequence that forms 5' cohesive ends when digested with a restriction enzyme, wherein the at least three consecutive units comprises a first unit, a second unit, and a third unit, wherein the first unit, the second unit, and the third unit each comprise one or more nif cluster genetic components, digesting the first and second units with a first restriction enzyme and digesting the third unit with a second restriction enzyme to produce cohesive ends, and ligating the cohesive ends to produce a plasmid.

2. The method of claim 1, wherein the first unit is a regulatory unit.

3. The method of claim 2, wherein the regulatory unit is a promoter unit.

4. The method of claim 1, wherein the second unit is a Ribosomal binding site (RBS) unit, a coding DNA sequence (CDS) unit, or a combined RBS/CDS unit.

5. The method of claim 1, wherein the third unit is a terminator unit.

6. The method of claim 1, wherein the flanking sequences are 6 nucleotides in length.

7. The method of claim 1, wherein the one or more nif cluster genetic components of the first unit, the second unit, the third unit, or any combination thereof is derived from a *Klebsiella oxytoca* nif cluster, an *Azotobacter vinelandii* nif cluster, an *Anabaena variabilis* nif cluster, a *Methanococcus maripaludis* nif cluster, a *Bradyrhizobium japonicum* nif cluster, a *Nodularia spumigena* nif cluster nif cluster, a *Nostoc* sp. nif cluster, a *Paludibacter propionicigenes* nif cluster, a *Pelosinus fermentans* nif cluster, a *Sinorhizobium meliloti* nif cluster, a *Arcobacter* sp. nif cluster, a *Frankia* sp. nif cluster, a *Rhodobacter capsulatus* nif cluster, a *Nostoc azollae* nif cluster, or a *Cyanothece* sp. nif cluster.

8. The method of claim 1, wherein the one or more nif cluster genetic components of the first unit, the second unit, the third unit, or any combination thereof is derived from a nifUSVWZM operon from *Klebsiella oxytoca*.

9. The method of claim 1, wherein the first unit comprises a transcription factor binding site.

10. The method of claim 1, wherein the first unit, the second unit, or the third unit comprises at least one gene selected from the list consisting of: MA rufH, MfD, nifK, nifY, ntfE, rufN, ntfU, ntfS, nifV, ntfW, ntfZ, ntfM, nifF, MfB, and nifQ.

11. The method of claim 1, wherein producing the plasmid by ligating the cohesive ends comprises removing a native regulatory element which is linked to the first unit, the second unit, or the third unit in the partial plasmid.

12. The method of claim 1, wherein the plasmid comprises a synthetic regulatory element.

13. The method of claim 1, wherein the plasmid comprises nif cluster genes which are in a different order relative to the order of the nif cluster genes in a corresponding native nif genetic cluster.

14. The method of claim 1, wherein the plasmid comprises nif cluster genes which are reassembled in a different orientation relative to the orientation of the nif cluster genes in a corresponding native nif genetic cluster.

15. The method of claim 10, wherein the plasmid comprises a promoter that has a different strength relative to the native promoter of the at least one gene.

16. The method of claim 10, wherein the plasmid comprises a terminator that has a different strength relative to the native terminator of the at least one gene.

17. The method of claim 1, wherein the plasmid comprises a controller.

18. The method of claim 1, wherein the plasmid produced by the method comprises a refactored nif cluster.

* * * * *

UNITED STATES PATENT AND TRADEMARK OFFICE
CERTIFICATE OF CORRECTION

PATENT NO. : 11,946,162 B2
APPLICATION NO. : 17/204219
DATED : April 2, 2024
INVENTOR(S) : Dehua Zhao et al.

It is certified that error appears in the above-identified patent and that said Letters Patent is hereby corrected as shown below:

In the Claims

At Column 55, Line 28 through Column 56, Line 3:
"The method of claim 1, wherein the first unit, the second unit, or the third unit comprises at least one gene selected from the list consisting of: MA rufH, MfD, nifK, nifY, ntfE, rufN, ntfU, ntfS, nifV, ntfW, ntfZ, ntfM, nifF, MfB, and nifQ."
Should read:
-- The method of claim 1, wherein the first unit, the second unit, or the third unit comprises at least one gene selected from the list consisting of: nifJ, nifH, nifD, nifK, nifY, nifE, nifN, nifU, nifS, nifV, nifW, nifZ, nifM, nifF, nifB, and nifQ. --

Signed and Sealed this
Twenty-first Day of May, 2024

Katherine Kelly Vidal
*Director of the United States Patent and Trademark Office*

SEQUENCE LISTING

```
<160> NUMBER OF SEQ ID NOS: 34

<210> SEQ ID NO 1
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1
ggtctcctac tagactc                                                  17

<210> SEQ ID NO 2
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 2
ggagaggatg atctgag                                                  17

<210> SEQ ID NO 3
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 3
gagtcaaatg cgagacc                                                  17

<210> SEQ ID NO 4
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 4
ctcagtttac gctctgg                                                  17
```

<210> SEQ ID NO 5
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 5
ggtctcggga g                                                             11

<210> SEQ ID NO 6
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 6
ccagagccct c                                                             11

<210> SEQ ID NO 7
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 7
tactcgagac c                                                             11

<210> SEQ ID NO 8
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 8
atgagctctg g                                                             11

<210> SEQ ID NO 9
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 9
ggtctcgaat g                                                             11

<210> SEQ ID NO 10
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 10
ccagagctta c                                                             11

<210> SEQ ID NO 11
<211> LENGTH: 11
<212> TYPE: DNA
<213> ORGANISM: Artificial Sequence
<220> FEATURE:
<223> OTHER INFORMATION: Synthetic Polynucleotide

```
<400> SEQUENCE: 11
aggtcgagac c                                                              11

<210> SEQ ID NO 12
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 12
tccagctctg g                                                              11

<210> SEQ ID NO 13
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 13
gaagaccagg agcgagacc                                                      19

<210> SEQ ID NO 14
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 14
cttctggtcc tcgctctgg                                                      19

<210> SEQ ID NO 15
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 15
ggtctccagg tccgtcttc                                                      19

<210> SEQ ID NO 16
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 16
ccagaggtcc aggcagaag                                                      19

<210> SEQ ID NO 17
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 17
gaagaccagg ag                                                             12
```

```
<210> SEQ ID NO 18
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 18
cttctggtcc tc                                                            12

<210> SEQ ID NO 19
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 19
tactagactc                                                               10

<210> SEQ ID NO 20
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 20
atgatctgag                                                               10

<210> SEQ ID NO 21
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 21
gagtcaaatg                                                               10

<210> SEQ ID NO 22
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 22
ctcagtttac                                                               10

<210> SEQ ID NO 23
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 23
aggtccgtct tc                                                            12

<210> SEQ ID NO 24
<211> LENGTH: 12
<212> TYPE: DNA
<213> ORGANISM: Artificial Sequence
<220> FEATURE:
<223> OTHER INFORMATION: Synthetic Polynucleotide
```

```
<400> SEQUENCE: 24
tccaggcaga ag                                                              12

<210> SEQ ID NO 25
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(16)
<223> OTHER INFORMATION: n is a, c, g, or t

<400> SEQUENCE: 25
gaattcnnnn nnnnnnctgc agactc                                               26

<210> SEQ ID NO 26
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(16)
<223> OTHER INFORMATION: n is a, c, g, or t

<400> SEQUENCE: 26
cttaagnnnn nnnnnngacg tctgag                                               26

<210> SEQ ID NO 27
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(20)
<223> OTHER INFORMATION: n is a, c, g, or t

<400> SEQUENCE: 27
gactcaattg nnnnnnnnnn atgcat                                               26

<210> SEQ ID NO 28
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(20)
<223> OTHER INFORMATION: n is a, c, g, or t

<400> SEQUENCE: 28
ctcagttaac nnnnnnnnnn tacgta                                               26

<210> SEQ ID NO 29
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 29
atgcagactc                                                                 10
```

```
<210> SEQ ID NO 30
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 30
tacgtctgag                                                                  10

<210> SEQ ID NO 31
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(20)
<223> OTHER INFORMATION: n is a, c, g, or t

<400> SEQUENCE: 31
gagtcaattg nnnnnnnnnn atgcat                                                26

<210> SEQ ID NO 32
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(20)
<223> OTHER INFORMATION: n is a, c, g, or t

<400> SEQUENCE: 32
ctcagttaac nnnnnnnnnn tacgta                                                26

<210> SEQ ID NO 33
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 33
gagtcaattc                                                                  10

<210> SEQ ID NO 34
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 34
ctcagttaag                                                                  10
```